US012788780B2

(12) United States Patent
Woods et al.

(10) Patent No.: US 12,788,780 B2
(45) Date of Patent: Nov. 10, 2026

(54) METHODS OF CELL THERAPIES

(71) Applicant: OSSIUM HEALTH, INC., San Francisco, CA (US)

(72) Inventors: Erik J. Woods, Carmel, IN (US); Brian H. Johnstone, Fishers, IN (US); Dongsheng Gu, Indianapolis, IN (US); Aubrey Marie Sherry, Carmel, IN (US); Kelsey Gwen Musall, Avon, IN (US); Megan Sykes, New York, NY (US); Tomoaki Kato, New York, NY (US); Jianing Fu, New York, NY (US)

(73) Assignee: OSSIUM HEALTH, INC., San Francisco, CA (US)

( * ) Notice: Subject to any disclaimer, the term of this patent is extended or adjusted under 35 U.S.C. 154(b) by 262 days.

(21) Appl. No.: 18/456,422

(22) Filed: Aug. 25, 2023

(65) Prior Publication Data

US 2024/0207322 A1 Jun. 27, 2024

Related U.S. Application Data

(63) Continuation of application No. 17/696,779, filed on Mar. 16, 2022, now Pat. No. 11,786,558, which is a continuation of application No. PCT/US2021/064152, filed on Dec. 17, 2021.

(60) Provisional application No. 63/127,949, filed on Dec. 18, 2020.

(51) Int. Cl.

| | |
|---|---|
| ***A61K 35/28*** | (2015.01) |
| ***A61K 31/436*** | (2006.01) |
| ***A61K 35/17*** | (2015.01) |
| ***A61K 35/38*** | (2015.01) |
| ***A61K 38/17*** | (2006.01) |
| ***A61K 40/10*** | (2025.01) |
| ***A61K 40/22*** | (2025.01) |
| ***A61P 37/06*** | (2006.01) |
| ***C12N 5/0783*** | (2010.01) |
| ***C12N 5/0789*** | (2010.01) |

(52) U.S. Cl.

CPC ............ *A61K 35/28* (2013.01); *A61K 31/436* (2013.01); *A61K 35/17* (2013.01); *A61K 35/38* (2013.01); *A61K 38/1774* (2013.01); *A61K 40/10* (2025.01); *A61K 40/22* (2025.01); *A61P 37/06* (2018.01); *C12N 5/0636* (2013.01); *C12N 5/0647* (2013.01)

(58) Field of Classification Search

None

See application file for complete search history.

(56) References Cited

U.S. PATENT DOCUMENTS

| | | | |
|---|---|---|---|
| 4,674,184 | A | 6/1987 | Anderson |
| 4,710,472 | A | 12/1987 | Saur et al. |
| 5,474,687 | A | 12/1995 | Van Vlasselaer |
| 5,672,346 | A | 9/1997 | Srour et al. |
| 5,766,944 | A | 6/1998 | Ruiz |
| 5,840,580 | A | 11/1998 | Terstappen et al. |
| 5,858,782 | A | 1/1999 | Long et al. |
| 6,739,112 | B1 | 5/2004 | Marino |
| 6,900,029 | B1 | 5/2005 | Coulter et al. |
| 7,470,538 | B2 | 12/2008 | Laughlin et al. |
| 7,547,210 | B1 | 6/2009 | Valen |
| 7,604,930 | B1 | 10/2009 | Gao et al. |
| 7,794,705 | B2 | 9/2010 | Pecora et al. |
| 7,883,698 | B2 | 2/2011 | Michejda |
| 7,915,043 | B2 | 3/2011 | Caligiuri et al. |
| 7,927,785 | B2 | 4/2011 | Milhem et al. |
| 8,048,618 | B2 | 11/2011 | Luk et al. |
| 8,088,370 | B2 | 1/2012 | Pecora et al. |
| 8,343,485 | B2 | 1/2013 | Pecora et al. |
| 8,425,899 | B2 | 4/2013 | Pecora et al. |
| 8,637,005 | B2 | 1/2014 | Pecora et al. |
| 8,709,403 | B2 | 4/2014 | Pecora et al. |
| 8,956,862 | B2 | 2/2015 | Pal et al. |
| 9,034,316 | B2 | 5/2015 | Pecora et al. |
| 9,078,429 | B2 | 7/2015 | McGann et al. |
| 9,192,695 | B2 | 11/2015 | Shi |
| 9,241,959 | B2 | 1/2016 | Tang |
| 9,402,377 | B2 | 8/2016 | Flavell et al. |
| 9,409,906 | B2 | 8/2016 | Sauvageau et al. |
| 9,499,792 | B2 | 11/2016 | Chretien et al. |
| 9,504,717 | B2 | 11/2016 | Strober et al. |
| 9,533,010 | B2 | 1/2017 | Pecora et al. |
| 9,534,202 | B2 | 1/2017 | Pecora et al. |
| 9,561,253 | B2 | 2/2017 | Strober et al. |

(Continued)

FOREIGN PATENT DOCUMENTS

| | | | |
|---|---|---|---|
| CN | 1058991 | C | 11/2000 |
| CN | 104357396 | A | 2/2015 |

(Continued)

OTHER PUBLICATIONS

AATB. Guidance Document, in Evaluation of Body Cooling at Standard D5.400. 2013. American Association of Tissue Banks: McLean, VA. p. 13.

(Continued)

*Primary Examiner* — Daniel C Gamett

(74) *Attorney, Agent, or Firm* — Knobbe Martens Olson & Bear LLP

(57) ABSTRACT

Described herein are methods of cell therapies. Also described herein are methods of generating donor derived T cells in an organ transplant recipient, by administering bone marrow stem cells to the organ transplant recipient about 1 to about 30 days after the organ transplant recipient receives one or more organ transplants.

15 Claims, 33 Drawing Sheets

(56) References Cited

U.S. PATENT DOCUMENTS

| | | | |
|---|---|---|---|
| 9,675,643 | B2 | 6/2017 | Weston et al. |
| 9,675,644 | B2 | 6/2017 | Weston et al. |
| 9,687,511 | B2 | 6/2017 | Weston et al. |
| 9,808,558 | B2 | 11/2017 | Shi |
| 9,814,803 | B2 | 11/2017 | Shi |
| 9,828,586 | B2 | 11/2017 | Tom et al. |
| 9,945,854 | B2 | 4/2018 | Altman et al. |
| 9,963,678 | B2 | 5/2018 | Tom et al. |
| 9,974,807 | B2 | 5/2018 | Strober et al. |
| 10,047,344 | B2 | 8/2018 | Poon et al. |
| 10,076,113 | B2 | 9/2018 | Chretien et al. |
| 10,076,542 | B2 | 9/2018 | Strober et al. |
| 10,080,769 | B2 | 9/2018 | Strober et al. |
| 10,143,562 | B2 | 12/2018 | Malinin |
| 10,159,694 | B2 | 12/2018 | Strober et al. |
| 10,183,043 | B2 | 1/2019 | Strober et al. |
| 10,258,648 | B2 | 4/2019 | Strober et al. |
| 10,286,112 | B2 | 5/2019 | Govil |
| 10,400,218 | B2 | 9/2019 | Itescu et al. |
| 10,472,608 | B2 | 11/2019 | Bader et al. |
| 10,513,690 | B2 | 12/2019 | Ganey et al. |
| 10,550,369 | B2 | 2/2020 | Tom et al. |
| 10,603,340 | B2 | 3/2020 | Strober et al. |
| 10,645,921 | B2 | 5/2020 | Temple et al. |
| 10,660,329 | B2 | 5/2020 | Ivanovic et al. |
| 10,660,954 | B2 | 5/2020 | Mitchell et al. |
| 10,669,528 | B2 | 6/2020 | Rossi et al. |
| 10,995,318 | B2 | 5/2021 | Woods et al. |
| 11,085,024 | B2 | 8/2021 | Woods et al. |
| 11,104,882 | B2 | 8/2021 | Woods et al. |
| 11,447,750 | B2 | 9/2022 | Woods et al. |
| 11,697,799 | B2 | 7/2023 | Woods et al. |
| 11,702,637 | B2 | 7/2023 | Woods et al. |
| 11,744,243 | B2 | 9/2023 | Woods et al. |
| 2002/0039786 | A1 | 4/2002 | Reid et al. |
| 2002/0182186 | A1 | 12/2002 | Loeb |
| 2003/0082158 | A1 | 5/2003 | Symonds et al. |
| 2003/0161817 | A1 | 8/2003 | Young et al. |
| 2004/0072347 | A1 | 4/2004 | Schuler et al. |
| 2004/0107453 | A1 | 6/2004 | Furcht et al. |
| 2004/0156834 | A1 | 8/2004 | Slavin et al. |
| 2004/0258670 | A1 | 12/2004 | Laughlin et al. |
| 2005/0233299 | A1 | 10/2005 | Sawa et al. |
| 2007/0036734 | A1 | 2/2007 | Tahara et al. |
| 2007/0190023 | A1 | 8/2007 | Battista et al. |
| 2007/0224587 | A1 | 9/2007 | Forsell et al. |
| 2010/0178279 | A1 | 7/2010 | Cunningham-Rundles et al. |
| 2010/0260721 | A1 | 10/2010 | McGonagie et al. |
| 2010/0310535 | A1 | 12/2010 | Nakamura et al. |
| 2010/0310536 | A1 | 12/2010 | Nakamura et al. |
| 2012/0020934 | A1 | 1/2012 | Ma |
| 2012/0052049 | A1 | 3/2012 | Woods et al. |
| 2012/0276581 | A1 | 11/2012 | Arav et al. |
| 2012/0276628 | A1 | 11/2012 | Khan et al. |
| 2013/0011376 | A1 | 1/2013 | Peled et al. |
| 2013/0216495 | A1 | 8/2013 | Motlagh et al. |
| 2013/0236433 | A1 | 9/2013 | Webster |
| 2013/0302293 | A1 | 11/2013 | Webster |
| 2014/0363437 | A1 | 12/2014 | Reisner et al. |
| 2015/0203820 | A1 | 7/2015 | Wang et al. |
| 2015/0216911 | A1 | 8/2015 | Vines et al. |
| 2016/0000062 | A1 | 1/2016 | Chen et al. |
| 2016/0089401 | A1 | 3/2016 | Woods et al. |
| 2016/0101134 | A1 | 4/2016 | Tang |
| 2016/0175198 | A1 | 6/2016 | Warner et al. |
| 2017/0035935 | A1 | 2/2017 | Uveges et al. |
| 2017/0151287 | A1 | 6/2017 | Von Maltzahn et al. |
| 2017/0198257 | A1 | 7/2017 | Bader et al. |
| 2017/0239390 | A1 | 8/2017 | Ganey et al. |
| 2017/0240862 | A1 | 8/2017 | Ganey et al. |
| 2017/0247659 | A1 | 8/2017 | Ganey et al. |
| 2018/0169301 | A1 | 6/2018 | Temple et al. |
| 2018/0214487 | A1 | 8/2018 | Fiorina et al. |
| 2018/0221410 | A1 | 8/2018 | Strober et al. |
| 2018/0243337 | A1 | 8/2018 | Strober et al. |
| 2018/0282762 | A1 | 10/2018 | Gori |
| 2018/0326122 | A1 | 11/2018 | Ganey et al. |
| 2018/0334655 | A1 | 11/2018 | Ganey et al. |
| 2018/0353541 | A1 | 12/2018 | Delaney |
| 2019/0000877 | A1 | 1/2019 | Strober et al. |
| 2019/0083530 | A1 | 3/2019 | Strober et al. |
| 2019/0091262 | A1 | 3/2019 | Strober et al. |
| 2019/0151506 | A1 | 5/2019 | Ganey et al. |
| 2019/0191694 | A1 | 6/2019 | Temple et al. |
| 2019/0192561 | A1 | 6/2019 | Strober et al. |
| 2019/0192562 | A1 | 6/2019 | Strober et al. |
| 2019/0298762 | A1 | 10/2019 | Strober et al. |
| 2019/0336528 | A1 | 11/2019 | Strober et al. |
| 2019/0343112 | A1 | 11/2019 | Woods et al. |
| 2019/0345450 | A1 | 11/2019 | Radtke et al. |
| 2019/0358257 | A1 | 11/2019 | Strober et al. |
| 2020/0016198 | A1 | 1/2020 | Jongen et al. |
| 2020/0054788 | A1 | 2/2020 | Temple et al. |
| 2020/0054789 | A1 | 2/2020 | Temple et al. |
| 2020/0088718 | A1 | 3/2020 | Zdanowski et al. |
| 2020/0205399 | A1 | 7/2020 | Shao et al. |
| 2020/0254015 | A1 | 8/2020 | Strober et al. |
| 2020/0325451 | A1 | 10/2020 | Woods et al. |
| 2020/0337648 | A1 | 10/2020 | Saripalli et al. |
| 2020/0399604 | A1 | 12/2020 | Woods et al. |
| 2020/0399605 | A1 | 12/2020 | Woods et al. |
| 2020/0399606 | A1 | 12/2020 | Woods et al. |
| 2020/0399607 | A1 | 12/2020 | Woods et al. |
| 2021/0214688 | A1 | 7/2021 | Woods et al. |
| 2021/0369782 | A1 | 12/2021 | Agarwal et al. |
| 2022/0183275 | A1 | 6/2022 | Woods et al. |
| 2022/0186187 | A1 | 6/2022 | Woods et al. |
| 2022/0241342 | A1 | 8/2022 | Woods et al. |
| 2024/0164371 | A1 | 5/2024 | Woods et al. |
| 2024/0240151 | A1 | 7/2024 | Woods et al. |
| 2024/0271097 | A1 | 8/2024 | Woods et al. |

FOREIGN PATENT DOCUMENTS

| | | | |
|---|---|---|---|
| CN | 107012119 | A | 8/2017 |
| CN | 110777114 | A | 2/2020 |
| EP | 3107995 | B1 | 10/2019 |
| RU | 2012151191 | A | 6/2014 |
| WO | WO 1993/007824 | A1 | 4/1993 |
| WO | WO 1999/025367 | A2 | 5/1999 |
| WO | WO 2000/036090 | A2 | 6/2000 |
| WO | WO 2003/024215 | A1 | 3/2003 |
| WO | WO 2005/001033 | A2 | 1/2005 |
| WO | WO 2005/032251 | A1 | 4/2005 |
| WO | WO 2008/121120 | A1 | 10/2008 |
| WO | WO 2011069117 | A1 | 6/2011 |
| WO | WO 2011/151452 | A1 | 12/2011 |
| WO | WO 2016/210292 | A1 | 12/2016 |
| WO | WO 2017/127755 | A1 | 7/2017 |
| WO | WO 2017/216775 | A3 | 2/2018 |
| WO | WO 2017/218948 | A3 | 2/2018 |
| WO | WO 2018/022651 | A1 | 2/2018 |
| WO | WO 2018/051340 | A1 | 3/2018 |
| WO | WO 2019/006328 | A1 | 1/2019 |
| WO | WO 2020/047236 | A1 | 3/2020 |
| WO | WO 2020/058324 | A1 | 3/2020 |
| WO | WO 2020/061180 | A1 | 3/2020 |
| WO | WO 2019/026910 | A1 | 7/2020 |
| WO | WO 2020/214400 | A1 | 10/2020 |
| WO | WO 2020/247341 | A1 | 12/2020 |
| WO | WO 2021/236711 | A1 | 11/2021 |
| WO | WO 2022/020210 | A1 | 1/2022 |
| WO | WO 2022/081896 | A1 | 4/2022 |
| WO | WO 2022/081909 | A1 | 4/2022 |
| WO | WO 2022/133282 | A1 | 6/2022 |
| WO | WO 2022/140296 | A1 | 6/2022 |
| WO | WO 2022/159824 | A1 | 7/2022 |

OTHER PUBLICATIONS

Ahrens et al., Mesenchymal stem cell content of human vertebral bone marrow. Transplantation, 2004. 78(6): 925-929.

(56) References Cited

OTHER PUBLICATIONS

Aimulhem N., Cryopreservation and Hypothermal Storage of Hemotopoietic Stem Cells. Thesis; University of Cincinnati. May 30, 2013; (Year 2015) in 72 pages.
Banfi et al., Replicative Aging and Gene Expression in Long-term Cultures of Human Bone Marrow Stromal Cells. Tissue Eng, 2002. 8(6): p. 901-910.
Bara et al., Concise Review: Bone Marrow-Derived Mesenchymal Stem Cells Change PhenotypeFollowing in Vitro Culture: Implications for Basic Research and the Clinic. Stem Cells, 2014. 32(7): p. 1713-1723.
Baumert et al., Bone Marrow of Multiorgan Donors Underutilized: Implications for Improvement of Accessibility of Hematopoietic Cells for Transplantations. Transplantation Jan. 27, 2012;93(2): p. 165-171.
Baxter et al., Study of Telomere Length Reveals Rapid Aging of Human Marrow Stromal Cells Following in Vitro Expansion. Stem Cells, 2004. 22(5): p. 675-682.
Bender et al., Impact of Freeze-Thaw on Isolation of Viable CD34+ Cells from Human Cadaveric Bone Marrow. The Faseb J. Apr. 2020;34(S1): Abstract.
Bensidhoum et al., Homing of In Vitro Expanded Stro-1- or Stro-1+ Human Mesenchymal Stem Cells into the NOD/SCIO Mouse and Their Role in Supporting Human CD34 Cell Engraftment. Blood, 2004. 103(9): p. 3313-3319.
Berz et al., Cryopreservation of Hematopoietic Stem Cells. Am J Hematol. Jun. 2007;82(6): p. 463-472.
Bieback et al., Human Alternatives to Fetal Bovine Serum for the Expansion of Mesenchymal Stromal Cells from Bone Marrow. Stem Cells. Sep. 1, 2009;27(9): p. 2331-2341.
Blashki et al., Mesenchymal Stem Cells from Cortical Bone Demonstrate Increased Clonal Incidence, Potency, and Developmental Capacity Compared to their Bone Marrow-Derived Counterparts. J Tissue Eng, Aug. 1, 2016;7: p. 2041731416661196 in 14 pages.
Blazar et al., Successful Donor Cell Engraftment in a Recipient of Bone Marrow from a Cadaveric Donor. Blood 1986;67(6): p. 1655-1660.
Bork et al., DNA Methylation Pattern Changes Upon Long-term Culture and Aging of Human Mesenchymal Stromal Cells. Aging Cell, Feb. 2010;9(1): p. 54-63.
Brubaker et al., Tissue Recovery Practices and Bioburden: A Systemic Review. Cell Tissue Bank. Dec. 2016;17: 561-571.
Bruder et al., Growth Kinetics, Self-Renewal, and the Osteogenic Potential of Purified Human Mesenchymal Stem Cells During Extensive Subcultivation and Following Cryopreservation. J Cell Biochem, Feb. 1997;64(2): p. 278-294.
Busilacchi et al., A Novel Method to Evaluate Prethawing Viability of Cryopreserved CD34+ hematopoietic stem cells for autologous transplantation. J AABB. Transf. Jul. 2020;60(7): 1529-1535.
Chilima et al., Designing the Optimal Manufacturing Strategy for an Adherent Allogeneic Cell Therapy. BioProcess International, 2016;14(9): p. 24-32 https://bioprocessintl.com/manufacturing/cell-therapies/designing-optimal-manufacturing-strategy-adherent-allogeneic-cell-therapy/.
Chinnadurai et al., Immune dysfunctionality of replicative senescent mesenchymal stromal cells is corrected by IFNgamma priming. Blood Adv. Apr. 25, 2017;1(11): p. 628-643.
Choi et al., Dissecting Cellular Heterogeneity Using Single-Cell RNA Sequencing. Mol Cells. Mar. 3, 2019;42(3): p. 189-199.
ClinicalTrials.gov Identifier: NCT01459107 (2011).
ClinicalTrials.gov Identifier: NCT00497757 https://clinicaltrials.gov/cl2/show/NCT00497757l Ildstad, S.T.: Induction of donor Specific Tolerance in Recipients of Cardiac Allografts by Donor Stem Cell Infusion; Aug. 31, 2020, in 12 pages.
Cox et al., High Abundance of CD271+ Multipotential Stromal Cells (MSCs) in Intramedullary Cavities of Long Bones. Bone. Feb. 1, 2012;50(2): p. 510-517.
CRYO2018: The 55th Annual Meeting of the Society for Cryobiology. CSIC (2018) p. 1-2 Abstract.
CRYO2019: The 56th Annual Meeting of the Society for Cryobiology. CSIC (2019) p. 1-6 Abstracts.
Delloyd's Lab Tech. Standard Sieves and Mesh Sizes. Online publication. http://delloyd.50megs.com/moreinfo/mesh.html. pp. 2-3 (2018).
Dennis et al., The STRO-1+ Marrow Cell Population is Multipotential. Cells Tissues Organs, Jul. 1, 2002;170(2-3): p. 73-82.
DiGirolamo et al., Propagation and Senescence of Human Marrow Stromal Cells in Culture: A Simple Colony Forming Assay Identifies Samples with the Greatest Potential to Propagate and Differentiate. Br J Haematol. Nov. 1999; 107(2): p. 275-281.
Dominici et al., Minimal Criteria for Defining Multipotent Mesenchymal Stromal Cells: The international society for cellular therapy position statement. Cytotherapy, 2006. 8(4): p. 315-317.
Donnenberg et al., Clinical Implementation of a Procedure to Prepare Bone Marrow Cells from Cadaveric Vertebral Bodies. Regen Med. Nov. 2011;6(6): 701-706.
Donnenberg, PhD., Working with Bone Marrow on a Grand Scale McGowan Retreat, University of Pittsburgh Publication; Mar. 2011, 34 pages.
Du et al., Rational Design of a Fluorescent Hydrogen Peroxide Probe Based on the Umbelliferone Fluorophore. Tetrahedron Lett. May 5, 2008;49(19): 3045-3048.
Dykstra et al., Concise Review: Fat and Furious: Harnessing the Full Potential of Adipose-Derived Stromal Vascular Fraction. Stem Cells Transl Med. Apr. 2017;6(4): p. 1096-1108.
Eagle et al., Assessment of an Improved Bone Washing Protocol for Deceased Donor Human Bone. Cell Tissue Bank. Mar. 2015;16: p. 83-90.
Eckardt et al., Comparison of Engraftment and Acute GVHD in Patients Undergoing Cryopreserved or Fresh Allogeneic BMT. Bone Marrow Transplant, Feb. 1, 1993;11(2): p. 125-131.
Ferrari et al., Beta Regression for Modeling Rates and Proportions. J Appl Stat. Aug. 1, 2004;31(7): p. 799-815.
Ferrebee et al., The Collection, Storage and Preparation of Viable Cadaver Marrow for Intravenous Use. Blood. Feb. 1, 1959;14(2): 140-147.
Flood et al., Does Practice Make Perfect? Part I: The Relations Between Hospital Volume and Outcomes for Selected Diagnostic Categories. Med Care. Feb. 1, 1984;22(2): p. 98-114.
Flood et al., Does Practice Make Perfect? Part II: The Relation Between Volumes and Other Hospital Characteristics. Med Care. Feb. 1, 1984;22(2): p. 115-125.
Fresenius Kabi AG. 510(k) Summary. Bone Marrow Collection Stand. (2017) https://www.fda.gov/media/106490/download in 6 pages.
Fu et al., "Lymphohematopoietic graft-versus-host responses promote mixed chimerism in patients receiving intestinal transplantation," J Clin Invest. Apr. 21, 2021; 131(8):e141698 inn 16 pages; doi: 10.1172/JCI141698.
Galipeau et al., International Society for Cellular Therapy Perspective on Immune Functional Assaysfor Mesenchymal Stromal Cells as Potency Release Criterion for Advanced Phase Clinical Trials. Cytotherapy, Feb. 1, 2016;18(2): p. 151-159.
Galipeau et al., Mesenchymal Stromal Cells: Clinical Challenges and Therapeutic Opportunities. Cell Stem Cell, Jun. 1, 2018;22(6): p. 824-833.
GE Healthcare Life Sciences. Cell Separation Media Reference. 2014; 80 pages.
Gorantla et al., Development and Validation of a Procedure to Isolate Viable Bone Marrow Cells from the Vertebrae of Cadaveric Organ Donors for Composite Organ Grafting. Cytotherapy. Jan. 1, 2012;14(1): 104-113.
Gronthos et al., Molecular and cellular characterisation of highly purified stromal stem cells derived from human bone marrow. J Cell Sci. May 1, 2003;116(Pt 9): p. 1827-1835.
Han et al., Optimization of Human Umbilical Cord Mesenchymal Stem Cell Isolation and Culture Methods. Cytotechnology. Oct. 2013;65: 819-827.
Harrel Jr., Regression Modeling Strategies with Applications to Linear Models, Logistic Regression, and Survival Analysis. 2nd ed. Springer Series in Statistics. 2001, New York: Springer. 582.

(56) References Cited

OTHER PUBLICATIONS

Harrison et al., Cell Therapy-Processing Economics: Small-Scale Microfactories as a Stepping Stone Toward Large-Scale Macrofactories. Regen Med, Mar. 2018;13(2): p. 159-173.
Heathman et al., Characterization of Human Mesenchymal Stem Cells from Multiple Donors and the Implications for Large Scale Bioprocess Development. Biochem Eng J. Apr. 15, 2016;108: p. 14-23.
Hemacare Corporation. Isolation of Peripheral Blood Mononuclear Cells (PBMCs) Using a Density Gradient Reagent. Technical Protocol. PROT-IPBMC-V1 .1 1018 (2016).
Hibino et al., Comparison of Human Bone Marrow Mononuclear Cells Isolation Methods for Creating Tissue-Engineered Vascular Grafts: Novel Filter System Versus Traditional Density Centrifugation Method. Tissue Eng Part C: Methods. Oct. 1, 2011;17(10): 993-998.
Hotta et al., Long-term Nonhuman Primate Renal Allograft Survival Without Ongoing Immunosuppression in Recipients of Delayed Donor Bone Marrow Transplantation. Transplantation, Apr. 2018; 102(4): p. e128-e136.
Hunt C.J., Cryopreservation of Human Stem Cells for Clinical Application: A Review. Transfus Med Hemother. Mar. 16, 2011;38(2): 107-123.
Hwang et al., Single-cell RNA Sequencing Technologies and Bioinformatics Pipelines. Exp Mol Med. Aug. 2018; 50(8): p. 1-4.
Johnstone et al., Identification and Characterization of a Large Source of Primary Mesenchymal Stem Cells Tightly Adhered to Bone Surfaces of Human Vertebral Body Marrow Cavities. Cytotherapy. Nov. 1, 2020;(22)11:617-628.
Jones et al., Large-scale Extraction and Characterization of CD271+ Multipotential Stromal Cells from Trabecular Bone in Health and Osteoarthritis: Implications for Bone Regeneration Strategies Based on Uncultured or Minimally Cultured Multipotential Stromal Cells. Arthritis Rheum. Jul. 2010;62(7): p. 1944-1954.
Jossen et al., Manufacturing Human Mesenchymal Stem Cells at Clinical Scale: Process and Regulatory Challenges. Appl Microbial Biotechnol. May 2018;102(9): p. 3981-3994.
Kamble et al.: Orthotopic heart transplant facilitated autologous hematopoietic stem cell transplantation in light-chain amyloidosis. Blood Dec. 3, 2015; 126(23): 5364 Abstract in 2 pages.
Kawai et al., Long-term Results in Recipients of Combined HLA-Mismatched Kidney and Bone Marrow Transplantation Without Maintenance Immunosuppression. Am J Transplant, Jul. 1, 2014;14(7): p. 1599-611.
Kenyon et al., Effect of Depletion of Class II Bright Cells on the Immunogenicity and Stem Cell Content of Human Vertebral Body Bone Marrow. Transplant Proc. Dec. 1995;27(6):3419.
Knebel et al., Allocation of Scarce Resources after a Nuclear Detonation: Setting the Context. Disaster Med Public Health Prep, Mar. 2011;5(Suppl 1): p. S20-531.
Lechanteur et al., Large-scale Clinical Expansion of Mesenchymal Stem Cells in the GMP-Compliant, Closed Automated Quantum® Cell Expansion System: Comparison with Expansion in Traditional T-Flasks. Stem Cell Research & Therapy, 2014;4(8): p. 1-11.
Li et al., Therapeutic Delivery Specifications Identified Through Compartmental Analysis of a Mesenchymal Stromal Cell-Immune Reaction. Sci Rep, May 1, 2018;8(1): p. 6816 in 12 pages.
Linch et al., Bone Marrow Processing and Cryopreservation. J Clin Path. Feb. 1, 1982; 35(2): p. 186-190.
Lioznov et al., Transportation and Cryopreservation may Impair Haematopoietic Stem Cell Function and Engraftment of Allogeneic PBSCs, but not BM. Bone Marrow Transplant, Jul. 2008;42(2): p. 121-128.
Lipsitz et al., A Roadmap for Cost-of-Goods Planning to Guide Economic Production of Cell Therapy Products. Cytotherapy, Dec. 1, 2017;19(12): p. 1383-1391.
Lockhart et al., Use of Freshly Isolated Human Adipose Stromal Cells for Clinical Applications. Aesthet Surg J. Jul. 1, 2017; 37(suppl 3): p. S4-S8.
Long et al., Accumulation of CD11b+Gr-1+ Cells in the Lung, Blood and Bone Marrow of Mice Infected with Highly Pathogenic H5N1 and H1N1 Influenza Viruses. Arch Virol. Jun. 2013; 158: 1305-1322.
Mendicino et al., MSC-Based Product Characterization for Clinical Trials: an FDA Perspective. Cell Stem Cell, Feb. 6, 2014;14(2): p. 141-145.
Michalova et al., Hematopoietic Stem Cells Survive Circulation Arrest and Reconstitute Hematopoiesis in Myeloablated Mice. Biol Blood Marrow Transpl. Sep. 1, 2011;17(9): 1273-1281.
Miller et al., Phenotypic and Functional Equivalency of Digested Bone Marrow Mesenchymal Stem Cells to Aspirated Bone Marrow Mesenchymal Stem Cells. Faseb J. Apr. 2019;33(S1) (2019) Abstract.
Miltenyi Biotec. Isolation of Mononuclear Cells from Human Bone Marrow Aspirates by Density Gradient Centrifugation. 2008; 1 page.
Mizukami et al., Technologies for Large-Scale Umbilical Cord-Derived MSC Expansion: Experimental Performance and Cost of Goods Analysis. Biochem Eng J. Jul. 15, 2018;135: p. 36-48.
Moravcikova et al., Proteomic Profiling of Native Unpassaged and Culture-Expanded Mesenchymal Stromal Cells (MSC). Cytometry A, Sep. 2018;93(9): p. 894-904.
Morgenstern et al., Post-Thaw Viability of Cryopreserved Peripheral Blood Stem Cells (PBSC) does not Guarantee Functional Activity: Important Implications for Quality Assurance of Stem Cell Transplant Programmes. Br J Haematol. Sep. 2016; 174(6): p. 942-951.
Muraglia et al., Clonal Mesenchymal Progenitors from Human Bone Marrow Differentiate in vitro According to a Hierarchical Model. J Cell Sci. Apr. 1, 2000;113 ( Pt 7): p. 1161-1166.
Oetjen et al., Human Bone Marrow Assessment by Single-Cell RNA Sequencing, Mass Cytometry, and Flow Cytometry. JCI Insight. Dec. 12, 2018;3(23): e124928 in 9 pages.
Olsen et al., Peak MSC-Are We There Yet? Front Med (Lausanne), 2018. 5: p. 178.
Oseni et al., Optimization of Chondrocyte Isolation and Characterization for Large-Scale Cartilage Tissue Engineering. J Surg Res. May 1, 2013;181(1): 41-48.
Pennington et al., Evaluation of a Sterling Cycle Controlled Rate Freezing Device for Simultaneous Cryopreservation of Multiple Units. Cryobiology. 2019; 91:146-197—Abstract P36.
Pereira et al., Impact of Allogeneic Stem Cell Manufacturing Decisions on Cost of Goods, Process Robustness and Reimbursement. Biochem Engin J. Sep. 15, 2018;137: 132-151.
Picard et al., Cross-validation of regression models. J Am Stat Assoc. Sep. 1, 1984;79(428): p. 575-583.
Pittenger et al., Multilineage Potential of Adult Human Mesenchymal Stem Cells. Science. Apr. 2, 1999;284(5411): p. 143-147.
Quah et al., Monitoring Lymphocyte Proliferation in Vitro and in Vivo with the Intracellular Fluorescent Dye Carboxyfluorescein Diacetate Succinimidyl Ester. Nat Protoc. Sep. 2007;2(9): p. 2049-2056.
Redaelli et al., From Cytogenomic to Epigenomic Profiles: Monitoring the Biologic Behavior of in Vitro Cultured Human Bone Marrow Mesenchymal Stem Cells. Stem Cell Res Ther. Dec. 2012; 3(6): p. 1-7.
Rybka et al., Hematopoietic Progenitor Cell Content of Vertebral Body Marrow Used for Combined Solid Organ and Bone Marrow Transplantation. Transplantation. Mar. 3, 1995;59(6): 871-874.
Saegeman et al., Influence of Postmortem Time on the Outcome of Blood Cultures Among Cadaveric Tissue Donors. Eu J Clin Microbiol Infect Dis. Feb. 2009;28: 161-168.
Schneeberger et al., Upper-Extremity Transplantation Using a Cell-Based Protocol to Minimize Immunosuppression. Ann Surg. Feb. 2013;257(2): p. 345-351.
Schwartz et al., Explanatory and Pragmatic Attitudes in Therapeutical Trials. J Chronic Dis. Aug. 1, 1967; 20(8): p. 637-648.
Sherry et al., The Influence of Warm Ischemic Time on the Viability of Deceased Organ Donor Derived Bone Marrow. FASEB J. Apr. 2018;32(S1): in 5 pages.
Shu et al., Development of a Reliable Low-Cost Controlled Cooling Rate Instrument for the Cryopreservation of Hematopoietic Stem Cells. Cytotherapy Jan. 1, 2010;12(2): 161-169.

(56) References Cited

OTHER PUBLICATIONS

Siclari et al., Mesenchymal Progenitors Residing Close to the Bone Surface are Functionally Distinct from Those in the Central Bone Marrow. Bone. Apr. 1, 2013;53(2): p. 575-586.
Simaria et al., Allogeneic Cell Therapy Bioprocess Economics and Optimization: Single-Use Cell Expansion Technologies. Biotechnol Bioeng. Jan. 2014;111(1): p. 69-83.
Simmons et al., Identification of Stromal Cell Precursors in Human Bone Marrow by a Novel Monoclonal Antibody, STRO-1. Blood. 1991. 78(1): p. 55-62.
Soderdahl et al., Cadaveric Bone Marrow and Spleen Cells for Transplantation. Bone Marrow Transpl. Jan. 1998;21(1): 79-84.
Spitzer et al., Twenty Year Follow Up of Histocompatibility Leukocyte Antigen-Matched Kidney and Bone Marrow Co-Transplantation for Multiple Myeloma with End Stage Renal Disease: Lessons Learned. Transplantation. Nov. 2019;103(11): p. 2366-2372.
Squillaro et al., Clinical Trials With Mesenchymal Stem Cells: An Update. Cell Transplant. May 2016; 25(5): p. 829-848.
Stenn et al., Dispase, a Neutral Protease From Bacillus Polymyxa, Is a Powerful Fibronectinase and Type IV Collagenase. J Invest Dermatol. Aug. 1, 1989;93(2): p. 287-290.
Stockschläder et al., Use of Cryopreserved Bone Marrow in Allogeneic Bone Marrow Transplantation. Bone Marrow Transplant. 1995 15(4): p. 569-72.
Stockschläder et al., Use of Cryopreserved Bone Marrow in Unrelated Allogeneic Transplantation. Bone Marrow Transplant. Feb. 1, 1996; 17(2): p. 197-199 (Abstract).
Stockschläder et al., Long-term Follow-up of Leukemia Patients After Related Cryopreserved Allogeneic Bone Marrow Transplantation. Br J Haematol. Feb. 1997;96(2): p. 382-386.
Suire et al., Isolation of the Stromal-Vascular Fraction of Mouse Bone Marrow Markedly Enhances the Yield of Clonogenic Stromal Progenitors. Blood. Mar. 15, 2012;119(11): e86-95.
Sutherland et al., The Ishage Guidelines for CD34+ Cell Determination by Flow Cytometry. J Hematother, 1996;5(3): p. 213-226.
Thomas et al., Intravenous Infusion of Bone Marrow in Patients Receiving Radiation and Chemotherapy. N Engl J Med. Sep. 12, 1957;257(11): p. 491-496.
Thompson M.C., Preparing Skeletons for Research and Teaching from Preserved Human Specimens. Thesis California State University, Dec. 2015; 162 pages.
Thompson et al., Time and Temperature Dependent Ficoll Separation of Aged Whole Blood Neutrophils. Faseb J. 2019 33(S1) Abstract (2019).
Urso et al., Short-Term Preservation of Mouse Bone Marrow at Refrigeration and Room Temperature for Irradiation Experiments. J Appl Physio. Mar. 1, 1957;10(2): 314-316.
Walter et al.: Molecular and Functional Phenotypes of Human Bone Marrow-Derived Mesenchymal Stromal Cells Depend on Harvesting Techniques. Int J Mol Sci. Jun. 19, 2020;21(12): 4382 in 12 pages.
Warwick et al., Collagenase Clostridium Histolyticum: Emerging Practice Patterns and Treatment Advances. J Plastic Surg Hand Surg.Sep. 2, 2016;50(5): p. 251-326.
Weinstock et al., Radiologic and Nuclear Events: Contingency Planning for Hematologists/Oncologists. Blood. Jun. 15, 2008;111(12): p. 5440-5445.
Woods et al., The Learning Curve and the Cost of Heart Transplantation. Health Sery Res. Jun. 1992;27(2): p. 219-238.
Woods et al., Packaging Considerations for Biopreservation. Transfus Med Hemother. Mar. 16, 2011;38(2): 149-156.
Woods et al., Off the Shelf Cellular Therapeutics: Factors to Consider During Cryopreservation and Storage of Human Cells for Clinical Use. Cytotherapy. Jun. 1, 2016;18(6): p. 697-711.
Woods et al., Ischemia Considerations for the Development of an Organ and Tissue Donor Derived Bone Marrow Bank. J Transl Med. Dec. 18, 2020(1): 300 in 11 pages.
Wuchter et al., Standardization of Good Manufacturing Practice—Compliant Production of Bone Marrow-Derived Human Mesenchymal Stromal Cells for Immunotherapeutic Applications. Cytotherapy. Feb. 1, 2015;17(2): p. 128-139.
Yamada et al., Overcoming Memory T-cell Responses for Induction of Delayed Tolerance in Nonhuman Primates. Am J Transplant. Feb. 1, 2012;12(2): p. 330-340.
Yusop et al., Isolation and Characterisation of Mesenchymal Stem Cells from Rat Bone Marrow and the Endosteal Niche: A Comparative Study. Stem Cells Int. Mar. 22, 2018; p. 6869128 in 14 pages.
International Search Report and Written Opinion for International Application No. PCT/US2022/013541 dated Apr. 26, 2022.
Breite et al.: Characterization and functional assessment of class I (C1) collagenases and the synergistic degradation of native collagen in enzyme mixtures containing class II (C2) collagenase. In Transplantation Proceedings Nov. 1, 2011 (vol. 43, No. 9, pp. 3171-3175).
Chiang et al., Allogeneic Mesenchymal Stem Cells in Combination with Hyaluronic Acid for the Treatment of Osteoarthritis in Rabbits. PLoS One. Feb. 25, 2016; 11(2): e149835 in 15 pages.
Chilima et al., Impact of Allogeneic Stem Cell Manufacturing Decisions on Cost of Goods, Process Robustness and Reimbursement. Biochem Engin J. Sep. 15, 2018;137: p. 132-151.
Donnenberg A.D. PhD., Declaration Under 37 C.F.R. 1.132, dated Aug. 11, 2021 including Biography, submitted in U.S. Appl. No. 17/013,395, filed Sep. 4, 2020 in 78 pages.
Fragkakis et al.: Vertebral body versus iliac crest bone marrow as a source of multipotential stromal cells: Comparison of processing techniques, tri-lineage differentiation and application on a scaffold for spine fusion. PloS One. May 24, 2018;13(5): e0197969 in 20 pages.
Fuller et al., Applications and Optimization of Cryopreservation Technologies to Cellular Therapeutics, Cell Gene Thera Insights, Jun. 6, 2017; 3(5): 359-378.
Ghaneialvar et al.: Characterization and classification of mesenchymal stem cells in severeal species using markers for cell therapy purposes. Indian J Clin Biochem. Jan. 2018;33: 46-52.
Gorantla et al.: 2007-05-R11A Procedure for preparation of bone marrow cells from cadaveric vertebral bodies. University of Pittsburgh Medical Center. pp. 1-11 (2007).
Guan et al., Comparison of biological characteristics of mesenchymal stem cells derived from the human umbilical cord and decidua parietalis, Mol Med Rep. (2019); 20(1): 633-639.
Haitao et al., Progress in Bone Marrow Stem Cell Transplantation for the Treatment of Ischemic Cardiomyopathy. Tissue Engineering Research and Clinical Rehabilitation. Oct. 21, 2007; vol. 11, No. 42, 8565-8568.
Halfon et al.: Markers distinguishing mesenchymal stem cells from fibroblasts are downregulated with passaging. Stem Cells Devel. Jan. 1, 2011;20(1): 53-66.
Johnstone et al.: A large-scale bank of organ donor bone marrow and matched mesenchymal stem cells for promoting immunomodulation and transplant tolerance. Front Immunol. Feb. 26, 2021;12:622604 in 11 pages.
McCarthy et al., Tissue dissociation enzymes for isolating human islets for transplantation: factors to consider in setting enzyme acceptance criteria, Transplantation. Jan. 27, 2011;91(2): 137-145.
Michalova et al., Cadaveric Bone Marrow as Potential Source of Hematopoietic Stem Cells for Transplantation. Chimerism Jul. 20, 2011;2(3): p. 86-87.
Nasca et al., “Use of Cryopreserved Bone in Spinal Surgery,” Spine. Apr. 1, 1987;12(3): 222-227.
Schneeberger et al., 2007-05-R11A Procedure for preparation of bone marrow cells from cadaveric vertebral bodies, Regen Med. NIHMS339821—Supplement p. 1-11 (2014).
Zhan et al.: A comparative study of biological characteristics and transcriptome profiles of mesenchymal stem cells from different canine tissues. Int J Mol Scienc. Mar. 25, 2019;20(6): 1485 in 16 pages.
International Search Report and Written Opinion dated Sep. 16, 2020 in Application No. PCT/US2020/025778.

(56) References Cited

OTHER PUBLICATIONS

International Search Report and Written Opinion for International Application No. PCT/US2021/042064 dated Oct. 26, 2021.
International Search Report and Written Opinion for International Application No. PCT/US2021/055066 dated Dec. 23, 2021.
International Search Report and Written Opinion for International Application No. PCT/US2021/055081 dated Jan. 20, 2022 in 13 pages.
International Search Report and Written Opinion for International Application No. PCT/US2021/064152 dated Mar. 30, 2022.
European Extended Search Report for Application No. 21907934.0 dated Dec. 2, 2024.
Hefley, "Utilization of FPLC-Purified Bacterial Collagenase for the Isolation of Cells from Bone", Journal of Bone and Mineral Research (ASBMR 30th Annual Meeting), Blackweel Science, Inc., Jan. 1, 1987, vol. 2, No. 6, pp. 505-516.
Johnstone, Edit Identification and Characterization of a Large Source of Primary Mesenchymal Stem Cells Tightly Adhered to Bone Surfaces of Human Vertebral Body Marrow Cavities. ISSCR Abstract (2020).

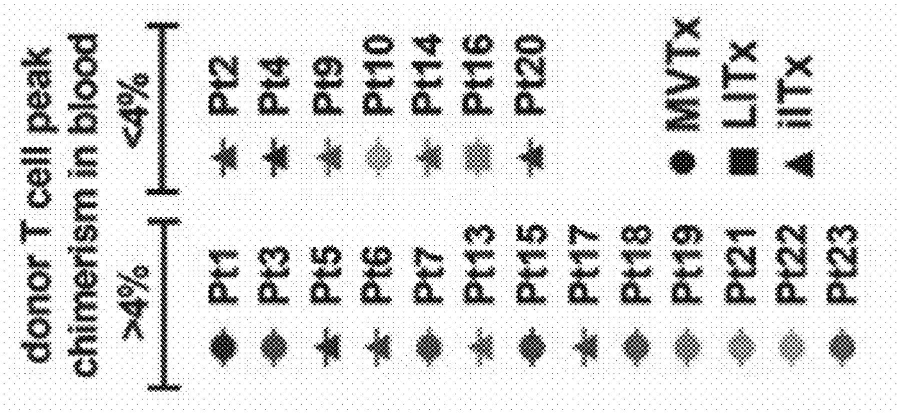
FIG. 1B
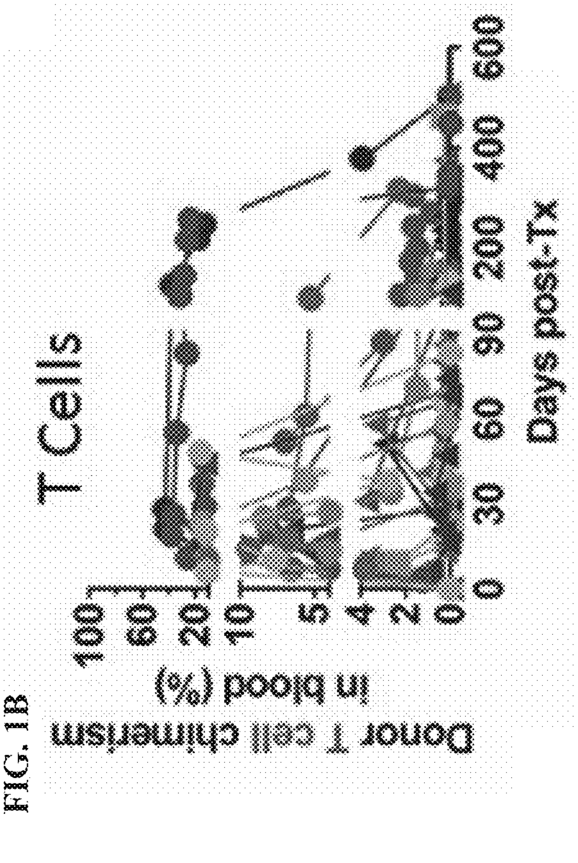
FIG. 1C
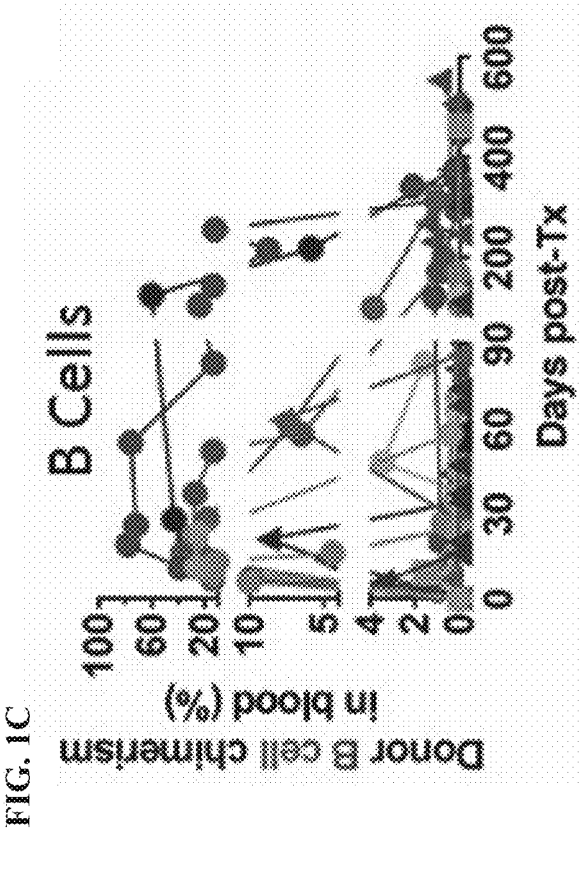

METHODS OF CELL THERAPIES

CROSS-REFERENCE TO RELATED APPLICATIONS

This application is a continuation of U.S. patent application Ser. No. 17/696,779, filed Mar. 16, 2022, which is a continuation of International Application No. PCT/US2021/064152, filed Dec. 17, 2021, which claims the benefit of U.S. Provisional Application No. 63/127,949, filed Dec. 18, 2020. Each of the aforementioned patent applications is incorporated herein by reference in its entirety.

STATEMENT AS TO FEDERALLY SPONSORED RESEARCH

This invention was made with government support under AI129444 awarded by the National Institutes of Health. The government has certain rights in the invention.

INCORPORATION BY REFERENCE

All publications, patents, and patent applications mentioned in this specification are herein incorporated by reference to the same extent as if each individual publication, patent, or patent application was specifically and individually indicated to be incorporated by reference.

Fu, Jianing et al., (2021) Lymphohematopoietic graft-versus-host responses promote mixed chimerism in patients receiving intestinal transplantation, J Clin Invest. 2021; 131(8):e141698. https://doi.org/10.1172/JCI141698 is incorporated herein by reference in its entirety.

BACKGROUND

Abdominal trauma, congenital abnormalities, ischemic injury, or diseases or disorders of the digestive system cause damage and prevent digestion and absorption of fluids and nutrients. Organ transplantation such as intestinal transplantation can be one of the select few therapeutic options for subjects afflicted with the aforementioned conditions. However, rejection of the transplanted organ is a significant challenge to overcome.

SUMMARY

The present application addresses methods for overcoming the significant challenges associated with organ transplantation. An aspect of the present disclosure is a method of establishing a mixed chimerism, establishing a T-cell macrochimerism of at least about 4%, preventing a host-versus-graft response, and/or preventing a rejection of a donor organ in a subject wherein the subject has received an organ transplant, the method comprising administering to the subject a population of CD34+ cells. In some embodiments, the population of CD34+ cells comprises at least about 1×10^6 CD34+ cells per kilogram of the subject. In some embodiments, administering to the subject the population of CD34+ cells occurs about 1 to about 30 days after the organ transplant. In some embodiments, administering to the subject the population of CD34+ cells occurs about 11 to about 13 days after the organ transplant. In some embodiments, the organ transplant comprises an intestine transplant, a liver transplant, a stomach transplant, or any combination thereof. In some embodiments, the organ transplant comprises a multivisceral transplant comprising transplantation of two or more of stomach, pancreas, liver, small intestine, large intestine, and kidney. In some embodiments, the organ transplant comprises an organ that comprises a population of hematopoietic stem cells or hematopoietic progenitor stem cells. In some embodiments, the population of CD34+ cells is selected for such that the population of CD34+ cells comprises no more than about 1×10^4 CD3+ cells per kilogram of the subject. In some embodiments, the population of CD34+ cells is derived from a cadaver. In some embodiments, the population of CD34+ cells comprises at least about 2×10^6 CD34+ cells per kilogram of the subject. In some embodiments, the population of CD34+ cells comprises at least about 3×10^6 CD34+ cells per kilogram of the subject. In some embodiments, the population of CD34+ cells comprises CD34+ cells that are HLA-matched to the organ transplant. In some embodiments, the population of CD34+ cells are obtained from the same person as the donor organ. In some embodiments, the population of CD34+ cells are not obtained from the same person as the donor organ. In some embodiments, the method further comprises administering rabbit anti-thymocyte globulin to the subject. In some embodiments, the rabbit anti-thymocyte globulin is administered on the day of the organ transplant, 1 day after the organ transplant, 2 days after the organ transplant, and/or 3 days after the organ transplant and at a dose of from about 1.5 mg to about 9 mg per kilogram of the subject. In some embodiments, the rabbit anti-thymocyte globulin is administered 3 days after the organ transplant and at a dose of up to about 9 mg per kilogram of the subject, thereby reducing circulating CD4+ T cell concentrations below 50/μl. In some embodiments, the method further comprises administering one or more corticosteroids to the subject. In some embodiments, the one or more corticosteroids comprise prednisone. In some embodiments, the one or more corticosteroids are administered on the day of the organ transplant, 1 day after the organ transplant, 2 days after the organ transplant, 3 days after the organ transplant, 4 days after the organ transplant, 5 days after the organ transplant, and/or 6 days after the organ transplant. In some embodiments, the one or more corticosteroids are administered for about 6 to about 12 months after the organ transplant. In some embodiments, the method further comprises administering Tacrolimus (Prograf®) to the subject. In some embodiments, the Tacrolimus is administered one day after the organ transplant. In some embodiments, the Tacrolimus is administered to the subject daily. In some embodiments, the Tacrolimus is administered from about 3 ng/ml to about 15 ng/ml and, optionally, maintained at trough levels of 10-15 ng/ml for the first month, 8-12 ng/ml for the second through sixth month, 5-10 ng/ml for the remainder of the first year, and/or 3-7 ng/ml at one or more time points after the first year. In some embodiments, the administration of Tacrolimus and/or the administration of the one or more corticosteroids in a subsequent administration is tapered relative to the first administration. In some embodiments, the administration of Tacrolimus and/or the administration of the one or more corticosteroids are tapered one year after the organ transplant. In some embodiments, the administration of Tacrolimus is tapered by 25% one year after the organ transplant. In some embodiments, the administration of Tacrolimus is tapered by 50% about 380 to about 395 days after the organ transplant. In some embodiments, the administration of the one or more corticosteroids is tapered to discontinuation beginning about 1 year after the organ transplant. In some embodiments, administering to the subject the population of CD34+ cells does not result in a Grade II or greater graft-versus-host disease within a month, within a year, or within three years after the organ transplant.

In some embodiments, the method further comprises administering one or more mTOR inhibitors to the subject. In some embodiments, the method further comprises tapering the administration of the one or more mTOR inhibitors to the subject in a subsequent administration relative to the first administration.

Another aspect of the present disclosure is a method of generating donor derived T cells in an organ transplant recipient, the method comprising administering bone marrow stem cells to the organ transplant recipient about 1 to about 30 days after the organ transplant recipient receives one or more organ transplants. In some embodiments, the bone marrow stem cells are derived from a cadaver. In some embodiments, the bone marrow stem cells comprise a population of CD34+ cells. In some embodiments, administering to the subject the population of CD34+ cells occurs about 11 to about 13 days after the one or more organ transplants. In some embodiments, the one or more organ transplants comprises an intestine transplant, a liver transplant, a stomach transplant, or any combination thereof. In some embodiments, the one or more organ transplants comprises a multivisceral transplant comprising transplantation of two or more of stomach, pancreas, liver, small intestine, large intestine, and kidney. In some embodiments, the population of CD34+ cells is selected for such that the population of CD34+ cells comprises no more than about 1×10^4 CD3+ cells per kilogram of the subject. In some embodiments, the population of CD34+ cells comprises at least about 2×10^6 CD34+ cells per kilogram of the subject. In some embodiments, the population of CD34+ cells comprises at least about 3×10^6 CD34+ cells per kilogram of the subject. In some embodiments, the population of CD34+ cells comprises CD34+ cells that are HLA-matched to the one or more organ transplants.

In methods of the present disclosure, an organ transplant recipient is administered bone marrow stem cells comprising immune cells, hematopoietic stem cells, and/or hematopoietic progenitor cells (e.g. CD34+ cells). Some of the immune cells, hematopoietic stem cells, or hematopoietic progenitor cells survive and enter the bone marrow of the recipient. This process is facilitated by a lymphohematopoietic graft-vs-host responses (LGvHR), in which T lymphocytes from the administrated bone marrow stem cells attack recipient blood-forming cells to make "space" for their own establishment in the bone marrow, but do not induce graft-versus-host disease (GvHD). This immune response suppresses rejection of the transplanted organ.

In some embodiments, the bone marrow stem cells (which include immune cells, hematopoietic stem cells, and hematopoietic progenitor cells) are derived from a cadaver (e.g. cadaveric CD34+ cells) and are administered to a subject who has received and organ transplant.

In some embodiments, donor bone marrow cells can be infused when LGvHR is maximal in the subject, resulting in a long-term mixed chimerism and increased tolerance. In some embodiments, the donor bone marrow cells can be infused when LGvHR is maximal in the subject, resulting in a permanent chimerism and complete immunosuppression withdrawal (i.e., tolerance). In some embodiments, the donor bone marrow cells infusion can be administered without risk of GvHD. In some embodiments, the donor is a cadaver.

An aspect of the present disclosure comprises a method of establishing a long-term mixed chimerism in a subject wherein said subject has received an organ transplant, the method comprising: administering to said subject a population of CD34+ cells. In some embodiments, said population of CD34+ cells comprises at least 1×10^6 CD34+ cells per kilogram of said subject. In some embodiments, the administering of the population of the CD34+ cells occurs about 1 to about 30 days after said organ transplant. In some embodiments, the administering of the population of the CD34+ cells occurs about 11 to about 13 days after said organ transplant. In some embodiments, said organ transplant comprises the transplantation of a plurality of organs. In some embodiments, said organ transplant comprises a multivisceral transplant. In some embodiments, said organ transplant comprises an intestine transplant. In some embodiments, said organ transplant comprises an organ wherein said organ comprises a population of hematopoietic stem cells or hematopoietic progenitor stem cells. In some embodiments, said population of CD34+ cells comprises no more than 1×10^4 CD34+ cells. In some embodiments, said population of CD34+ cells is derived from a cadaver. In some embodiments, said population of CD34+ cells comprises at least 2×10^6 CD34+ cells per kilogram of said subject. In some embodiments, said population of CD34+ cells comprises at least 3×10^6 CD34+ cells per kilogram of said subject. In some embodiments, said population of CD34+ cells comprises CD34+ cells that are HLA-matched to said organ transplant. In some embodiments, said population of CD34+ cells comprises CD34+ cells derived from a donor wherein said organ transplant is derived from said donor. In some embodiments, the method further comprises administering rabbit anti-thymocyte globulin to said subject. In some embodiments, said rabbit anti-thymocyte globulin is administered on the day of said organ transplant, 1 day after said organ transplant, 2 days after said organ transplant, and/or 3 days after said organ transplant. In some embodiments, said rabbit anti-thymocyte globulin is administered at a dose of about 1.5 mg to about 9 mg per kilogram of said subject. In some embodiments, the method further comprises administering one or more corticosteroids to said subject. In some embodiments, said one or more corticosteroids comprise prednisone. In some embodiments, said one or more corticosteroids are administered on the day of said organ transplant, 1 day after said organ transplant, 2 days after said organ transplant, 3 days after said organ transplant, 4 days after said organ transplant, 5 days after said organ transplant, and/or 6 days after said organ transplant. In some embodiments, said one or more corticosteroids are administered for about 6 to about 12 months after said organ transplant. In some embodiments, the method further comprises administering Tacrolimus (Prograf®) to said subject. In some embodiments, said Tacrolimus is administered one day after said organ transplant. In some embodiments, said Tacrolimus is administered to said subject daily. In some embodiments, said Tacrolimus is administered at about 3 ng/ml to about 15 ng/ml. In some embodiments, said administration of Tacrolimus and/or said administration of said one or more corticosteroids are tapered. In some embodiments, said administration of Tacrolimus and/or said administration of said one or more corticosteroids are tapered one year after said organ transplant. In some embodiments, said administration of Tacrolimus is tapered by 25% one year after said organ transplant. In some embodiments, said administration of Tacrolimus is tapered by 50% about 380 to about 395 days after said organ transplant. In some embodiments, said administration of said one or more corticosteroids is tapered to discontinuation. In some embodiments, the administering of the population of the CD34+ cells does not result in a Grade II or greater graft-versus-host disease. In some embodiments, the administering of the population of the CD+34 cells promotes long-term multilineage macrochimerism and induces tolerance.

Another aspect of the present disclosure comprises a method of establishing a T-cell macrochimerism of at least 4% in a subject wherein said subject has received an organ transplant, the method comprising administering to said subject a population of CD34+ cells. In some embodiments, said population of CD34+ cells comprises at least 1×10^6 CD34+ cells per kilogram of said subject. In some embodiments, the administering of the population of the CD34+ cells occurs about 1 to about 30 days after said organ transplant. In some embodiments, the administering of the population of the CD34+ cells occurs about 11 to about 13 days after said organ transplant. In some embodiments, said organ transplant comprises the transplantation of a plurality of organs. In some embodiments, said organ transplant comprises a multivisceral transplant. In some embodiments, said organ transplant comprises an intestine transplant. In some embodiments, said organ transplant comprises an organ wherein said organ comprises a population of hematopoietic stem cells or hematopoietic progenitor stem cells. In some embodiments, said population of CD34+ cells comprises no more than 1×10^4 CD34+ cells. In some embodiments, said population of CD34+ cells is derived from a cadaver. In some embodiments, said population of CD34+ cells comprises at least 2×10^6 CD34+ cells per kilogram of said subject. In some embodiments, said population of CD34+ cells comprises at least 3×10^6 CD34+ cells per kilogram of said subject. In some embodiments, said population of CD34+ cells comprises CD34+ cells that are HLA-matched to said organ transplant. In some embodiments, said population of CD34+ cells comprises CD34+ cells derived from a donor wherein said organ transplant is derived from said donor. In some embodiments, the method further comprises administering rabbit anti-thymocyte globulin to said subject. In some embodiments, said rabbit anti-thymocyte globulin is administered on the day of said organ transplant, 1 day after said organ transplant, 2 days after said organ transplant, and/or 3 days after said organ transplant. In some embodiments, said rabbit anti-thymocyte globulin is administered at a dose of about 1.5 mg to about 9 mg per kilogram of said subject. In some embodiments, the method further comprises administering one or more corticosteroids to said subject. In some embodiments, said one or more corticosteroids comprise prednisone. In some embodiments, said one or more corticosteroids are administered on the day of said organ transplant, 1 day after said organ transplant, 2 days after said organ transplant, 3 days after said organ transplant, 4 days after said organ transplant, 5 days after said organ transplant, and/or 6 days after said organ transplant. In some embodiments, said one or more corticosteroids are administered for about 6 to about 12 months after said organ transplant. In some embodiments, the method further comprises administering Tacrolimus (Prograf®) to said subject. In some embodiments, said Tacrolimus is administered one day after said organ transplant. In some embodiments, said Tacrolimus is administered to said subject daily. In some embodiments, said Tacrolimus is administered at about 3 ng/ml to about 15 ng/ml. In some embodiments, said administration of Tacrolimus and/or said administration of said one or more corticosteroids are tapered. In some embodiments, said administration of Tacrolimus and/or said administration of said one or more corticosteroids are tapered one year after said organ transplant. In some embodiments, said administration of Tacrolimus is tapered by 25% one year after said organ transplant. In some embodiments, said administration of Tacrolimus is tapered by 50% about 380 to about 395 days after said organ transplant. In some embodiments, said administration of said one or more corticosteroids is tapered to discontinuation. In some embodiments, the administering of the population of the CD34+ cells does not result in a Grade II or greater graft-versus-host disease. In some embodiments, the administering of the population of the CD+34 cells promotes long-term multilineage macrochimerism and induces tolerance. In some embodiments, the population of CD34+ cells are obtained from the same person as the donor organ. In some embodiments, the population of CD34+ cells are not obtained from the same person as the donor organ.

Another aspect of the present disclosure comprises a method of establishing a chimerism of at least 1% in a subject wherein said subject has received an organ transplant, the method comprising: administering to said subject a population of CD34+ cells. In some embodiments, said population of CD34+ cells comprises at least 1×10^6 CD34+ cells per kilogram of said subject. In some embodiments, the administering of the population of the CD34+ cells occurs about 1 to about 30 days after said organ transplant. In some embodiments, the administering of the population of the CD34+ cells occurs about 11 to about 13 days after said organ transplant. In some embodiments, said organ transplant comprises the transplantation of a plurality of organs. In some embodiments, said organ transplant comprises a multivisceral transplant. In some embodiments, said organ transplant comprises an intestine transplant. In some embodiments, said organ transplant comprises an organ wherein said organ comprises a population of hematopoietic stem cells or hematopoietic progenitor stem cells. In some embodiments, said population of CD34+ cells comprises no more than 1×10^4 CD34+ cells. In some embodiments, said population of CD34+ cells is derived from a cadaver. In some embodiments, said population of CD34+ cells comprises at least 2×10^6 CD34+ cells per kilogram of said subject. In some embodiments, said population of CD34+ cells comprises at least 3×10^6 CD34+ cells per kilogram of said subject. In some embodiments, said population of CD34+ cells comprises CD34+ cells that are HLA-matched to said organ transplant. In some embodiments, the population of CD34+ cells are obtained from the same person as the donor organ. In some embodiments, the population of CD34+ cells are not obtained from the same person as the donor organ. In some embodiments, the method further comprises administering rabbit anti-thymocyte globulin to said subject. In some embodiments, said rabbit anti-thymocyte globulin is administered on the day of said organ transplant, 1 day after said organ transplant, 2 days after said organ transplant, and/or 3 days after said organ transplant. In some embodiments, said rabbit anti-thymocyte globulin is administered at a dose of about 1.5 mg to about 9 mg per kilogram of said subject. In some embodiments, the method further comprises administering one or more corticosteroids to said subject. In some embodiments, said one or more corticosteroids comprise prednisone. In some embodiments, said one or more corticosteroids are administered on the day of said organ transplant, 1 day after said organ transplant, 2 days after said organ transplant, 3 days after said organ transplant, 4 days after said organ transplant, 5 days after said organ transplant, and/or 6 days after said organ transplant. In some embodiments, said one or more corticosteroids are administered for about 6 to about 12 months after said organ transplant. In some embodiments, the method further comprises administering Tacrolimus (Prograf®) to said subject. In some embodiments, said Tacrolimus is administered one day after said organ transplant. In some embodiments, said Tacrolimus is administered to said subject daily. In some embodiments, said Tacrolimus is administered at about 3 ng/ml to about 15 ng/ml. In some embodiments, said administration of Tacrolimus and/or said administration of said one or more corticosteroids are tapered. In some embodiments, said administration of Tacrolimus and/or said administration of said one or more corticosteroids are tapered one year after said organ transplant. In some embodiments, said administration of Tacrolimus is tapered by 25% one year after said organ transplant. In some embodiments, said administration of Tacrolimus is tapered by 50% about 380 to about 395 days after said organ transplant. In some embodiments, said administration of said one or more corticosteroids is tapered to discontinuation. In some embodiments, the administering of the population of the CD34+ cells does not result in a Grade II or greater graft-versus-host disease. In some embodiments, the administering of the population of the CD+34 cells promotes long-term multilineage macrochimerism and induces tolerance.

Another aspect described herein is a method of preventing a rejection of a donor organ in a recipient, the method comprising: administering to said recipient a population of CD34+ cells. In some embodiments, said population of CD34+ cells comprises at least 1×10^6 CD34+ cells per kilogram of said recipient. In some embodiments, the administering of the population of the CD34+ cells occurs about 1 to about 30 days after an organ transplant to said recipient. In some embodiments, the administering of the population of the CD34+ cells occurs about 11 to about 13 days after said organ transplant to said recipient. In some embodiments, said organ transplant comprises the transplantation of a plurality of organs. In some embodiments, said organ transplant comprises a multivisceral transplant. In some embodiments, said organ transplant comprises an intestine transplant. In some embodiments, said organ transplant comprises an organ wherein said organ comprises a population of hematopoietic stem cells or hematopoietic progenitor cells. In some embodiments, said population of CD34+ cells comprises no more than 1×10^4 CD34+ cells. In some embodiments, said population of CD34+ cells is derived from a cadaver. In some embodiments, said population of CD34+ cells comprises at least 2×10^6 CD34+ cells per kilogram of said recipient. In some embodiments, said population of CD34+ cells comprises at least 3×10^6 CD34+ cells per kilogram of said recipient. In some embodiments, said population of CD34+ cells comprises CD34+ cells that are HLA-matched to said organ transplant. In some embodiments, said population of CD34+ cells comprises CD34+ cells derived from said donor. In some embodiments, the method further comprises administering rabbit anti-thymocyte globulin to said recipient. In some embodiments, said rabbit anti-thymocyte globulin is administered on the day of said organ transplant, 1 day after said organ transplant, 2 days after said organ transplant, and/or 3 days after said organ transplant. In some embodiments, said rabbit anti-thymocyte globulin is administered at a dose of about 1.5 mg to about 9 mg per kilogram of said recipient. In some embodiments, the method further comprises administering one or more corticosteroids to said recipient. In some embodiments, said one or more corticosteroids comprise prednisone. In some embodiments, said one or more corticosteroids are administered on the day of said organ transplant, 1 day after said organ transplant, 2 days after said organ transplant, 3 days after said organ transplant, 4 days after said organ transplant, 5 days after said organ transplant, and/or 6 days after said organ transplant. In some embodiments, said one or more corticosteroids are administered for about 6 to about 12 months after said organ transplant. In some embodiments, the method further comprises administering Tacrolimus (Prograf®) to said recipient. In some embodiments, said Tacrolimus is administered one day after said organ transplant. In some embodiments, said Tacrolimus is administered to said recipient daily. In some embodiments, said Tacrolimus is administered at about 3 ng/ml to about 15 ng/ml. In some embodiments, said administration of Tacrolimus and/or said administration of said one or more corticosteroids are tapered. In some embodiments, said administration of Tacrolimus and/or said administration of said one or more corticosteroids are tapered one year after said organ transplant. In some embodiments, said administration of Tacrolimus is tapered by 25% one year after said organ transplant. In some embodiments, said administration of Tacrolimus is tapered by 50% about 380 to about 395 days after said organ transplant. In some embodiments, said administration of said one or more corticosteroids is tapered to discontinuation. In some embodiments, the administering of the population of the CD34+ cells does not result in a Grade II or greater graft-versus-host disease. In some embodiments, the administering of the population of the CD+34 cells promotes long-term multilineage macrochimerism and induces tolerance, e.g., of an organ transplant.

BRIEF DESCRIPTION OF THE DRAWINGS

FIG. 1A-1E illustrates donor-derived multilineage long-term hematopoiesis in blood after intestine transplantation (ITx), especially in multivisiceral transplantation (MVTx) recipients. Example of staining is shown in FIG. 1A. Chimerism in each lineage over time is shown in FIG. 1B-1E. Each symbol type represents an individual patent. Circles indicate MVTx recipients, triangles indicate isolated intestine transplantation (iITx) recipients, and squares indicate liver and intestine transplant (LITx) recipients.

FIG. 9A illustrates percentages of donor CD34+ T cells among total CD45+ cells in recipient bone marrow of the indicated subjects at the indicated times post-transplantation. FIG. 9B illustrates percentages of donor CD34+ cells among total CD45+ cells in recipient bone marrow of the indicated subjects at the indicated times. FIG. 9C illustrates cumulative frequency of TCR sequences identifiable as GvH-reactive (from pre-transplant donor-anti-host MLR) as a percentage of the total number of unique sequences mappable to the pre-transplant donor T cell pool. Circles represent MvTx recipients and triangles represent ilTx recipients.

FIG. 10A-10D illustrate the sums of GvH or HvG clonal frequencies among total TCR templates in undigested biopsy specimens are shown at the indicated time points. Groups I-IV were defined by the presence of macrochimerism and DSA and by donor age ≥ or <1. FIG. 10E illustrates areas under the curve (AUCs) were calculated and normalized for duration of follow-up. $^{*}p<0.05$, $^{**}p<0.01$ by Mann-Whitney test.

FIG. 15A illustrates that six clusters were identified based on gene expression as shown in the upper UMAP panel, among FACS-sorted recipient HLA+ CD45+ CD3+ T cells from ileal biopsy taken on POD1194. Lower panel of UMAP shows location on these plots of HvG-reactive and known non-HvG-reactive CD4 and CD8 T cells and of T cells that were unmappable ("Un") to the pretransplant recipient T cell repertoire. FIG. 15B illustrates expression of representative genes known to be upregulated (CD69, CXCR6, and CA10) or downregulated (KLF2, SiPR1, and CCR7) in TRM and their projections on UMAP. Log fold changes (LogFC) FIG. 15C and heatmap (FIG. 15D) of the expression of selected genes related to TRM (CD69, KLF2, CD28, and CCR7) and Teff cytokines (IFNG, IL17A, IL22, and TNF) are shown between CD4 HvG (n=34) and CD4 non-HvG (n=24) cells.

FIG. 16A-16B illustrates comparison of numbers of clones defined as HvG-reactive (via CDR3 sequencing of pre-transplant MLR vs unstimulated recipient T cells) in: FIG. 16A: graft biopsies at time of rejection (medium gray) and after resolution of rejection (light gray) and pre-transplant lymphoid tissues (black); and FIG. 16B: blood (pre-transplantation and pooled sample d.22-50). Denominators for all calculations are the sum of all clones identifiable as recipient-derived on the basis of pre-transplant lymphoid tissue TCR sequencing.

FIG. 18A illustrates CFSE-MLR results for gated donor T cells with or without CD25 depletion in peripheral blood of one representative subject at the indicated long-term timepoints post-transplant. The donor CD4 and CD8 T cells responded to 3rd party antigens (right panels) but not to recipient antigens (left panels without CD25 depletion), despite the presence of strong pre-transplant responses. CD25 depletion partially restored the GvH responses of long-term circulating donor T cells. FIG. 18B illustrates summary of % $CFSE^{low}$ donor CD4 and CD8 T cells in MLRs using pre-transplantation donor splenocytes (Pts15, 7, and 16) or post-transplantation PBMCs (Pt15 POD214, Pt7 POD253) or splenocytes (Pt16 POD786) as responders against irradiated stimulators.

FIG. 19A illustrates CFSE-MLR results for gated recipient T cells in peripheral blood of one representative subject at day 253 post-transplant. The recipient CD4 and CD8 T cells responded to 3rd party antigens (right panels) more strongly than to donor antigens (middle panels) and did not respond to recipient antigens. FIG. 19B illustrates summary of % $CFSE^{low}$ donor CD4 and CD8 T cells in MLRs using pre-transplantation or late post-transplantation recipient splenocytes or PBMCs as responders against irradiated stimulators. There was a significant reduction in anti-donor CD8 responses post-compared to pre-transplant.

Figure 1A:
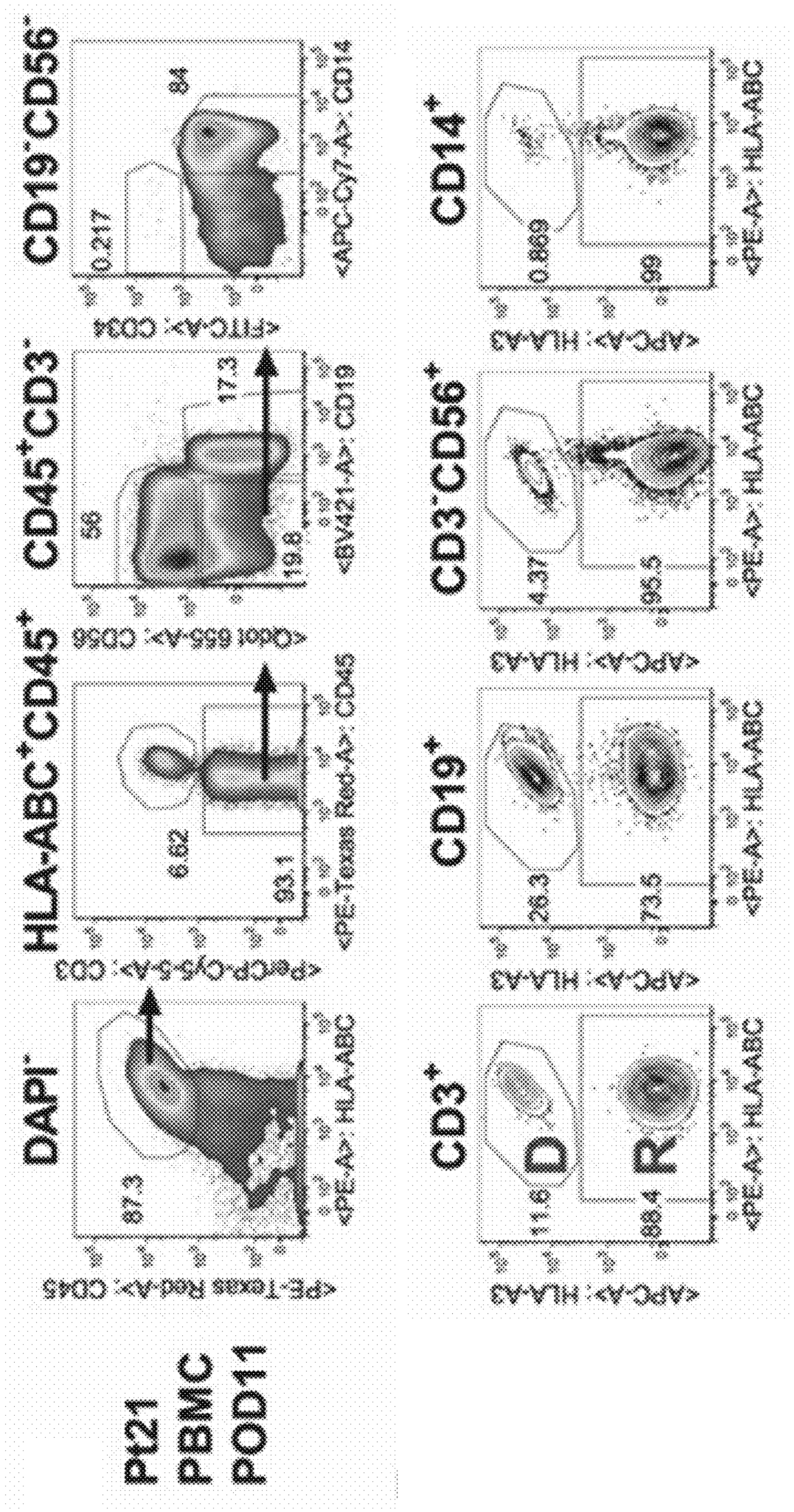
Figure 1D:
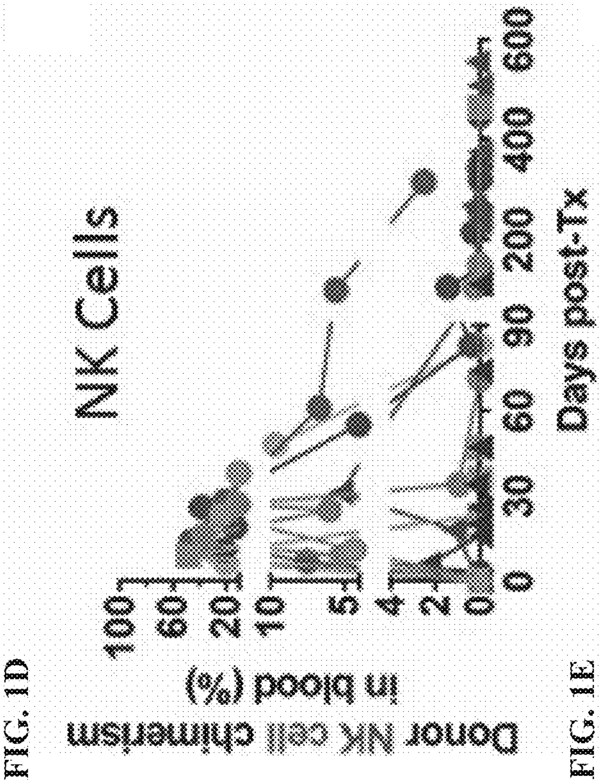
Figure 1E:
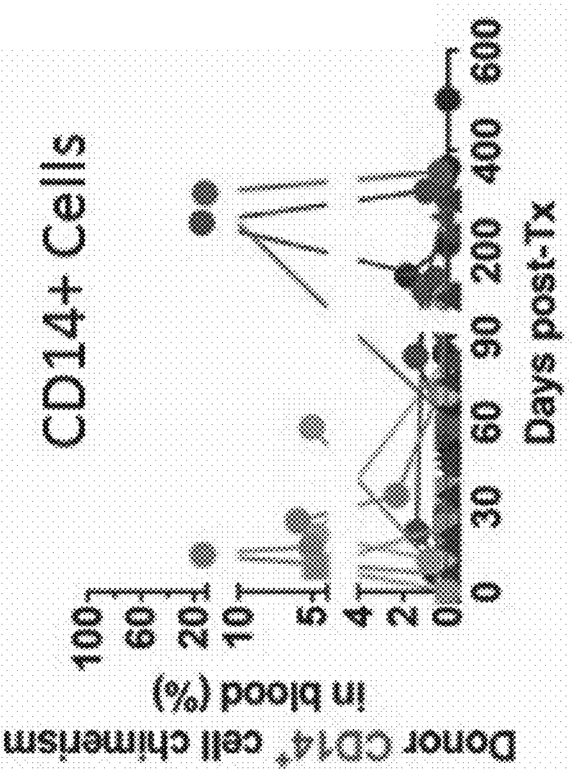
Figure 1E:
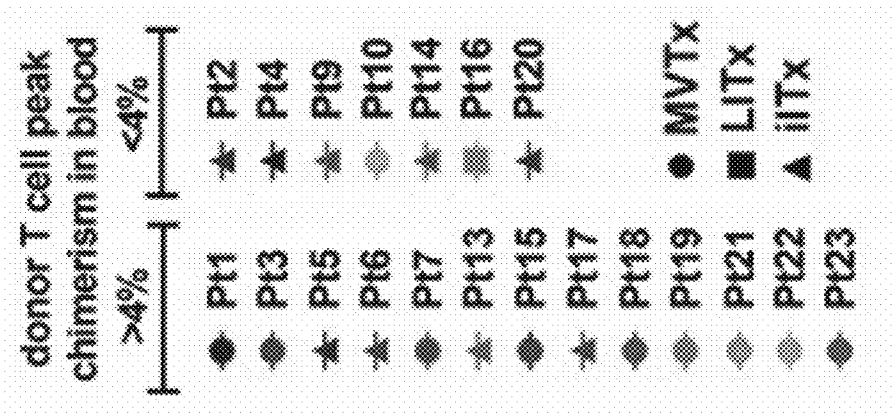

The novel features of the disclosure are set forth with particularity in the appended claims. A better understanding of the features and advantages of the present disclosure can be obtained by reference to the following detailed description that sets forth illustrative embodiments.

DETAILED DESCRIPTION

Overview

The survival rate of subjects who receive organ transplants is far from optimal due to high rejection rates resulting from the organ recipient's immune system attacking the donor's organ (termed host-vs-graft (HVG) alloreactivity). The high levels of global immunosuppression used to prevent rejection of a transplanted organ come with increased risk of infections and malignant diseases (i.e. lymphoma) for the organ recipient. Thus, there is an urgent need for a well-tolerated treatment option that controls rejection while reducing the aforementioned risks. Immune tolerance, which the immune system regards the donor's organ as the recipient's self so that long-term graft acceptance is achieved without life-long immunosuppression, can accomplish this goal. Accordingly, described herein are methods of infusion of cells such as bone marrow cells, immune cells, hematopoietic stem cells, or hematopoietic progenitor cells that are obtained from the same donor as the solid organ that is transplanted. This combination transplantation promotes a state called "mixed chimerism" in which both donor bone marrow cells, immune cells, hematopoietic stem cells, or hematopoietic progenitor cells and recipient bone marrow cells, immune cells, hematopoietic stem cells, or hematopoietic progenitor cells coexist in the donor recipient. Such mixed chimerism can induce tolerance to the transplanted organ in the subject donor recipient and allow for long-term acceptance of the transplanted organ and without increased risk of infections and malignant diseases.

In practice, it is not known how to obtain a population of bone marrow stem cells (e.g. CD34+ cells) necessary to promote a mixed chimerism. Described herein are methods for generating populations of bone marrow cells (e.g. cadaveric CD34+ cells) and administering the bone marrow cells to the recipient of an organ transplant wherein the donor-derived bone marrow cells coexist with the recipient's immune system within the organ transplant recipient.

Intestinal transplantation (ITx) encompasses four categories of visceral transplant: isolated intestine transplantation (iITx), liver and intestine transplantation (LITx), which often includes pancreas in pediatric cases, largely for technical reasons, multivisceral transplantation (MvTx), and multivisceral without the liver i.e., modified multivisceral transplantation (MMvTx). MvTx includes stomach and pancreas in addition to liver and intestine, with removal of the native stomach, pancreatico-duodenal complex and spleen. Indications include severe gastric dysmotility, pancreatitis, severe adhesions or fistulae, but are broader in some centers for children. Consequently, LITx including pancreas and MvTx can both be used for similar clinical scenarios in children at different centers. Abnormalities of the stomach in addition to intestinal failure, without liver failure, necessitate MMvTx. Abdominal trauma can necessitate any of the above categories of intestinal transplantation. As used herein, an organ transplant comprises transplantation of one or more of stomach, pancreas, liver, small intestine, large intestine, and kidney into a subject in need thereof. As used herein, a multivisceral transplant comprises transplantation of two or more of stomach, pancreas, liver, small intestine, large intestine, and kidney into a subject in need thereof.

Acute rejection limits the success of organ transplantation such as intestine transplantation (ITx). While infection remains the leading cause of death following ITx, death due to acute rejection accounts for about ⅓ of graft loss. ITx rejection initially involves mixed inflammatory infiltrates in the lamina propria and mucosal interstitium and immune injury to epithelial crypt cells. Progression leads to shortening and flattening of villi, which can culminate in extensive destruction of bowel mucosa ("exfoliation"), severe inflammation, mucosal denudation, and granulation tissue. Signs of rejection include increased stomal output, but symptoms can initially be absent. Advanced rejection is associated with fever, bloody discharge or sloughing of tissue, at which point a graft cannot be salvageable. Therefore, frequent surveillance of endoscopic biopsies are used to detect early rejection. In addition to high rejection rates, the success of ITx is currently limited by the risk of graft-vs-host disease (GvHD) and by infections and post-transplant lymphoproliferative disease (PTLD) resulting from high levels of immunosuppression. There is an urgent need, therefore, for a well-tolerated treatment strategy that controls rejection while reducing these risks. "Personalized immunosuppression" (stratifying immune-suppressive regimens according to the subject's rejection risk) can improve outcomes. Additionally, long-term graft acceptance needs to be achieved without life-long immunosuppression and its attendant toxicities.

Described herein are methods for establishing a long-term mixed chimerism or macrochimerism in a subject who receives an organ transplant. In some embodiments, the mixed chimerism or macrochimerism is established transiently in the subject. In some embodiments, the mixed chimerism or macrochimerism is established permanently in the subject. In some embodiments, establishing mixed chimerism or macrochimerism in the subject prevents or decreases rejection of the transplanted organ in the subject.

In some embodiments, a population of hematopoietic stem cells or hematopoietic progenitor cells can be administered (e.g., infused) to the subject. In some embodiments, the hematopoietic stem cells or hematopoietic progenitor cells can be CD34+ cells. In some embodiments, the population of hematopoietic stem cells or hematopoietic progenitor cells can be from a cadaveric source.

In some embodiments, GvH-reactive T cells are expanded from administered bone marrow stem cells comprising immune cells, hematopoietic stem cells, and/or hematopoietic progenitor cells (e.g. CD34+ cells) in the bone marrow of a subject who received an organ transplant. GvH-reactive T cells from the administered bone marrow stem cells enter the recipient's peripheral circulation and bone marrow early after administration, thereby promoting and maintaining mixed chimerism. In some embodiments, lymphohematopoietic graft-vs-host responses (LGvHR) can convert the mixed chimerism to full donor chimerism by attacking recipient hematopoietic cells without causing GvHD and suppress rejection of the transplanted organ that is induced by host vs graft (HvG)-reactive T cells.

In some embodiments, LGvHR makes space for engraftiment of donor hematopoietic cells and reduces HvG activity, resulting in reduced rejection rates of the transplanted organ without causing GvHD.

In some embodiments, a population of bone marrow stem cells comprising immune cells, hematopoietic stem cells, and/or hematopoietic progenitor cells can be administered (e.g., infused) before lymphohematopoietic GvH response (LGvHR) is observed in the subject. In some embodiments, a population of bone marrow stem cells comprising immune cells, hematopoietic stem cells and/or hematopoietic progenitor cells can be administered (e.g., infused) during development of LGvHR. In some embodiments, a population of bone marrow stem cells comprising immune cells, hematopoietic stem cells, and/or hematopoietic progenitor cells can be administered (e.g., infused) after LGvHR is eliminated from the subject. In some embodiments, a population of bone marrow stem cells comprising immune cells, hematopoietic stem cells, and/or hematopoietic progenitor cells can be administered (e.g., infused) to the subject at the time of maximal LGvHR In some embodiments, the administration of a population of bone marrow stem cells comprising immune cells, hematopoietic stem cells, and/or hematopoietic progenitor cells at the time of maximal LGvHR can increase the level and duration of donor multilineage chimerism in the blood without inducing GvHD and permit immunosuppression tapering, thereby reducing risks of opportunistic infections and malignancies. In some embodiments, the population of bone marrow stem cells comprising immune cells, hematopoietic stem cells, and/or hematopoietic progenitor cells can be CD34+ cells. In some embodiments, the population of bone marrow stem cells comprising immune cells, hematopoietic stem cells, and/or hematopoietic progenitor cells can be from a cadaveric source (e.g. cadaveric CD34+ cells). In some cases, the bone marrow stem cells are obtained from the cadaveric donor as the organs that are transplanted to the subject.

In some embodiments, the mixed chimerism or macrochimerism can be established by administering a population of hematopoietic stem cells or hematopoietic progenitor cells that is allogenic to the subject. In some embodiments, the population of hematopoietic stem cells or hematopoietic progenitor cells are from the organ donor, who donates the organ to the subject. In some embodiments, the population of hematopoietic stem cells or hematopoietic progenitor cells are from a different donor (e.g. other than the organ donor), whose human leukocyte antigen (HLA) matches the subject donor recipient. In some embodiments, the population of hematopoietic stem cells or hematopoietic progenitor cells can be from a cadaveric source. In some embodiments, the methods described herein comprise administering at least one additional immunosuppressant in conjunction with the administration of the population of cells described herein. In some cases, the administration of the at least one additional immunosuppressant can be tapered over time. In some instances, the amounts of the at least one additional immunosuppressant administered to the subject organ recipient can be decreased compared to when the subject not administered with the population of cells described here. In some embodiments, the frequencies of the at least one additional immunosuppressant administered to the subject organ recipient can be decreased compared to when the subject not administered with the population of cells described here.

Chimerism

Described herein, in some embodiments, are methods for establishing chimerism in a subject who is a recipient of organ transplantation. In some cases, the chimerism described herein refers to a mixture of a type of cells in the subject, where the cells comprise two or more genotypes. In some embodiments, the methods described herein comprises establishing chimerism of cells such as hematopoietic stem cells, hematopoietic progenitor cells, or immune cells. In some cases, the chimerism can be established by administering a populations of cells to the subject, where the populations of cells are genotypically distinct from the subject. In some cases, the organ transplantation can be multivisceral transplantation (MvTx), where the subject receives any combination of stomach, pancreas, liver, spleen, small intestine, or large intestine. In some instances, the organ transplantation can be intestinal transplant (ITx) encompassing four categories of visceral transplant: isolated intestine (iITx), liver and intestine (LITx), which often includes pancreas in pediatric cases, largely for technical reasons, multivisceral (MvTx), and multivisceral without the liver i.e., modified multivisceral (MMvTx). MvTx includes stomach and pancreas in addition to liver/intestine, with removal of the native stomach, pancreatico-duodenal complex and spleen. In some embodiments, the chimerism can be established in the subject before the subject receiving the organ transplantation. In some embodiments, the chimerism can be established in the subject after the subject receiving the organ transplantation. In some embodiments, the chimerism can be transiently established in the subject. In such case, the chimerism can be re-established by additional administration of the population of cells described herein. In some embodiments, the chimerism can be permanently established in the subject. In some embodiments, the chimerism can be established by administering a population cells to the subject, where the population of the administered cells comprise HLA that matches the HLA of the subject. In some embodiments, the population of cells administered to the subject is allogenic to the subject. In some embodiments, the population of cells administered to the subject is from the organ donor, who donates the organ to the subject. In some embodiments, the population of cells administered to the is from a different donor (e.g. other than the organ donor), whose human leukocyte antigen (HLA) matches the subject donor recipient. In some embodiments, the chimerism can be established by transplanting the organ or tissue, where the organ or tissue comprises niche or graft containing hematopoietic stem cells or hematopoietic progenitor cells.

In some embodiments, the chimerism comprises chimerism of hematopoietic stem cells or hematopoietic progenitor cells. In some embodiments, the chimerism comprises chimerism of myeloid cells. In some embodiments, the chimerism comprises chimerism of immune cells derived from hematopoietic stem cells or hematopoietic progenitor cells. In some embodiments, the immune cells can be any one of monocyte, T cell, B cell, dendritic cell, macrophage, NK cell, or NKT cell. For example, the chimerism described herein can be chimerism comprising the subject's T cell and a sperate population of T cells administered to the subject. In some embodiments, the immune cells can be T cells. In some embodiments, the immune cells can be B cells. In some instances, the mixed chimerism or macrochimerism can be chimerism of T cells. In some cases, the mixed chimerism or macrochimerism can be chimerism of B cells.

In some embodiments, the chimerism can be a mixed chimerism. In some cases, the mixed chimerism is established by administered to the subject the population of cells (e.g. population of hematopoietic stem cells, hematopoietic progenitor cells, or immune cells) described herein. In some embodiments, the mixed chimerism can comprise at least 0.01%, 0.02%, 0.03%, 0.04%, 0.05%, 0.1%, 0.2%, 0.3%, 0.4%, 0.5%, 1.0%, 2.0%, 3.0%, 4.0%, 5.0%, 6.0%, 7.0%, 8.0%, 9.0%, 10.0%, 20.0%, 30.0%, 40.0%, 50.0%, 60.0%, 70.0%, 80.0%, 90.0%, 95.0%, or 99.0% of the cells that are genotypically distinct from the subject. In some embodiments, the mixed chimerism is between about 0.01% to about 50%. In some embodiments, the mixed chimerism is between about 0.01% to about 0.05%, about 0.01% to about 0.1%, about 0.01% to about 0.5%, about 0.01% to about 1%, about 0.01% to about 2%, about 0.01% to about 3%, about 0.01% to about 4%, about 0.01% to about 5%, about 0.01% to about 10%, about 0.01% to about 25%, about 0.01% to about 50%, about 0.05% to about 0.1%, about 0.05% to about 0.5%, about 0.05% to about 1%, about 0.05% to about 2%, about 0.05% to about 3%, about 0.05% to about 4%, about 0.05% to about 5%, about 0.05% to about 10%, about 0.05% to about 25%, about 0.05% to about 50%, about 0.1% to about 0.5%, about 0.1% to about 1%, about 0.1% to about 2%, about 0.1% to about 3%, about 0.1% to about 4%, about 0.1% to about 5%, about 0.1% to about 10%, about 0.1% to about 25%, about 0.1% to about 50%, about 0.5% to about 1%, about 0.5% to about 2%, about 0.5% to about 3%, about 0.5% to about 4%, about 0.5% to about 5%, about 0.5% to about 10%, about 0.5% to about 25%, about 0.5% to about 50%, about 1% to about 2%, about 1% to about 3%, about 1% to about 4%, about 1% to about 5%, about 1% to about 10%, about 1% to about 25%, about 1% to about 50%, about 2% to about 3%, about 2% to about 4%, about 2% to about 5%, about 2% to about 10%, about 2% to about 25%, about 2% to about 50%, about 3% to about 4%, about 3% to about 5%, about 3% to about 10%, about 3% to about 25%, about 3% to about 50%, about 4% to about 5%, about 4% to about 10%, about 4% to about 25%, about 4% to about 50%, about 5% to about 10%, about 5% to about 25%, about 5% to about 50%, about 10% to about 25%, about 10% to about 50%, or about 25% to about 50%. In some embodiments, the mixed chimerism is between about 0.01%, about 0.05%, about 0.1%, about 0.5%, about 1%, about 2%, about 3%, about 4%, about 5%, about 10%, about 25%, or about 50%. In some embodiments, the mixed chimerism is between about at least about 0.01%, about 0.05%, about 0.1%, about 0.5%, about 1%, about 2%, about 3%, about 4%, about 5%, about 10%, or about 25%. In some embodiments, the mixed chimerism is between about at most about 0.05%, about 0.1%, about 0.5%, about 1%, about 2%, about 3%, about 4%, about 5%, about 10%, about 25%, or about 50%.

In some embodiments, the chimerism can be a macrochimerism. In some cases, the macrochimerism is established by administered to the subject the population of cells (e.g. population of hematopoietic stem cells, hematopoietic progenitor cells, or immune cells) described herein. In some embodiments, the macrochimerism can comprise at least 0.1%, 0.2%, 0.3%, 0.4%, 0.5%, 1.0%, 2.0%, 3.0%, 4.0%, 5.0%, 6.0%, 7.0%, 8.0%, 9.0%, 10.0%, 20.0%, 30.0%, 40.0%, 50.0%, 60.0%, 70.0%, 80.0%, 90.0%, 95.0%, or 99.0% of the cells that are genotypically distinct from the subject. In some embodiments, the macrochimerism comprises at 4% of the cells that are genotypically distinct from the subject. In some embodiments, the macrochimerism is between about 0.1% to about 50%. In some embodiments, the macrochimerism is between about 0.1% to about 0.5%, about 0.1% to about 1%, about 0.1% to about 2%, about 0.1% to about 3%, about 0.1% to about 4%, about 0.1% to about 5%, about 0.1% to about 10%, about 0.1% to about 25%, about 0.1% to about 30%, about 0.1% to about 40%, about 0.1% to about 50%, about 0.5% to about 1%, about 0.5% to about 2%, about 0.5% to about 3%, about 0.5% to about 4%, about 0.5% to about 5%, about 0.5% to about 10%, about 0.5% to about 25%, about 0.5% to about 30%, about 0.5% to about 40%, about 0.5% to about 50%, about 1% to about 2%, about 1% to about 3%, about 1% to about 4%, about 1% to about 5%, about 1% to about 10%, about 1% to about 25%, about 1% to about 30%, about 1% to about 40%, about 1% to about 50%, about 2% to about 3%, about 2% to about 4%, about 2% to about 5%, about 2% to about 10%, about 2% to about 25%, about 2% to about 30%, about 2% to about 40%, about 2% to about 50%, about 3% to about 4%, about 3% to about 5%, about 3% to about 10%, about 3% to about 25%, about 3% to about 30%, about 3% to about 40%, about 3% to about 50%, about 4% to about 5%, about 4% to about 10%, about 4% to about 25%, about 4% to about 30%, about 4% to about 40%, about 4% to about 50%, about 5% to about 10%, about 5% to about 25%, about 5% to about 30%, about 5% to about 40%, about 5% to about 50%, about 10% to about 25%, about 10% to about 30%, about 10% to about 40%, about 10% to about 50%, about 25% to about 30%, about 25% to about 40%, about 25% to about 50%, about 30% to about 40%, about 30% to about 50%, or about 40% to about 50%. In some embodiments, the macrochimerism is between about 0.1%, about 0.5%, about 1%, about 2%, about 3%, about 4%, about 5%, about 10%, about 25%, about 30%, about 40%, or about 50%. In some embodiments, the macrochimerism is between about at least about 0.1%, about 0.5%, about 1%, about 2%, about 3%, about 4%, about 5%, about 10%, about 25%, about 30%, or about 40%. In some embodiments, the macrochimerism is between about at most about 0.5%, about 1%, about 2%, about 3%, about 4%, about 5%, about 10%, about 25%, about 30%, about 40%, or about 50%.

In some embodiments, the mixed chimerism or macrochimerism established in the subject can be verified by methods commonly used to detect chimerism. For example, the chimerism can be determined by flow cytometry, PCR sequence, nucleic acid sequencing, and immunostaining. In some embodiments, the chimerism can be determined in bone marrow of the subject. In some embodiments, the chimerism can be determined in the peripheral blood of the subject. In some embodiments, the chimerism can be determined in a biopsy sample obtained from the subject. Biopsy sample can be boned from bone marrow, liver, spleen, pancreas, small intestine, largen intestine, or any other organ or tissues types.

In some embodiments, the chimerism established in the subject can prevent or decrease GvHR or GvHD in the subject who receives the transplanted organ as determined by the methods described herein. For example, the prevention or decreasing of GvHR or GvHD in the subject can be determined by the ratio of T cell clones from the donor of the population of the cells and the T cells clones from the subject, where the increased T cell clones from the donor can be indicative of the prevention or decrease of GvHR or GvHD. In some embodiments, the increased T cell clones from the subject can be indicative of the prevention or decrease of GvHR or GvHD. In some embodiments, the methods of establishing chimerism described herein can prevent GvHR or GvHD in the subject. In some embodiments, the methods of establishing chimerism described herein can decrease GvHR or GvHD as determined by the ratio of the T cell clones from the donor and T cell clones from the subject. In some embodiments, the methods of establishing chimerism described herein can decrease GvHR or GvHD by at least about 1 fold to about 50 fold. In some embodiments, the methods of establishing chimerism described herein can decrease GvHR or GvHD by at least about 1 fold to about 2 fold, about 1 fold to about 3 fold, about 1 fold to about 4 fold, about 1 fold to about 5 fold, about 1 fold to about 10 fold, about 1 fold to about 20 fold, about 1 fold to about 30 fold, about 1 fold to about 40 fold, about 1 fold to about 50 fold, about 2 fold to about 3 fold, about 2 fold to about 4 fold, about 2 fold to about 5 fold, about 2 fold to about 10 fold, about 2 fold to about 20 fold, about 2 fold to about 30 fold, about 2 fold to about 40 fold, about 2 fold to about 50 fold, about 3 fold to about 4 fold, about 3 fold to about 5 fold, about 3 fold to about 10 fold, about 3 fold to about 20 fold, about 3 fold to about 30 fold, about 3 fold to about 40 fold, about 3 fold to about 50 fold, about 4 fold to about 5 fold, about 4 fold to about 10 fold, about 4 fold to about 20 fold, about 4 fold to about 30 fold, about 4 fold to about 40 fold, about 4 fold to about 50 fold, about 5 fold to about 10 fold, about 5 fold to about 20 fold, about 5 fold to about 30 fold, about 5 fold to about 40 fold, about 5 fold to about 50 fold, about 10 fold to about 20 fold, about 10 fold to about 30 fold, about 10 fold to about 40 fold, about 10 fold to about 50 fold, about 20 fold to about 30 fold, about 20 fold to about 40 fold, about 20 fold to about 50 fold, about 30 fold to about 40 fold, about 30 fold to about 50 fold, or about 40 fold to about 50 fold. In some embodiments, the methods of establishing chimerism described herein can decrease GvHR or GvHD by at least about 1 fold, about 2 fold, about 3 fold, about 4 fold, about 5 fold, about 10 fold, about 20 fold, about 30 fold, about 40 fold, or about 50 fold. In some embodiments, the methods of establishing chimerism described herein can decrease GvHR or GvHD by at least at least about 1 fold, about 2 fold, about 3 fold, about 4 fold, about 5 fold, about 10 fold, about 20 fold, about 30 fold, or about 40 fold. In some embodiments, the methods of establishing chimerism described herein can decrease GvHR or GvHD by at least at most about 1 fold, about 2 fold, about 3 fold, about 4 fold, about 5 fold, about 10 fold, about 20 fold, about 30 fold, about 40 fold, or about 50 fold.

In some embodiments, establishing mixed chimerism or macrochimerism in the subject prevents or decreases rejection of the transplanted organ in the subject. In some embodiments, the prevention or decrease of rejection of the transplanted organ can be determined by: measuring the ratio of the cells of the donor and the cells of the subject; or by measuring the survival of the graft cells after transplantation. For example, prevention or decrease of rejection can be determined by measuring the ratio of the T cell clones of the donor and the T cell clones of the subject. In some embodiments, establishing mixed chimerism or macrochimerism in the subject prevents rejection of the transplanted organ in the subject. In some embodiments, establishing mixed chimerism or macrochimerism in the subject decreases rejection of the transplanted organ in the subject as determined by the ratio of clones from the donor and clones of the subject described herein. In some embodiments, the methods of establishing chimerism described herein can decrease rejection by at least about 1 fold to about 50 fold. In some embodiments, the methods of establishing chimerism described herein can decrease rejection by at least about 1 fold to about 2 fold, about 1 fold to about 3 fold, about 1 fold to about 4 fold, about 1 fold to about 5 fold, about 1 fold to about 10 fold, about 1 fold to about 20 fold, about 1 fold to about 30 fold, about 1 fold to about 40 fold, about 1 fold to about 50 fold, about 2 fold to about 3 fold, about 2 fold to about 4 fold, about 2 fold to about 5 fold, about 2 fold to about 10 fold, about 2 fold to about 20 fold, about 2 fold to about 30 fold, about 2 fold to about 40 fold, about 2 fold to about 50 fold, about 3 fold to about 4 fold, about 3 fold to about 5 fold, about 3 fold to about 10 fold, about 3 fold to about 20 fold, about 3 fold to about 30 fold, about 3 fold to about 40 fold, about 3 fold to about 50 fold, about 4 fold to about 5 fold, about 4 fold to about 10 fold, about 4 fold to about 20 fold, about 4 fold to about 30 fold, about 4 fold to about 40 fold, about 4 fold to about 50 fold, about 5 fold to about 10 fold, about 5 fold to about 20 fold, about 5 fold to about 30 fold, about 5 fold to about 40 fold, about 5 fold to about 50 fold, about 10 fold to about 20 fold, about 10 fold to about 30 fold, about 10 fold to about 40 fold, about 10 fold to about 50 fold, about 20 fold to about 30 fold, about 20 fold to about 40 fold, about 20 fold to about 50 fold, about 30 fold to about 40 fold, about 30 fold to about 50 fold, or about 40 fold to about 50 fold. In some embodiments, the methods of establishing chimerism described herein can decrease rejection by at least about 1 fold, about 2 fold, about 3 fold, about 4 fold, about 5 fold, about 10 fold, about 20 fold, about 30 fold, about 40 fold, or about 50 fold. In some embodiments, the methods of establishing chimerism described herein can decrease rejection by at least at least about 1 fold, about 2 fold, about 3 fold, about 4 fold, about 5 fold, about 10 fold, about 20 fold, about 30 fold, or about 40 fold. In some embodiments, the methods of establishing chimerism described herein can decrease rejection by at least at most about 1 fold, about 2 fold, about 3 fold, about 4 fold, about 5 fold, about 10 fold, about 20 fold, about 30 fold, about 40 fold, or about 50 fold. In some embodiments, the methods described herein does not result in a Grade II or greater GvHD in the subject who receives the transplanted organ.

Immunosuppressants

Described herein, in some embodiments, are methods for establishing a long-term chimerism in a subject who is a recipient of organ transplantation. In some embodiments, the methods described herein prevent or decrease GvHD in the subject who receives the transplanted organ. In some embodiments, the methods described herein prevent or decrease rejection of the transplanted organ in the subject. In some embodiments, the methods described herein comprise administering to the subject at least one additional immunosuppressant in conjunction with the administration of the population of cells described herein. The immunosuppressant can be any one of or any combination of the immunosuppressants that are commonly used. In some cases, the immunosuppressants can be glucocorticoids, corticosteroids, anti-thymocyte globulin, cytostatics, antibodies, drugs acting on immunophilins, or any other immunosuppressant drugs. In some embodiments, the immunosuppressant can be a glucocorticoid selected from a group of hydrocortisone, cortisone, ethamethasoneb, prednisone, prednisolone, triamcinolone, tacrolimus, or methylprednisolone. In some cases, the immunosuppressant can be anti-thymocyte globulin. In some embodiments, the immunosuppressant can be tacrolimus. In some instances, the immunosuppressant can be prednisone. In some embodiments, the at least one additional immunosuppressant, when administered in conjunction with the population of the cells described herein, can prevent or decrease GvHD in the subject who receives the transplanted organ. In some embodiments, the at least one additional immunosuppressant, when administered in conjunction with the population of the cells described herein, can prevent or decrease GvHD in the subject who receives the transplanted organ compared to only administrating the same immunosuppressant but without administering the populations of cells described herein. In some embodiments, the at least one additional immunosuppressant, when administered in conjunction with the population of the cells described herein, can prevent or decrease rejection of the transplanted organ in the subject. In some embodiments, the at least one additional immunosuppressant, when administered in conjunction with the population of the cells described herein, can prevent or decrease rejection of the transplanted organ in the subject compared to only administrating the same immunosuppressant but without administering the populations of cells described herein.

In some embodiments, the immunosuppressant, when administered in conjunction with the population of the cells described herein, can prevent or decrease GvHD in the subject organ recipient compared to only administrating the same immunosuppressant but without administering the populations of cells described herein. In some embodiments, the immunosuppressant can be anti-thymocyte globulin, tacrolimus, or prednisone. In some embodiments, the immunosuppressant, when administered in conjunction with the population of the cells described herein, can prevent GvHD in the subject organ recipient compared to only administrating the same immunosuppressant but without administering the populations of cells described herein. In some embodiments, the administering of the at least one immunosuppressant can decrease GvHD by at least about 1 fold to about 50 fold. In some embodiments, the administering of the at least one immunosuppressant can decrease GvHD by at least about 1 fold to about 2 fold, about 1 fold to about 3 fold, about 1 fold to about 4 fold, about 1 fold to about 5 fold, about 1 fold to about 10 fold, about 1 fold to about 20 fold, about 1 fold to about 30 fold, about 1 fold to about 40 fold, about 1 fold to about 50 fold, about 2 fold to about 3 fold, about 2 fold to about 4 fold, about 2 fold to about 5 fold, about 2 fold to about 10 fold, about 2 fold to about 20 fold, about 2 fold to about 30 fold, about 2 fold to about 40 fold, about 2 fold to about 50 fold, about 3 fold to about 4 fold, about 3 fold to about 5 fold, about 3 fold to about 10 fold, about 3 fold to about 20 fold, about 3 fold to about 30 fold, about 3 fold to about 40 fold, about 3 fold to about 50 fold, about 4 fold to about 5 fold, about 4 fold to about 10 fold, about 4 fold to about 20 fold, about 4 fold to about 30 fold, about 4 fold to about 40 fold, about 4 fold to about 50 fold, about 5 fold to about 10 fold, about 5 fold to about 20 fold, about 5 fold to about 30 fold, about 5 fold to about 40 fold, about 5 fold to about, about 10 fold to about 20 fold, about 10 fold to about 30 fold, about 10 fold to about 40 fold, about 10 fold to about 50 fold, about 20 fold to about 30 fold, about 20 fold to about 40 fold, about 20 fold to about 50 fold, about 30 fold to about 40 fold, about 30 fold to about 50 fold, or about 40 fold to about 50 fold. In some embodiments, the administering of the at least one immunosuppressant can decrease GvHD by at least about 1 fold, about 2 fold, about 3 fold, about 4 fold, about 5 fold, about 10 fold, about 20 fold, about 30 fold, about 40 fold, or about 50 fold. In some embodiments, the administering of the at least one immunosuppressant can decrease GvHD by at least at least about 1 fold, about 2 fold, about 3 fold, about 4 fold, about 5 fold, about 10 fold, about 20 fold, about 30 fold, or about 40 fold. In some embodiments, the administering of the at least one immunosuppressant can decrease GvHD by at least at most about 1 fold, about 2 fold, about 3 fold, about 4 fold, about 5 fold, about 10 fold, about 20 fold, about 30 fold, about 40 fold, or about 50 fold.

In some embodiments, the immunosuppressant, when administered in conjunction with the population of the cells described herein, can prevent or decrease rejection of the transplanted organ in the subject organ recipient compared to only administrating the same immunosuppressant but without administering the populations of cells described herein. In some embodiments, the immunosuppressant can be anti-thymocyte globulin or tacrolimus. In some embodiments, the immunosuppressant, when administered in conjunction with the population of the cells described herein, can prevent rejection of the transplanted organ in the subject organ recipient compared to only administrating the same immunosuppressant but without administering the populations of cells described herein. In some embodiments, the administering of the at least one immunosuppressant can decrease rejection of the transplanted organ by at least about 1 fold to about 50 fold. In some embodiments, the administering of the at least one immunosuppressant can decrease rejection of the transplanted organ by at least about 1 fold to about 2 fold, about 1 fold to about 3 fold, about 1 fold to about 4 fold, about 1 fold to about 5 fold, about 1 fold to about 10 fold, about 1 fold to about 20 fold, about 1 fold to about 30 fold, about 1 fold to about 40 fold, about 1 fold to about 50 fold, about 2 fold to about 3 fold, about 2 fold to about 4 fold, about 2 fold to about 5 fold, about 2 fold to about 10 fold, about 2 fold to about 20 fold, about 2 fold to about 30 fold, about 2 fold to about 40 fold, about 2 fold to about 50 fold, about 3 fold to about 4 fold, about 3 fold to about 5 fold, about 3 fold to about 10 fold, about 3 fold to about 20 fold, about 3 fold to about 30 fold, about 3 fold to about 40 fold, about 3 fold to about 50 fold, about 4 fold to about 5 fold, about 4 fold to about 10 fold, about 4 fold to about 20 fold, about 4 fold to about 30 fold, about 4 fold to about 40 fold, about 4 fold to about 50 fold, about 5 fold to about 10 fold, about 5 fold to about 20 fold, about 5 fold to about 30 fold, about 5 fold to about 40 fold, about 5 fold to about 50 fold, about 10 fold to about 20 fold, about 10 fold to about 30 fold, about 10 fold to about 40 fold, about 10 fold to about 50 fold, about 20 fold to about 30 fold, about 20 fold to about 40 fold, about 20 fold to about 50 fold, about 30 fold to about 40 fold, about 30 fold to about 50 fold, or about 40 fold to about 50 fold. In some embodiments, the administering of the at least one immunosuppressant can decrease rejection of the transplanted organ by at least about 1 fold, about 2 fold, about 3 fold, about 4 fold, about 5 fold, about 10 fold, about 20 fold, about 30 fold, about 40 fold, or about 50 fold. In some embodiments, the administering of the at least one immunosuppressant can decrease rejection of the transplanted organ by at least at least about 1 fold, about 2 fold, about 3 fold, about 4 fold, about 5 fold, about 10 fold, about 20 fold, about 30 fold, or about 40 fold. In some embodiments, the administering of the at least one immunosuppressant can decrease rejection of the transplanted organ by at least at most about 1 fold, about 2 fold, about 3 fold, about 4 fold, about 5 fold, about 10 fold, about 20 fold, about 30 fold, about 40 fold, or about 50 fold.

In some embodiments, the administration of the at least one additional immunosuppressant can be tapered during or after the subject receiving the organ transplantation and after the population of cells are administered to the subject while retaining the prevention or decrease GvHD, or rejection of the transplanted organ in the subject. In some embodiments, the at least one immunosuppressant can be anti-thymocyte globulin, tacrolimus, or prednisone. In some embodiments, the administration of the at least one additional immunosuppressant can be tapered after the administration of the population of cells described herein. In some embodiments, the administration of the at least one additional immunosuppressant can be tapered compared to the amount or the frequency of the same immunosuppressant administered to the subject who has not received the administration or infusion of the population of cells described herein. In some embodiments, the administration of the at least one additional immunosuppressant can be tapered by about 0.1% to about 50%. In some embodiments, the administration of the at least one additional immunosuppressant can be tapered by about 0.1% to about 0.5%, about 0.1% to about 1%, about 0.1% to about 2%, about 0.1% to about 3%, about 0.1% to about 4%, about 0.1% to about 5%, about 0.1% to about 10%, about 0.1% to about 25%, about 0.1% to about 30%, about 0.1% to about 40%, about 0.1% to about 50%, about 0.5% to about 1%, about 0.5% to about 2%, about 0.5% to about 3%, about 0.5% to about 4%, about 0.5% to about 5%, about 0.5% to about 10%, about 0.5% to about 25%, about 0.5% to about 30%, about 0.5% to about 40%, about 0.5% to about 50%, about 1% to about 2%, about 1% to about 3%, about 1% to about 4%, about 1% to about 5%, about 1% to about 10%, about 1% to about 25%, about 1% to about 30%, about 1% to about 40%, about 1% to about 50%, about 2% to about 3%, about 2% to about 4%, about 2% to about 5%, about 2% to about 10%, about 2% to about 25%, about 2% to about 30%, about 2% to about 40%, about 2% to about 50%, about 3% to about 4%, about 3% to about 5%, about 3% to about 10%, about 3% to about 25%, about 3% to about 30%, about 3% to about 40%, about 3% to about 50%, about 4% to about 5%, about 4% to about 10%, about 4% to about 25%, about 4% to about 30%, about 4% to about 40%, about 4% to about 50%, about 5% to about 10%, about 5% to about 25%, about 5% to about 30%, about 5% to about 40%, about 5% to about 50%, about 10% to about 25%, about 10% to about 30%, about 10% to about 40%, about 10% to about 50%, about 25% to about 30%, about 25% to about 40%, about 25% to about 50%, about 30% to about 40%, about 30% to about 50%, or about 40% to about 50%. In some embodiments, the administration of the at least one additional immunosuppressant can be tapered by about 0.1%, about 0.5%, about 1%, about 2%, about 3%, about 4%, about 5%, about 10%, about 25%, about 30%, about 40%, or about 50%. In some embodiments, the administration of the at least one additional immunosuppressant can be tapered by at least about 0.1%, about 0.5%, about 1%, about 2%, about 3%, about 4%, about 5%, about 10%, about 25%, about 30%, or about 40%. In some embodiments, the administration of the at least one additional immunosuppressant can be tapered by at most about 0.5%, about 1%, about 2%, about 3%, about 4%, about 5%, about 10%, about 25%, about 30%, about 40%, or about 50%.

In some embodiments, the administration of the at least one additional immunosuppressant can be tapered at least one, two, three, four, five, six, seven, eight, nine, ten, 11, 12, 13, 14, 15, 20, 30, or more days after the subject has received the organ transplant or after the subject has received the administration of the population of cells described herein. In some embodiments, the administration of the at least one additional immunosuppressant can be tapered at least one, two, three, four, five, six, seven, eight, nine, ten, 11, 12, 13, 14, 15, 20, 30, or more weeks after the subject has received the organ transplant or after the subject has received the administration of the population of cells described herein. In some embodiments, the administration of the at least one additional immunosuppressant can be tapered at least one, two, three, four, five, six, seven, eight, nine, ten, 11, 12, 13, 14, 15, 20, 30, or more months after the subject has received the organ transplant or after the subject has received the administration of the population of cells described herein. In some embodiments, the administration of the at least one additional immunosuppressant can be tapered at least one, two, three, four, five, six, seven, eight, nine, ten, 11, 12, 13, 14, 15, 20, 30, or more years after the subject has received the organ transplant or after the subject has received the administration of the population of cells described herein. In some embodiments, the administration of the at least one additional immunosuppressant can be tapered to discontinuation.

In some embodiments, the at least one additional immunosuppressant can be administered to the subject at least ten, nine, eight, seven, six, five, four, three, two, or one day before the subject receiving the organ transplantation. In some embodiments, the at least one additional immunosuppressant can be administered to the subject at the same time as the subject is receiving the organ transplantation. In some embodiments, the at least one additional immunosuppressant can be administered to the subject at least one, two, three, four, five, six, seven, eight, nine, ten, or more days after the subject has received the organ transplantation. In some embodiments, the at least one additional immunosuppressant can be administered to the subject at least one, two, three, four, five, six, seven, eight, nine, ten, or more weeks after the subject has received the organ transplantation. In some embodiments, the at least one additional immunosuppressant can be administered to the subject at least one, two, three, four, five, six, seven, eight, nine, ten, eleven, or more months after the subject has received the organ transplantation. In some embodiments, the at least one additional immunosuppressant can be administered to the subject at least one, two, three, four, five, six, seven, eight, nine, ten, or more years after the subject has received the organ transplantation. In some embodiments, the at least one additional immunosuppressant can be administered to the subject daily, weekly, monthly, yearly, or any time interval as deemed necessary. In some embodiments, the administration of the at least one additional immunosuppressant can be discontinued after administration of the population of the cells described herein.

In some embodiments, the amount of the at least one additional immunosuppressant administered to the subject is decreased when the subject also receives the population of cells described herein (e.g. compared to when the subject does not receive the population of cells described herein). In some embodiments, the amount of the at least one additional immunosuppressant administered to the subject is decreased by at least about 0.01 fold to about 100 fold. In some embodiments, the amount of the at least one additional immunosuppressant administered to the subject is decreased by at least about 0.01 fold to about 0.05 fold, about 0.01 fold to about 0.1 fold, about 0.01 fold to about 0.5 fold, about 0.01 fold to about 1 fold, about 0.01 fold to about 2 fold, about 0.01 fold to about 5 fold, about 0.01 fold to about 10 fold, about 0.01 fold to about 20 fold, about 0.01 fold to about 50 fold, about 0.01 fold to about 100 fold, about 0.05 fold to about 0.1 fold, about 0.05 fold to about 0.5 fold, about 0.05 fold to about 1 fold, about 0.05 fold to about 2 fold, about 0.05 fold to about 5 fold, about 0.05 fold to about 10 fold, about 0.05 fold to about 20 fold, about 0.05 fold to about 50 fold, about 0.05 fold to about 100 fold, about 0.1 fold to about 0.5 fold, about 0.1 fold to about 1 fold, about 0.1 fold to about 2 fold, about 0.1 fold to about 5 fold, about 0.1 fold to about 10 fold, about 0.1 fold to about 20 fold, about 0.1 fold to about 50 fold, about 0.1 fold to about 100 fold, about 0.5 fold to about 1 fold, about 0.5 fold to about 2 fold, about 0.5 fold to about 5 fold, about 0.5 fold to about 10 fold, about 0.5 fold to about 20 fold, about 0.5 fold to about 50 fold, about 0.5 fold to about 100 fold, about 1 fold to about 2 fold, about 1 fold to about 5 fold, about 1 fold to about 10 fold, about 1 fold to about 20 fold, about 1 fold to about 50 fold, about 1 fold to about 100 fold, about 2 fold to about 5 fold, about 2 fold to about 10 fold, about 2 fold to about 20 fold, about 2 fold to about 50 fold, about 2 fold to about 100 fold, about 5 fold to about 10 fold, about 5 fold to about 20 fold, about 5 fold to about 50 fold, about 5 fold to about 100 fold, about 10 fold to about 20 fold, about 10 fold to about 50 fold, about 10 fold to about 100 fold, about 20 fold to about 50 fold, about 20 fold to about 100 fold, or about 50 fold to about 100 fold. In some embodiments, the amount of the at least one additional immunosuppressant administered to the subject is decreased by at least about 0.01 fold, about 0.05 fold, about 0.1 fold, about 0.5 fold, about 1 fold, about 2 fold, about 5 fold, about 10 fold, about 20 fold, about 50 fold, or about 100 fold. In some embodiments, the amount of the at least one additional immunosuppressant administered to the subject is decreased by at least at least about 0.01 fold, about 0.05 fold, about 0.1 fold, about 0.5 fold, about 1 fold, about 2 fold, about 5 fold, about 10 fold, about 20 fold, or about 50 fold. In some embodiments, the amount of the at least one additional immunosuppressant administered to the subject is decreased by at least at most about 0.05 fold, about 0.1 fold, about 0.5 fold, about 1 fold, about 2 fold, about 5 fold, about 10 fold, about 20 fold, about 50 fold, or about 100 fold. In some embodiments, the amount of the at least one additional immunosuppressant administered to the subject is about 0.1 mg, 0.2 mg, 0.5 mg, 1.0 mg, 1.5 mg, 2.0 mg, 2.5 mg, 3.0 mg, 3.5 mg, 4.0 mg, 5.0 mg, 6.0 mg, 7.0 mg, 8.0 mg, 9.0 mg, 10.0 mg, 15.0 mg, 20.0 mg, 50.0 mg, 100.0 mg, or more per 1 kg of the weight of the subject. In some embodiments, the at least one additional immunosuppressant is rabbit anti-thymocyte globulin. In some embodiments, the amount of the rabbit anti-thymocyte globulin administered to the subject is about 0.1 mg, 0.2 mg, 0.5 mg, 1.0 mg, 1.5 mg, 2.0 mg, 2.5 mg, 3.0 mg, 3.5 mg, 4.0 mg, 5.0 mg, 6.0 mg, 7.0 mg, 8.0 mg, 9.0 mg, 10.0 mg, 15.0 mg, 20.0 mg, 50.0 mg, 100.0 mg, or more per 1 kg of the weight of the subject. In some embodiments, the at least one additional immunosuppressant is tacrolimus. In some embodiments, the amount of the tacrolimus administered to the subject is about 0.1 mg, 0.2 mg, 0.5 mg, 1.0 mg, 1.5 mg, 2.0 mg, 2.5 mg, 3.0 mg, 3.5 mg, 4.0 mg, 5.0 mg, 6.0 mg, 7.0 mg, 8.0 mg, 9.0 mg, 10.0 mg, 15.0 mg, 20.0 mg, 50.0 mg, 100.0 mg, or more per 1 kg of the weight of the subject. In some embodiments, the at least one additional immunosuppressant is prednisone. In some embodiments, the amount of the prednisone administered to the subject is about 0.1 mg, 0.2 mg, 0.5 mg, 1.0 mg, 1.5 mg, 2.0 mg, 2.5 mg, 3.0 mg, 3.5 mg, 4.0 mg, 5.0 mg, 6.0 mg, 7.0 mg, 8.0 mg, 9.0 mg, 10.0 mg, 15.0 mg, 20.0 mg, 50.0 mg, 100.0 mg, or more per 1 kg of the weight of the subject.

Treatment

Described herein, in some embodiments, are methods of preventing or decreasing rejection of the transplanted organ in the subject organ recipient without inducing GvHD by establishing a long-term chimerism in the subject. In some embodiments, the methods comprise administering (e.g. infusion) the population of cells described herein to the subject organ recipient. In some cases, the population of cells can be hematopoietic stem cells or hematopoietic progenitor cells. In some cases, the population of cells can be myeloid cells. In some embodiments, the population of cells can be immune cells derived from the hematopoietic stem cells or hematopoietic progenitor cells. In some embodiments, the immune cells can be any one of monocyte, T cell, B cell, dendritic cell, macrophage, NK cell, or NKT cell. In some embodiments, the population of cells can exhibit specific marker associated with hematopoietic stem cells, hematopoietic progenitor cells, or differentiated immune cells. Exemplary marker can include CD34, CD2, CD3, CD11b, CD11c, CD14, CD16, CD19, CD24, CD56, CD66b, CD235, CD38, CD45RA, CD90, or CD49f. In some cases, the population of cells described herein are CD34+ cells (e.g. cells that express CD34 as the cell marker). In some embodiments, the population of cells described herein can comprise only one type of cell. In some embodiments, the population of cells described herein can comprise more than one type of cell. In some embodiments, the population of cells described herein can comprise cells determined based on cell marker. For example, the population of cells described herein can be CD34+ cells.

In some embodiments, the population of cells can be administered to the subject at least ten, nine, eight, seven, six, five, four, three, two, or one day before the subject receiving the organ transplantation. In some embodiments, the population of cells can be administered to the subject at the same time as the subject is receiving the organ transplantation. In some embodiments, the population of cells can be administered to the subject at least one, two, three, four, five, six, seven, eight, nine, ten, 11, 12, 13, 14, 15, or more days after the subject has received the organ transplantation. In some embodiments, the population of cells can be administered to the subject at least one, two, three, four, five, six, seven, eight, nine, ten, or more weeks after the subject has received the organ transplantation. In some embodiments, the population of cells can be administered to the subject at least one, two, three, four, five, six, seven, eight, nine, ten, eleven, or more months after the subject has received the organ transplantation. In some embodiments, the population of cells can be administered to the subject at least one, two, three, four, five, six, seven, eight, nine, ten, or more years after the subject has received the organ transplantation. In some embodiments, the population of cells can be administered to the subject daily, weekly, monthly, yearly, or any time interval as deemed necessary. In some embodiment, the population of cells can be administered to the subject before LGvHR arises in the subject. In some embodiment, the population of cells can be administered to the subject at least at least one, two, three, four, five, six, seven, eight, nine, ten, or more days before LGvHR arises in the subject. In some embodiment, the population of cells can be administered to the subject during or after LGvHR in the subject. In some embodiment, the population of cells can be administered to the subject during the peak of LGvHR in the subject (e.g. day 1-30 after organ transplantation, including day seven, eight, nine, ten, 11, 12, 13, 14, 15, 16 days after organ transplantation).

In some embodiments, the amount of the population of cells to be administered to the subject can be determined by the subject's weight. For example, at least 1×10^6 cells per kg of the weight of the subject can be administered to the subject. In some embodiments, no more than 1×10^3 cells per kg, 1×10^4 cells per kg, 1×10^5 cells per kg, 1×10^6 cells per kg, or 1×10^7 cells per kg of the population of cells are administered to the subject organ recipient. In some embodiments, at least 1×10^3 cells per kg, 1×10^4 cells per kg, 1×10^5 cells per kg, 1×10^6 cells per kg, 2×10^6 cells per kg, 3×10^6 cells per kg, 4×10^6 cells per kg, 5×10^6 cells per kg, or 1×10^7 cells per kg of the population of cells are administered to the subject organ recipient. In some cases, no more than 1×10^3 CD34+ cells per kg, 1×10^4 CD34+ cells per kg, 1×10^5 CD34+ cells per kg, 1×10^6 CD34+ cells per kg, or 1×10^7 CD34+ cells per kg of the population of CD34+ cells are administered to the subject organ recipient. In some embodiments, at least 1×10^3 CD34+ cells per kg, 1×10^4 CD34+ cells per kg, 1×10^5 CD34+ cells per kg, 1×10^6 CD34+ cells per kg, 2×10^6 CD34+ cells per kg, 3×10^6 CD34+ cells per kg, 4×10^6 CD34+ cells per kg, 5×10^6 CD34+ cells per kg, or 1×10^7 CD34+ cells per kg of the population of CD34+ cells are administered to the subject organ recipient.

In some embodiments, the number of the population of cells administered or the frequency of the administration of the population of cells can be determined based on detecting the number of the administered cells detected in the subject, which indicates the level of chimerism in the subject. For example, the number of the population of cells administered or the frequency of the administration of the population of cells can be increased if the B cell, T cell, or monocyte chimerism in the subject is not greater than a certain percentage by a predetermined period of time after administration of the initial population of cells.

In some embodiments, the methods of administering the population of cells described herein can be part of the treatment options for treating Short Bowel Syndrome (SBS) due to: trauma (multiple resections/explorations and/or vascular abdominal trauma SMA/SMV injuries), Gastroschisis, *Volvulus*, Necrotizing Enterocolitis, Intestinal Atresia, Crohn's Disease, Hirschprung's Disease, Chronic Intestinal Pseudo-Obstruction, Malabsorption, Microvillus Inclusion Disease, Tufting Enteropathy, Complete portomesenteric thrombosis with cirrhosis, Slow-growing, low-malignancy potential tumors infiltrating mesenteric root, Gardner's Syndrome, Familial Adenomatous Polyposis, Desmoid Tumor with Intra-Abdominal Infiltration, Endocrine Tumors, Re-transplant candidates who lost the first graft to rejection or subjects who have higher risk of toxicity from chronic long term immunosuppression (i.e., subjects with chronic kidney disease).

Cell Selection and Isolation

Described herein are methods for establishing a long-term chimerism in the subject to decrease or prevent rejection of the transplanted organ without inducing GvHD by administering a population of cells to the subject. In some cases, the population of cells can be obtained from any source such as cell culture or from a donor. In some embodiments, the populations of cells can be obtained from the same donor who also donates the organ to the subject. In some instances, the population of cells can be obtained from a donor who is not the donor of the organ. In some embodiments, the population of cells can be obtained for a cadaveric source.

In some cases, the population of cells can be obtained from processing donor vertebral body (VB) bones. Soft tissue of the VB bones can be removed from the outside of the spine with sterilized osteotomes. Pedicles and spinous process are removed from VBs using a bone saw. VBs can be separated by cutting through the discs, and soft tissue and discs are removed from each VB using sterilized osteotomes, knives, scissors, and scalpels. Identify any visible anatomical pathologies present, including bone spurs, degenerative discs, herniated discs, and atrophic bone marrow. All VBs from the same donor are cut into small pieces (~2-3 $cm^2$) and ground with a bone grinder in media containing Plasmalyte, human serum albumin (HSA) (2.5%), Heparin (10 U/mL), and Benzonase (3 U/mL). Bone marrow is separated from the grindings using sterile, disposable bone marrow collection kit. For example, four 600 mL bags of bone marrow from the bone marrow collection kit are centrifuged for 15 minutes at 1500 rpm. After centrifugation, a waste bag is welded onto each of the four centrifuged bags and the supernatant is removed using a plasma extractor. Concentrated BM is combined from each of the four 600 mL bags into a 2L bag, and each small bag is rinsed with 10 mL of media (Plasmalyte, 2.5% HSA, 10 U/mL Heparin). Two 250 μL samples are pulled from the concentrated BM, diluted 1:4 in media (Plasmalyte, 2.5% HSA, 10 U/mL Heparin). One sample is used for the CFU assay, and one is used from Sysmex testing and flow cytometry. After testing of bone marrow is complete, additional steps can be taken to select for the population of cells (e.g. CD34+ cells) to be administered to the subject. The bone marrow can be incubated with an antibody that is conjugated with super-paramagnetic particles. The unbound antibody is washed from the cell suspension containing the antibody bound target cells, which is then passed through a column in which strong magnetic gradients are generated. The column retains the magnetically labeled bound cells, while unwanted cells flow through the column and into the negative fraction bag. After the system performs several washing steps, the magnetic field is removed from the column and the separated bound cells (e.g. CD34+ cells bound by CD34 monoclonal antibody conjugated to the super-paramagnetic particles) are released and eluted into the cell collection bag. Following this selection, once release criteria are met, in compliance with purity and recovery limits (via flow cytometric acquisition and analysis methodologies, using flow cytometry to conduct enumeration of the targeted cells) cells are cryopreserved. Packaged cells can be cryopreserved prior to administration to the subject.

CD34+ Cell Selection

In some embodiments, the methods described herein comprise isolation (e.g. processing) of CD34+ cells from bone marrow or bone marrow derivative. In some cases, the bone marrow or bone marrow derivative can be fresh (e.g. never frozen) or thawed from being previously frozen. In some embodiments, the bone marrow or bone marrow derivative can be ground. In some embodiments, ground bone marrow or bone marrow cells can be contacted with a stabilization buffer. In some embodiments, the disclosure comprises a stabilization buffer comprising: at least 5 U/ml of an anticoagulant; and more than 3 U/ml of a nuclease. In some embodiments, the stabilization buffer comprises more than about 5 U/ml of a nuclease. In some embodiments, the stabilization buffer comprises more than about 10 U/ml of a nuclease. In some embodiments, the stabilization buffer comprises more than about 15 U/ml of a nuclease. In some embodiments, the stabilization buffer comprises more than about 20 U/ml of a nuclease. In some embodiments, the stabilization buffer comprises about 20 U/ml of a nuclease. In some embodiments, the nuclease is Benzonase® or Denarase®. In some embodiments, the stabilization buffer further comprises more than about 10 U/ml of an anticoagulant. In some embodiments, the stabilization buffer further comprises about 10 U/ml of an anticoagulant. In some embodiments, the anticoagulant is heparin. In some embodiments, the stabilization buffer further comprises human serum albumin (HSA). In some embodiments, the stabilization buffer comprises 0.5% HSA.

In some embodiments, the stabilization buffer comprises nuclease. In some embodiments, the nuclease is Benzonase® or Denarase®. In some embodiments, the stabilization buffer comprises nuclease at about 3 U/ml, 4 U/ml, 5 U/ml, 6 U/ml, 7 U/ml, 8 U/ml, 9 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml, 22 U/ml, 23 U/ml, 24 U/ml, 25 U/ml, 26 U/ml, 27 U/ml, 28 U/ml, 29 U/ml, 30 U/ml, 50 U/ml, 100 U/ml, 200 U/ml, or more U/ml. In some embodiments, the stabilization buffer comprises an anticoagulant. In some cases, the anticoagulant is Heparin.

In some instances, the stabilization buffer comprises anticoagulant at about 0.1 U/ml, 0.2 U/ml, 0.3 U/ml, 0.4 U/ml, 0.5 U/ml, 0.6 U/ml, 0.7 U/ml, 0.8 U/ml, 0.9 U/ml, 1.0 U/ml, 2.0 U/ml, 3.0 U/ml, 4.0 U/ml, 5.0 U/ml, 6.0 U/ml, 7.0 U/ml, 8.0 U/ml, 9.0 U/ml, 10 U/ml, 11 U/ml, 12 U/ml, 13 U/ml, 14 U/ml, 15 U/ml, 16 U/ml, 17 U/ml, 18 U/ml, 19 U/ml, 20 U/ml, 21 U/ml, 22 U/ml, 23 U/ml, 24 U/ml, 25 U/ml, 26 U/ml, 27 U/ml, 28 U/ml, 29 U/ml, 30 U/ml, 50 U/ml, 100 U/ml, 200 U/ml, or more U/ml.

In some embodiments, the stabilization buffer comprises about 0.001%, 0.002%, 0.003%, 0.004%, 0.005%, 0.01%, 0.02%, 0.03%, 0.04%, 0.05% HSA, 0.1% HSA, 0.2% HSA, 0.3% HSA, 0.4% HSA, 0.5% HSA, 0.6% HSA, 0.7% HSA, 0.8% HSA, 0.9% HSA, 1.0% HSA, 1.5% HSA, 2% HSA, 2.5% HSA, 5% HSA, 10% HSA, 20% HSA, or more HSA.

Described herein, in some embodiments, is a method of processing bone marrow to obtain bone marrow cells. In some embodiments, the method comprises contacting the bone marrow or the bone marrow cells with the stabilization buffer described herein.

Another aspect of the present disclosure comprises a method for processing a population of CD34+ cells comprised in bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or derivative thereof from the bone or bone fragment; and contacting the bone marrow or derivative thereof with a stabilization buffer, wherein the stabilization buffer comprises more than about 3 U/ml of a nuclease; performing a CD34+ cell isolation assay to generate a cellular composition comprising the population of CD34+ cells, wherein the composition comprising the population of CD34+ cells comprise at least about 80,000 CD34+ cells/750 ul of the bone marrow or the derivative thereof contacted with the stabilization buffer.

In some embodiments, the stabilization buffer prevents formation of aggregates of the bone marrow cells. In some instances, the bone marrow cells contacted and suspended in the stabilization buffer can be isolated by attaching to antibody such as a conjugated antibody. For example, bone marrow cells expressing CD34+ can be isolated and enriched by contacting the bone marrow cells with the CD34 antibody conjugated with iron, where the bone marrow cells expressing CD34 are then trapped a magnetic separation column (e.g. "CliniMACS®"). The bone marrow cells not expressing CD34 are can be washed away. The trapped CD34+ bone marrow cells can be harvested by removing the magnetic field and eluting the targeted CD34+ bone marrow cells. Such approach does not require isolating the bone marrow cells with a Ficoll gradient.

Aspect described in the present disclosure comprises a method for processing a population of CD34+ cells obtained from bone marrow or a derivative thereof, wherein the bone marrow or the derivative thereof is derived from a deceased donor, the method comprising: obtaining a bone or bone fragment from a deceased donor, optionally, processing the bone into bone fragments; extracting the bone marrow or derivative thereof from the bone or bone fragment; and contacting the bone marrow or derivative thereof with a stabilization buffer, wherein the stabilization buffer comprises more than about 3 U/ml of a nuclease; performing a CD34+ cell isolation assay to generate a cellular composition comprising the population of CD34+ cells, wherein the composition comprising the population of CD34+ cells comprise at least about 80,000 CD34+ cells/750 μl of the bone marrow or the derivative thereof contacted with the stabilization buffer. In some embodiments, the at least about 80,000 CD34+ cells/750 μl of the bone marrow or the derivative thereof contacted with the stabilization buffer comprise at least 70% viable CD34+ cells. In some embodiments, the at least about 80,000 CD34+ cells/750 μl of the bone marrow or the derivative thereof contacted with the stabilization buffer comprise at least 80% viable CD34+ cells. In some embodiments, the at least about 80,000 CD34+ cells/750 μl of the bone marrow or the derivative thereof contacted with the stabilization buffer comprise at least 90% viable CD34+ cells.

In some embodiments, processing or contacting the bone marrow or bone marrow cells described herein with the stabilization buffer increases the yield of the bone marrow cells obtained from the methods described herein compared to the yield of the bone marrow cells processed in the absence of the stabilization buffer. In some instances, processing or contacting the bone marrow or bone marrow cells described herein with the stabilization buffer increases the yield of the bone marrow cells by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to yield of bone marrow cells processed in the absence of the stabilization buffer. In some embodiments, processing or contacting the bone marrow or bone marrow cells described herein with the stabilization buffer increases the viability of the bone marrow cells obtained from the methods described herein compared to the viability of the bone marrow cells processed in the absence of the stabilization buffer. In some instances, processing or contacting the bone marrow or bone marrow cells described herein with the stabilization buffer increases the viability of the bone marrow cells by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to viability of bone marrow cells processed in the absence of the stabilization buffer.

In some embodiments, processing or contacting the bone marrow or bone marrow cells described herein with the stabilization buffer increases the number of CD34+ bone marrow cells compared to the number of CD34+ bone marrow cells processed in the absence of the stabilization buffer. In some cases, the number of CD34+ bone marrow obtained from processing with the stabilization buffer is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD34+ bone marrow obtained from processing in the absence of stabilization buffer.

In some embodiments, processing or contacting the bone marrow or bone marrow cells described herein with the stabilization buffer increases the number of CD45+ bone marrow cells compare to the number of CD45+ bone marrow cells processed in the absence of the stabilization buffer. In some cases, the number of CD45+ bone marrow obtained from processing with the stabilization buffer is increased by at least about 10%, 20%, 30%, 40%, 50%, 60%, 70%, 80%. 90%, 100%, 2 fold, 3 fold, 4 fold, 5 fold, 10 fold, 20 fold, 50 fold, or more compared to the number of CD45+ bone marrow obtained from processing in the absence of stabilization buffer.

In some embodiments, cellular compositions comprising CD34+ cells derived from bone marrow samples processed with the stabilization buffers described herein have an increased amount of CD34+ cells, as compared to cellular compositions generated from other CD34+ isolation methods. In some embodiments. The amount of CD34+ cells are isolated from the bone marrow samples contacted with the stabilization buffers described herein is at least about 70,000 CD34+ cells/750 ul of bone marrow or a derivative thereof contacted with the stabilization buffers described herein. In some embodiments, the amount of CD34+ cells are isolated from the bone marrow samples contacted with the stabilization buffers described herein is at least about 70,000 cells/750 ul to about 100,000 cells/750 ul. In some embodiments, the amount of CD34+ cells are isolated from the bone marrow samples contacted with the stabilization buffers described herein is at least about 70,000 cells/750 ul to about 75,000 cells/750 ul, about 70,000 cells/750 ul to about 80,000 cells/750 ul, about 70,000 cells/750 ul to about 85,000 cells/750 ul, about 70,000 cells/750 ul to about 90,000 cells/750 ul, about 70,000 cells/750 ul to about 95,000 cells/750 ul, about 70,000 cells/750 ul to about 100,000 cells/750 ul, about 75,000 cells/750 ul to about 80,000 cells/750 ul, about 75,000 cells/750 ul to about 85,000 cells/750 ul, about 75,000 cells/750 ul to about 90,000 cells/750 ul, about 75,000 cells/750 ul to about 95,000 cells/750 ul, about 75,000 cells/750 ul to about 100,000 cells/750 ul, about 80,000 cells/750 ul to about 85,000 cells/750 ul, about 80,000 cells/750 ul to about 90,000 cells/750 ul, about 80,000 cells/750 ul to about 95,000 cells/750 ul, about 80,000 cells/750 ul to about 100,000 cells/750 ul, about 85,000 cells/750 ul to about 90,000 cells/750 ul, about 85,000 cells/750 ul to about 95,000 cells/750 ul, about 85,000 cells/750 ul to about 100,000 cells/750 ul, about 90,000 cells/750 ul to about 95,000 cells/750 ul, about 90,000 cells/750 ul to about 100,000 cells/750 ul, or about 95,000 cells/750 ul to about 100,000 cells/750 ul. In some embodiments, the amount of CD34+ cells are isolated from the bone marrow samples contacted with the stabilization buffers described herein is at least about 70,000 cells/750 ul, about 75,000 cells/750 ul, about 80,000 cells/750 ul, about 85,000 cells/750 ul, about 90,000 cells/750 ul, about 95,000 cells/750 ul, or about 100,000 cells/750 ul. In some embodiments, the amount of CD34+ cells are isolated from the bone marrow samples contacted with the stabilization buffers described herein is at least at least about 70,000 cells/750 ul, about 75,000 cells/750 ul, about 80,000 cells/750 ul, about 85,000 cells/750 ul, about 90,000 cells/750 ul, or about 95,000 cells/750 ul. In some embodiments, the amount of CD34+ cells are isolated from the bone marrow samples contacted with the stabilization buffers described herein is at least at most about 75,000 cells/750 ul, about 80,000 cells/750 ul, about 85,000 cells/750 ul, about 90,000 cells/750 ul, about 95,000 cells/750 ul, or about 100,000 cells/750 ul.

In some embodiments, the CD34+ cells derived from bone marrow samples processed with the stabilization buffers described herein also exhibit higher viability as compared to cellular compositions generated from known CD34+ isolation methods.

In some embodiments, the amount of CD34+ cells are isolated from the bone marrow samples contacted with the stabilization buffers described herein comprise a percent viability of at least about 70% to about 95%. In some embodiments, the amount of CD34+ cells are isolated from the bone marrow samples contacted with the stabilization buffers described herein comprise a percent viability of at least about 70% to about 95%. In some embodiments, the amount of CD34+ cells are isolated from the bone marrow samples contacted with the stabilization buffers described herein comprise a percent viability of at least about 70% to about 75%, about 70% to about 80%, about 70% to about 85%, about 70% to about 90%, about 70% to about 95%, about 75% to about 80%, about 75% to about 85%, about 75% to about 90%, about 75% to about 95%, about 80% to about 85%, about 80% to about 90%, about 80% to about 95%, about 85% to about 90%, about 85% to about 95%, or about 90% to about 95%. In some embodiments, the amount of CD34+ cells are isolated from the bone marrow samples contacted with the stabilization buffers described herein comprise a percent viability of at least about 70%, about 75%, about 80%, about 85%, about 90%, or about 95%. In some embodiments, the amount of CD34+ cells are isolated from the bone marrow samples contacted with the stabilization buffers described herein comprise a percent viability of at least at least about 70%, about 75%, about 80%, about 85%, or about 90%. In some embodiments, the amount of CD34+ cells areolated from the bone marrow samples contacted with the stabilization buffers described herein comprise a percent viability of at least at most about 75%, about 80%, about 85%, about 90%, or about 95%.

In an aspect of the present disclosure, a method is provided for selecting CD34 expressing (CD34+) cells from deceased donor bone marrow using density reduced Ficoll and an immunomagnetic CD34+ cell isolation kit. Cell isolation using density reduced Ficoll prior to CD34 selection can be beneficial to obtain high purity and viability CD45/CD34+ cells from freshly prepared deceased donor bone marrow. On the other hand, Ficoll at conventional density has been found to be optimal for CD45/CD34+ cell selection from thawed cryopreserved deceased donor bone marrow.

Vertebral sections obtained from a recently deceased donor can be processed similarly as described above. Thus, in one embodiment, the bone is cleaned of all soft tissue and then cut into small pieces that were immediately submerged into 500 ml of grinding media. The grinding media can be PLASMA-LYTE™ A injection pH 7.4, multiple electrolytes, injection type 1 USP (PLASMA-LYTE™) containing 2.5% human serum albumin (HSA), 3 U/ml Denarase, and 10 U/ml heparin. The sectioned VB are ground using a bone grinder, filtered and rinsed with rinse media (such as PLASMA-LYTE™ with 2.5% HSA). The entire cell suspension is centrifuged to concentrate cells to $2\text{-}3\times10^8$/ml and the cell concentration is extracted. A portion or all of the resulting BM preparation can be used immediately for CD34 selection, while the remainder can be prepared for cryopreservation. The cryopreserved portion involves adding a final concentration of 10% DMSO and 5% HSA to the BM cells and bringing the preparation to −86° C., either by passive cooling or by controlled cooling at a rate of approximately −1° C./min, after which the cryopreserved portion is plunged into liquid nitrogen.

For selection of CD34+ cells, either the newly processed BM preparation is used or a previously cryopreserved portion is thawed for use. Ficoll-Paque PLUS is added to the BM preparation to separate the desired CD34+ cell component of the bone marrow. It has been found for cell selection from cryopreserved bone marrow that the conventional density for the Ficoll of 1.077 g/ml produces acceptable results. However, in one aspect of the present disclosure, for cell selection from freshly prepared deceased donor bone marrow the Ficoll density is reduced from the conventional density. In particular, the density is reduced by mixing Ficoll-Paque PLUS (density 1.077 g/mL, GE Company) with Plasma Lyte-A Injection pH 7.4 (Baxter Healthcare 2B2544X) in specific proportions to obtain an overall density of less than 1.077 g/ml, particularly 1.063-1.052 g/ml. In one specific embodiment, the density of 1.063 g/ml was found to be optimal for isolation of CD34+ cells, taking into account quantity, viability and purity of the CD34+ cells.

In one embodiment, 5 ml of the 1.063 g/ml density Ficoll solutions is pipetted into 15-ml centrifuge tubes, and the BM solution generated from VBs of deceased donors is carefully layered over the Ficoll gradient. The tubes are centrifuged for 30 min at 400× g without break at room temperature. After centrifugation, buffy coat cells are harvested carefully, and the cells are washed in phosphate-buffered saline (PBS) containing 0.5% HSA and 2 mM Ethylenediaminetetraacetic acid (EDTA) (MACS buffer, Miltenyi). In one specific embodiment, centrifugation is performed for 5 min at 400× g, and the resulting cell pellets are resuspended in 10 ml PBS, followed by a second centrifugation for 5 min at 400× g.

Nucleated cells in the isolated buffy coat can be counted using a Sysmex XP-300. A Cellometer Vision (Nexcellom) or flow cytometer can be used to determine cell counts of purified CD34 cells. 20 microliters of AOPI can be added to 20 microliters of cells and after mixing total viable cells can be determined. The CD34+ cells can be selected by a positive immune separation method using a CliniMAX system (Miltenyi, Bergisch Gladbach, Germany) or an EasySep CD34 kit (Stemcell Technologies, Vancouver, BC, Canada) in accordance with the protocol of the manufacturer. From testing at various Ficoll densities it has been surprisingly determined that the lower Ficoll density contemplated in the present disclosure (i.e., 1.063-1.052 gm/ml vs. the conventional 1.077 gm/ml density) leads to more optimum cell recovery. Optimization is based on purity, viability and yield of selected CD34 cells. A target of >90% purity and >90% viable CD34+ cells are preferred. While lower Ficoll densities resulted in greater purity and fewer dead cells, it was surprisingly found that a greater portion of the CD34+ cells present in the deceased donor whole bone marrow before selection are lost using the lower Ficoll densities to prepare buffy coat. Thus, the high viability and purity of CD45/CD34+ cells achieved at the conventional Ficoll density gradient also leads to a large loss in yield (approximately 60% loss of input CD34+ cells).

Thus, in accordance with one aspect of the present disclosure, for freshly prepared the optimal density of Ficoll for selection of CD45/CD34+ cells at >90% purity and viability is less than 1.077 and particularly 1.063-1.052. This Ficoll density provides a higher yield of CD45/CD34+ cells with similar purity and cell viability to the conventional Ficoll density approach.

In another aspect of the present disclosure, the CD34+ cells can be initially acquired from a freshly prepared deceased donor bone marrow using the reduced density Ficoll-Paque described above. The BM can be cryogenically frozen and then the CD34+ cells can be acquired later using conventional density Ficoll-Paque. This approach essentially allows selective recovery of cells from deceased donor bone marrow—either before freezing using the modified Ficoll density or after freezing and thawing using conventional Ficoll density.

Pharmaceutical Compositions

In some cases, the population of cells described herein (e.g. the population of cells to be administered to the subject) can be formulated into pharmaceutical composition. In some cases, the pharmaceutical composition comprising the population of cells described herein can be administered to a subject by multiple administration routes, including but not limited to, parenteral, oral, buccal, rectal, sublingual, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration. In some cases, the pharmaceutical composition and formulations described herein are administered to a subject by intravenous, subcutaneous, and intramuscular administration. In some cases, the pharmaceutical composition and formulations described herein are administered to a subject by intravenous administration. In some cases, the pharmaceutical composition and formulations described herein are administered to a subject by infusion.

The methods described herein can be considered useful as pharmaceutical compositions for administration to a subject in need thereof. Pharmaceutical compositions can comprise at least one population of cells described herein and one or more pharmaceutically acceptable carriers, diluents, excipients, stabilizers, dispersing agents, suspending agents, and/or thickening agents. The pharmaceutical composition can further comprise buffers, antibiotics, steroids, carbohydrates, drugs (e.g., chemotherapy drugs), radiation, polypeptides, chelators, adjuvants and/or preservatives.

Pharmaceutical compositions can be formulated using one or more physiologically-acceptable carriers comprising excipients and auxiliaries. Formulation can be modified depending upon the route of administration chosen. Pharmaceutical compositions comprising a conjugate as described herein can be manufactured, for example, by lyophilizing the conjugate, mixing, dissolving, emulsifying, encapsulating or entrapping the conjugate. Pharmaceutical compositions comprising a conjugate as described herein can be manufactured, for example, by lyophilizing the conjugate, mixing, dissolving, emulsifying, encapsulating or entrapping the conjugate. The pharmaceutical compositions can also include the cells described herein in a free-base form or pharmaceutically-acceptable salt form.

Methods for formulation of the pharmaceutical compositions can include formulating any of the populations of cells described herein with one or more inert, pharmaceutically-acceptable excipients or carriers to form a solid, semi-solid, or liquid composition. Solid compositions can include, for example, powders, tablets, dispersible granules and capsules, and in some aspects, the solid compositions further contain nontoxic, auxiliary substances, for example wetting or emulsifying agents, pH buffering agents, and other pharmaceutically-acceptable additives. Alternatively, the compositions described herein can be lyophilized or in powder form for re-constitution with a suitable vehicle, e.g., sterile pyrogen-free water, before use Pharmaceutical compositions as described herein can comprise more than one active compound as necessary for the particular indication being treated. The active compounds can have complementary activities that do not adversely affect each other. For example, the pharmaceutical composition can also comprise at least one of the immunosuppressant described herein.

The pharmaceutical compositions and formulations can be sterilized. Sterilization can be accomplished by filtration through sterile filtration.

The pharmaceutical compositions described herein can be formulated for administration as an injection. Non-limiting examples of formulations for injection can include a sterile suspension, solution or emulsion in oily or aqueous vehicles. Suitable oily vehicles can include, but are not limited to, lipophilic solvents or vehicles such as fatty oils or synthetic fatty acid esters, or liposomes. Aqueous injection suspensions can contain substances which increase the viscosity of the suspension. The suspension can also contain suitable stabilizers. Injections can be formulated for bolus injection or continuous infusion.

For parenteral administration, the populations of cells can be formulated in a unit dosage injectable form (e.g., a solution, suspension, emulsion) in association with a pharmaceutically acceptable parenteral vehicle. Such vehicles can be inherently nontoxic, and non-therapeutic. A vehicle can be water, saline, Ringer's solution, dextrose solution, and 5% human serum albumin. Nonaqueous vehicles such as fixed oils and ethyl oleate can also be used. Liposomes can be used as carriers. The vehicle can contain minor amounts of additives such as substances that enhance isotonicity and chemical stability (e.g., buffers and preservatives).

Pharmaceutical formulations of the compositions described herein can be prepared for storage by mixing with a pharmaceutically acceptable carrier, excipient, and/or a stabilizer. This formulation can be an aqueous solution. Acceptable carriers, excipients, and/or stabilizers can be nontoxic to recipients at the dosages and concentrations used. Acceptable carriers, excipients, and/or stabilizers can include buffers such as phosphate, citrate, and other organic acids; antioxidants including ascorbic acid and methionine; preservatives, polypeptides; proteins, such as serum albumin or gelatin; hydrophilic polymers; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

Kits and Article of Manufacture

Disclosed herein, in certain embodiments, are kits and articles of manufacture for use with one or more methods described herein. In some cases, the kits or articles of manufacture comprise the population of cells or the pharmaceutical compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, a kit includes a suitable packaging material to house the contents of the kit. In some cases, the packaging material is constructed by well-known methods, preferably to provide a sterile, contaminant-free environment. The packaging materials employed herein can include, for example, those customarily utilized in commercial kits sold for use with nucleic acid sequencing systems. Exemplary packaging materials include, without limitation, glass, plastic, paper, foil, and the like, capable of holding within fixed limits a component set forth herein.

The packaging material can include a label which indicates a particular use for the components. The use for the kit that is indicated by the label can be one or more of the methods set forth herein as appropriate for the particular combination of components present in the kit.

Instructions for use of the packaged reagents or components can also be included in a kit. The instructions will typically include a tangible expression describing reaction parameters, such as the relative amounts of kit components and sample to be admixed, maintenance time periods for reagent/sample admixtures, temperature, buffer conditions, and the like.

It will be understood that not all components necessary for a particular reaction need be present in a particular kit. Rather one or more additional components can be provided from other sources. The instructions provided with a kit can identify the additional component(s) that are to be provided and where they can be obtained.

Definitions

Use of absolute or sequential terms, for example, "will," "will not," "shall," "shall not," "must," "must not," "first," "initially," "next," "subsequently," "before," "after," "lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

As used herein, "or" can refer to "and", "or," or "and/or" and can be used both exclusively and inclusively. For example, the term "A or B" can refer to "A or B", "A but not B", "B but not A", and "A and B". In some cases, context can dictate a particular meaning.

Any systems, methods, software, and platforms described herein are modular. Accordingly, terms such as "first" and "second" do not necessarily imply priority, order of importance, or order of acts.

The term "about" when referring to a number or a numerical range means that the number or numerical range referred to is an approximation within experimental variability (or within statistical experimental error), and the number or numerical range can vary from, for example, from 1% to 15% of the stated number or numerical range. In examples, the term "about" refers to ±10% of a stated number or value.

The terms "increased", "increasing", or "increase" are used herein to generally mean an increase by a statically significant amount. In some aspects, the terms "increased," or "increase," mean an increase of at least 10% as compared to a reference level, for example an increase of at least about 10%, at least about 25%, or at least about 30%, or at least about 40%, or at least about 50%, or at least about 60%, or at least about 70%, or at least about 80%, or at least about 90% or up to and including a 100% increase or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold or more as compared to a reference level.

The terms, "decreased", "decreasing", or "decrease" are used herein generally to mean a decrease by a statistically significant amount. In some aspects, "decreased" or "decrease" means a reduction by at least 10% as compared to a reference level, for example a decrease by at least about 25%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 25%, at least 30%, at least 40% or more, and is preferably down to a level accepted as within the range of normal for an individual without a given disease.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. A component is "pharmaceutically acceptable" in the sense of being compatible with the other ingredients of a pharmaceutical formulation. It can also be suitable for use in contact with the tissue or organ of humans and non-human mammals without excessive toxicity, irritation, allergic response, immunogenicity, or other problems or complications, commensurate with a reasonable benefit/risk ratio.

The term "pharmaceutical composition" refers to the systems or a mixture of the systems or compositions comprising each component of the systems disclosed herein with other chemical components, such as diluents or carriers. The pharmaceutical composition can facilitate administration of the systems or components of the systems to the subject. Multiple techniques of administering a compound exist in the art including, but not limited to, oral, injection, aerosol, parenteral, and topical administration.

While preferred embodiments of the present invention have been shown and described herein, it can be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions can now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following illustrative examples are representative of embodiments of the stimulation, systems, and methods described herein and are not meant to be limiting in any way.

Example 1. T Cell Chimerism and Lymphohematopoietic GvH Responses after Visceral Transplantation The human intestine contains an enormous lymphoid mass. Consequently, ITx results in significant replacement of recipient by donor lymphoid mass. Recipient lymphoid mass removal and donor replacement (intestine and mesentery) is least for iITx, followed by LITx. MvTx involves the most extensive recipient lymphoid mass removal (entire foregut, spleen, liver and intestine). The residual balance between donor vs recipient lymphoid mass is a major determinant of rejection and GvHD and, more specifically, that outcomes in ITx are largely determined by the exchange of lymphoid tissue and the resulting balance of GvH- and graft-vs-host (GvH)-reactive T cells. Therefore, the increased replacement of recipient lymphoid mass by the donor favors GvH reactivity over HvG responses in MvTx compared to iITx. The observations described herein indicate that this GvH response frequently occurs without GvHD.

Figure 2A:
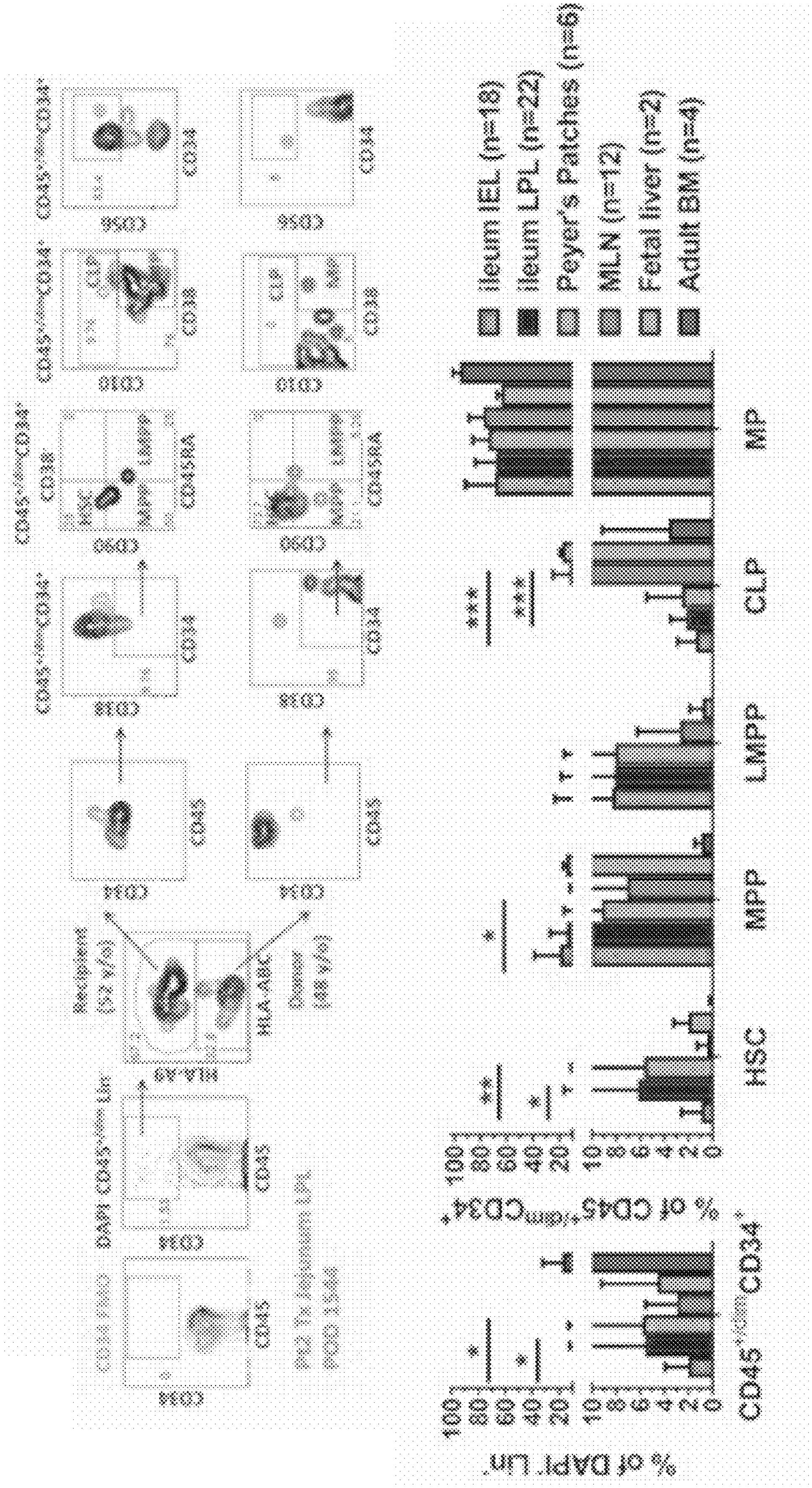
FIG. 2A illustrates gating scheme (left) for detection of hematopoietic stem cells (HSCs) and progenitors in human intestinal structures (summary in bar graph). IEL: intraepithelial lymphocytes. LPL: Lamina propria lymphocytes.

As illustrated in FIG. 1, iITx and MvTx are commonly associated with T cell and multilineage macrochimerism without GvHD, which indicates high level multilineage macrochimerism following LTx and that liver and intestinal grafts can hematopoietic stem cells or hematopoietic progenitor cells. Example of staining is shown in FIG. 1A. Chimerism in each lineage overtime is shown in FIG. 1B-E. Each symbol type represents an individual patent. Circles indicate MVTx recipients, triangles indicate isolated intestine transplantation (iITx) recipients, and squares indicate liver and intestine transplant (LITx) recipients. As shown in FIG. 2A, analysis of human intestines and associated structures for hematopoietic stem cells or hematopoietic progenitor cells showed that human intestinal mucosa as well as liver and associated lymphoid tissues do indeed contain HSCs and HPs. These mucosal cells eventually turned over and were replaced by recipient HPs and HSCs over a period of years, indicating the existence of a circulating HSC pool in humans that equilibrates with this niche.

Hematopoietic chimerism is associated with graft acceptance in a porcine model of ITx and, most importantly, has been associated with significantly improved outcomes in the clinical ITx series described herein (FIG. 3). The presence of a peak level of at least 4% donor T cells among the circulating T cells, which termed "macrochimerism", is associated with highly significant reductions in rejection rates and de novo donor-specific antibodies (DSA) development (FIG. 3D-F).

GvH reactivity (GvHR) can target recipient lymphohematopoietic cells, causing cytopenias and systemic symptoms without overt epithelial end organ GvHD (skin rash, native gut and liver dysfunction, etc). Studies in mice revealed that T cells mediating this "lymphohematopoietic GvHR (LGvHR) do not enter into the epithelial GvHD target tissues in the absence of local inflammatory stimuli induced by conditioning (e.g. irradiation) or infection. The application of local or systemic inflammatory stimuli by TLR agonists, for example, converts LGvHR into a GvHD affecting skin and intestinal tissues. LGvHR can cause severe cytopenias in animal models if donor HSCs are not given to replace the destroyed recipient HSCs and can contribute to cytopenias following ITx. Therefore, the association of T cell macrochimerism with reduced rejection reflects a similar phenomenon that LGvHR mediated by GvH-reactive cells in the allograft controls HvG rejection responses in subjects receiving ITx, resulting in reduced rejection rates, without associated GvHD.

Figure 3A:
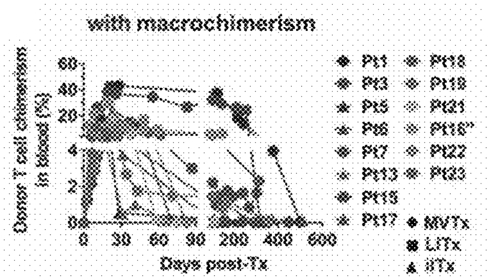
FIG. 3A-3F illustrate donor T cell macrochimerism (greater than 4%) in blood associated with significantly reduced rejection and donor-specific antibody (DSA) development, without graft-vs-host disease (GvHD).
Figure 3B:
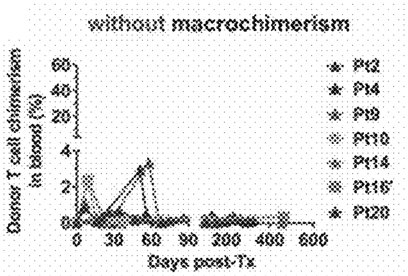
Figure 3C:
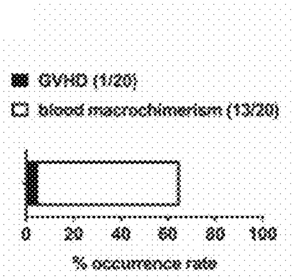
Figure 3D:
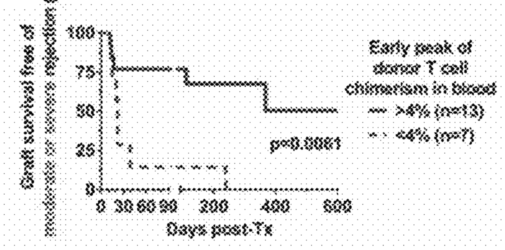
Figure 3E:
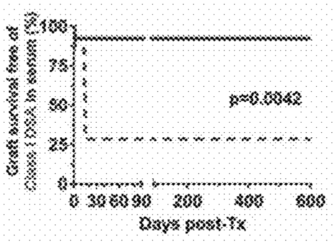
Figure 3F:
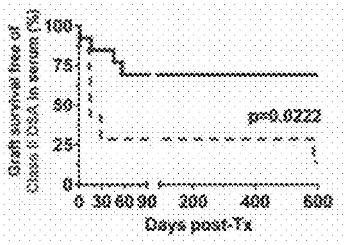
Figure 4A:
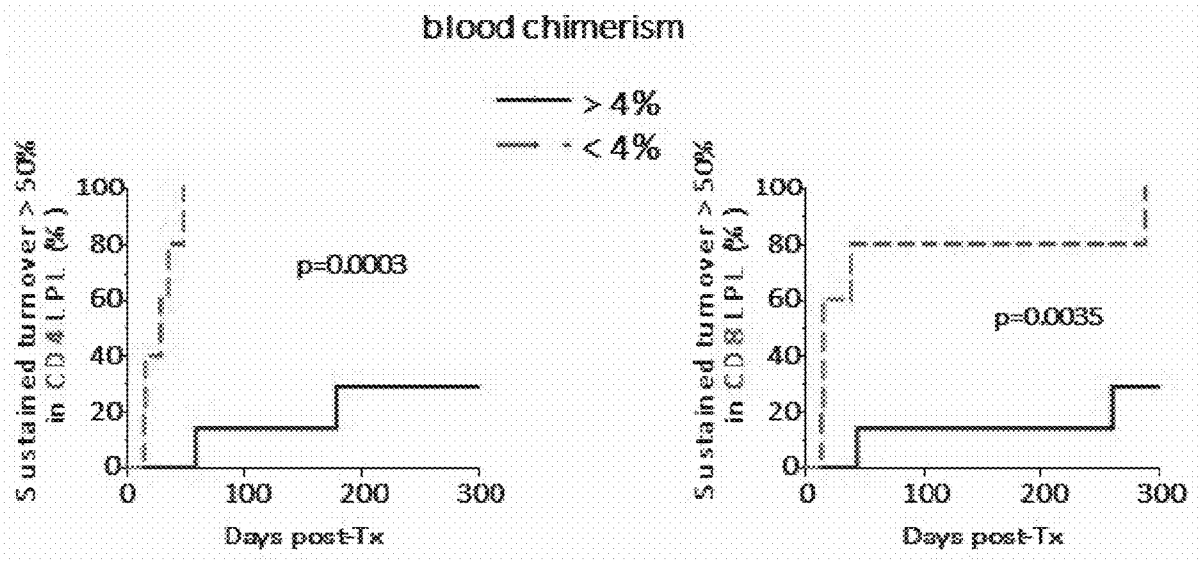
FIG. 4A illustrates inverse relationship between peripheral blood macrochimerism (defined as peak donor contribution to T cells greater than 4%) and rate of replacement of graft mucosal T cells by the recipient.
Figure 4B:
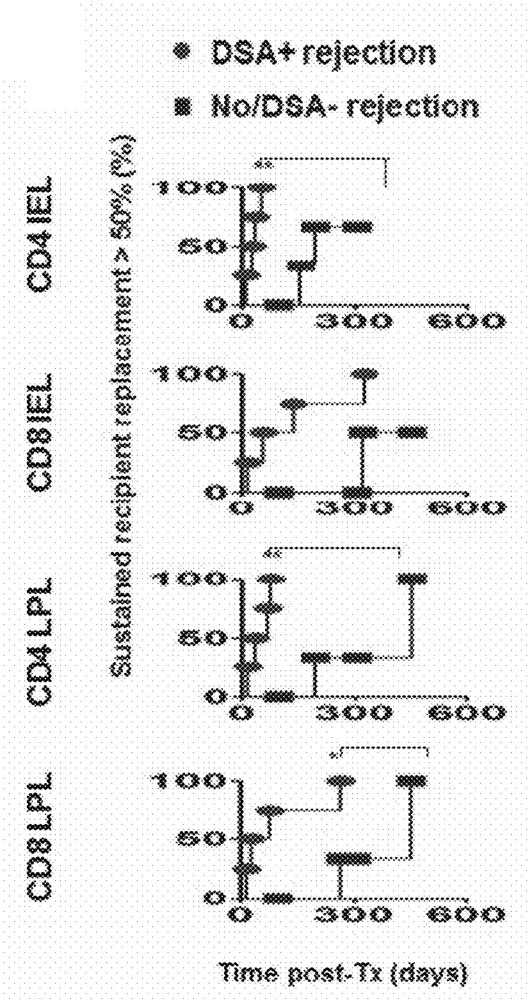
FIG. 4B illustrates more rapid rates of graft mucosal T cell replacement by the recipient in subjects who develop DSA+ rejection. Results of lamina propria (LPL) are shown but similar results were obtained for intraepithelial lymphocyte (IEL) for analyses in FIG. 4A and FIG. 4B.

The prospective analysis of T cell chimerism (and chimerism of other hematopoietic lineages) in a consecutive series of ITx recipients, combined with development and use of a novel method of identifying and tracking alloreactive T cells in transplant recipients, confirmed that LGvHR does indeed occur without GvHD in ITx recipients. By combining multiparameter flow cytometry (FCM), including allele-specific mAbs to distinguish donor and recipient-derived cells, with high-throughput TCRP chain CDR3 sequencing-based approach to track alloreactive T cells in the GvH and HvG directions in the graft and circulation evidence showing LGvHR occurring and controlling rejection was obtained. High-level multilineage donor hematopoietic chimerism is common in recipient blood after ITx, especially in recipients of MvTx, often persisted >1 year and usually is not associated with clinical GvHD (FIG. 1 and FIG. 3A-C). Clinically significant rejection episodes and de novo development of donor-specific antibodies (DSA) are significantly reduced in subjects with T-cell macrochimerism (>4%) in peripheral blood early post-transplant (FIG. 3D-F). Blood macrochimerism is also associated with slower replacement of donor graft mucosal T cells by the recipient, which also correlated with reduced DSA+ rejection46 (FIG. 4). These observations link events in the graft with those in the peripheral immune system and implicate peripheral blood chimerism in the pathway leading to improved outcomes.

Figure 5:
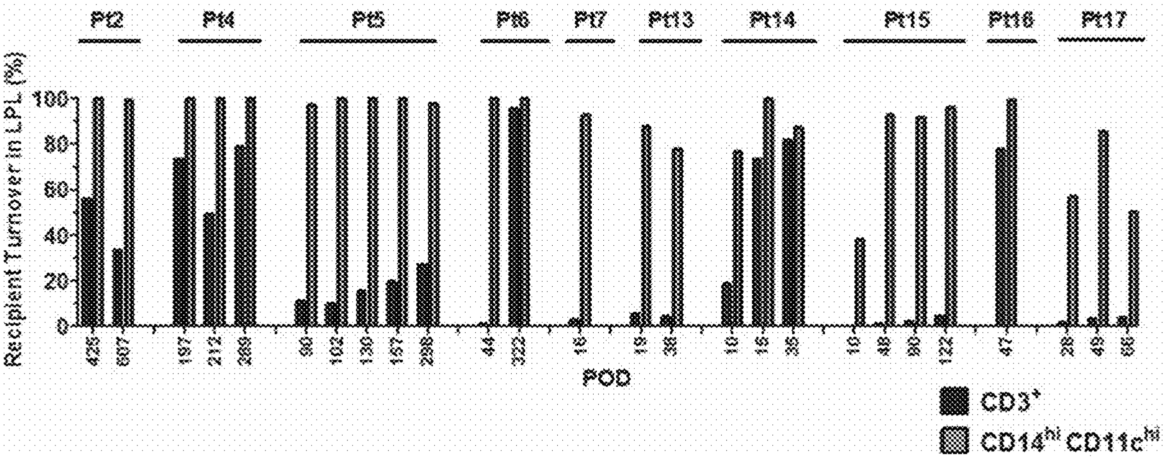
FIG. 5 illustrates rapid replacement of myeloid antigen-presenting cells (APCs) by the recipient in mucosa of intestinal allografts, regardless of rate of T cell replacement by the recipient. The $CD14^{hi}CD11c^{hi}$ bars show that the major donor myeloid APC population un the allograft is rapidly replaced by the recipient in ITx grafts, both in subjects with rapid and in those with slow replacement of donor T cells by the recipient.
Figure 6A:
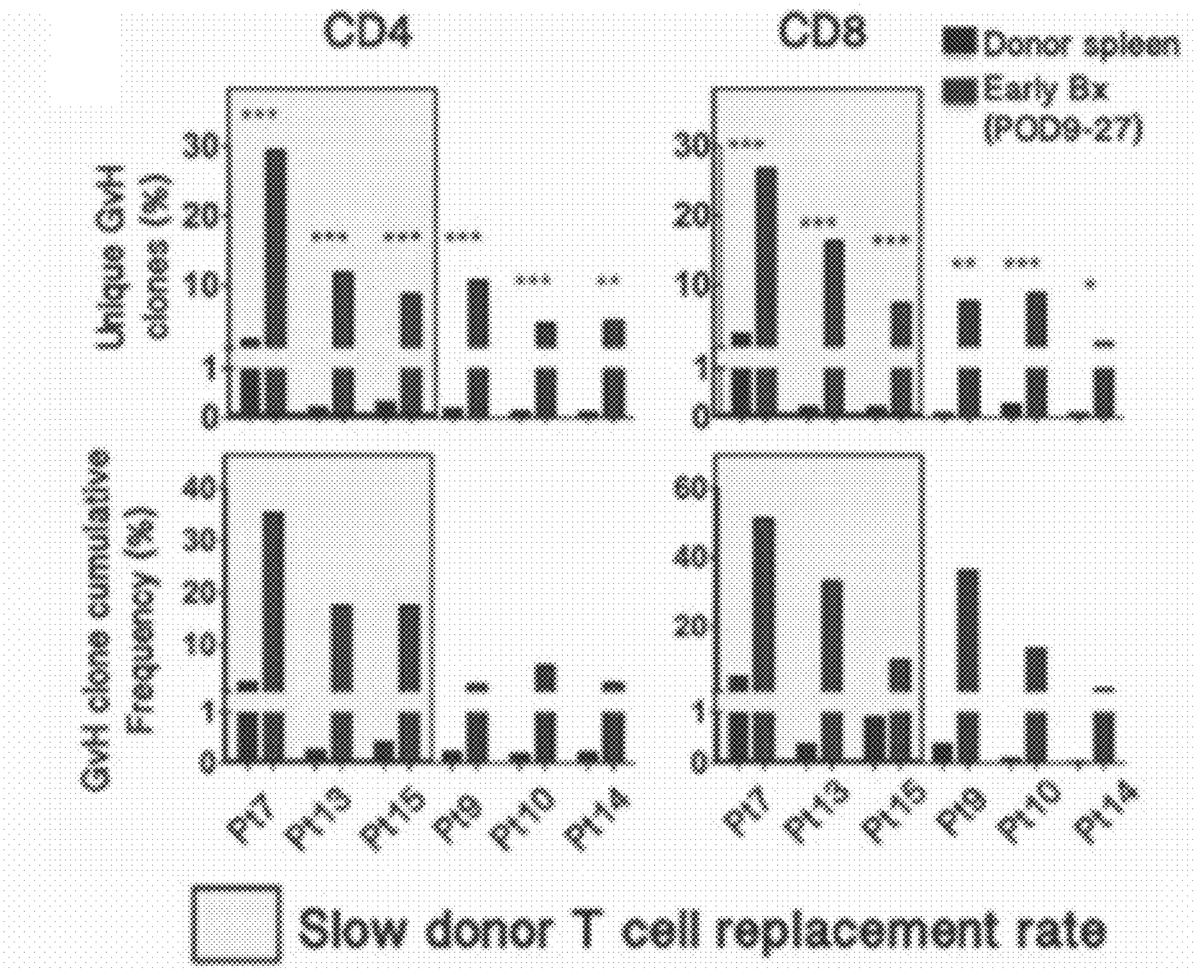
FIG. 6A illustrates high cumulative frequency of graft v. host (GvH) clones in graft early post-transplant day (POD) fewer than 50 days in subjects with slow replacement of donor T cells in the graft by the recipient. "Cumulative frequency" is the sum of the frequencies among donor T cell clones in pre-transplant spleen or among all intestinal allograft clones identifiable as donor-derived from pre-transplant sequencing. The shading indicates subject in whom graft T cells were replace very slowly (over years) by the recipient and had low rejections rates, whereas unshaded subjects had increased rejection rates and more rapid replacement of gut T cells by the recipients.
Figure 6B:
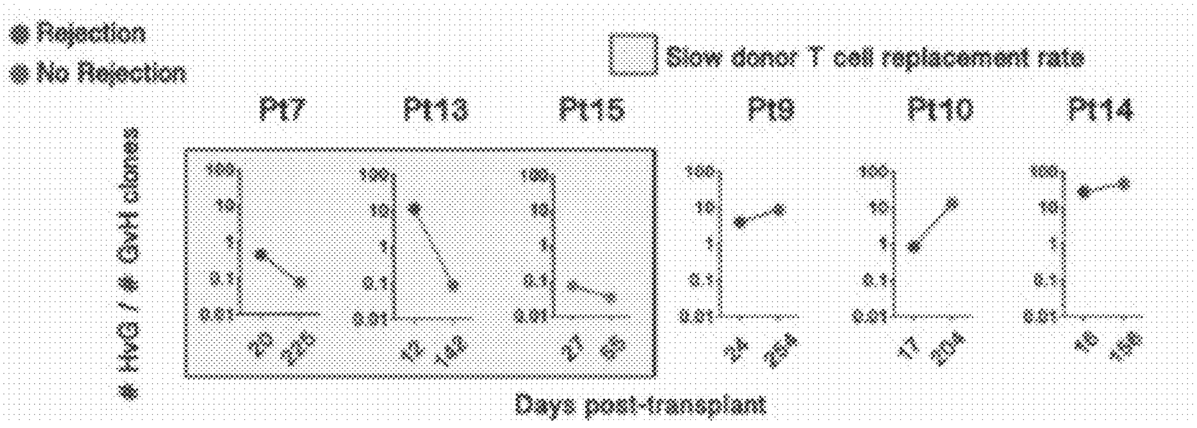
FIG. 6B illustrates correlations of slow graft T cell replacement by the recipient with long-term reductions in the ratio of host v. graft (HvG) to GvH clones in the graft following resolution of rejection.
Figure 7A:
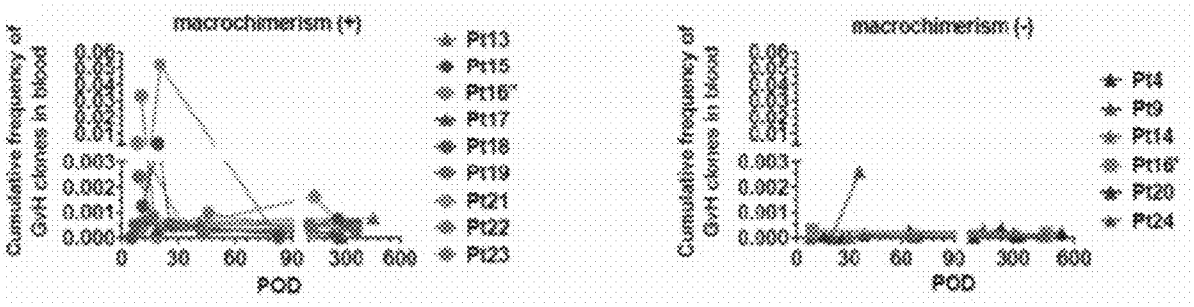
FIG. 7A illustrates kinetics of appearance in recipient circulation of donor graft-derived GvH clones detected by MLR/high throughput T cell receptor (TCR) sequencing method in the circulation. Sum frequency of GvH clones in the circulation over time is shown for subjects with macrochimerism (left) and subjects without macrochimerism (right).
Figure 7B:
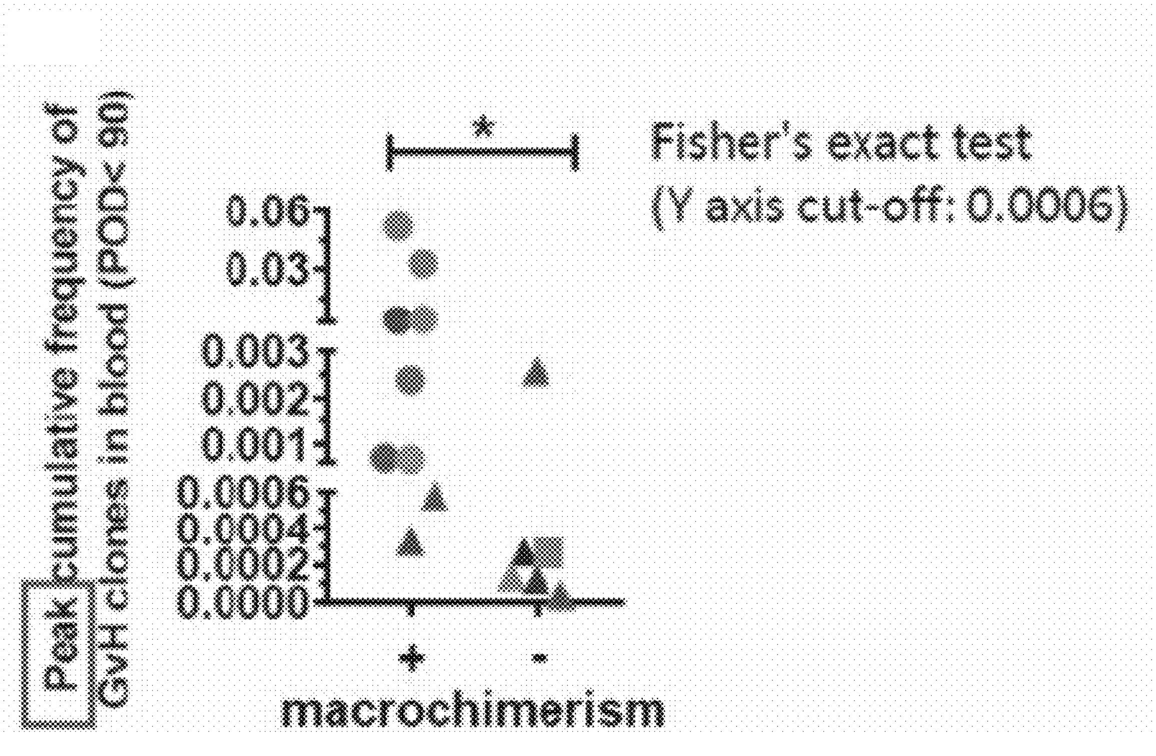
FIG. 7B illustrates significant difference in frequency of circulating GvH clones in subjects with vs those without macrochimerism. Circles represent MvTx recipients and triangles represent ilTx recipients.
Figure 9A:
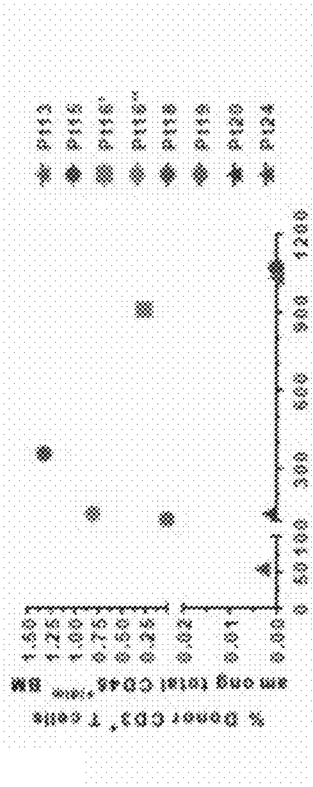
FIG. 9A-9C illustrates detection of donor CD34+ cells, T cells, and GvH-reactive T cells in recipient bone marrow following ITx.
Figure 9B:
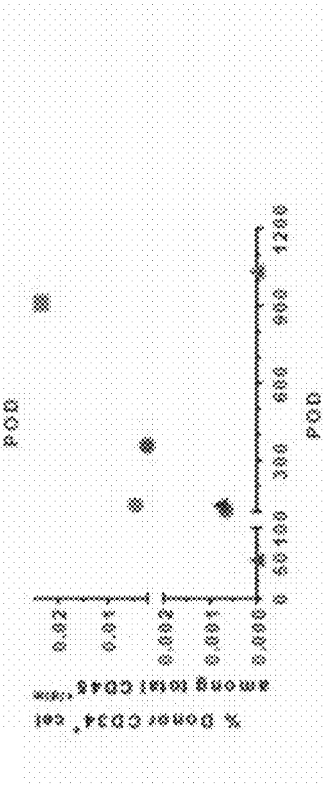
Figure 9C:
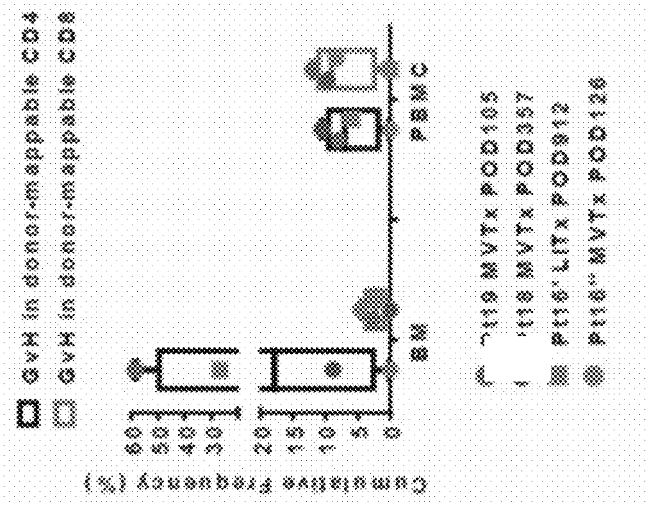

The development of LGvHR begins with local expansion of allo-cross reactive tissue resident memory (TRM) cells carried in the graft, which expand in response to the early replacement of mucosal graft antigen-presenting cells (APCs) by those of the recipient (FIG. 5), as demonstrated using alloreactive TCR tracking technique (GvH-reactive TCRs identified by sequencing of $CFSE^{low}$ pre-transplant donor T cells that increase their frequency among dividing cells in mixed lymphocyte reactions compared to their frequency in the unstimulated donor T cell population). Marked expansions of GvH-reactive TCRs in the graft in association with this early APC replacement by the recipient are detected, as shown in FIG. 6. Central to this proposal is the observation that these GvH-reactive T cells enter the recipient's peripheral circulation early post-transplant. FIG. 9 illustrates that GvH-reactive donor T cells were detected among circulating donor T cells early post-transplant. Consistent with a driving role for these GvH-reactive donor T cells in promoting chimerism, the peak levels of circulating GvH-reactive T cells in this period were significantly greater in subjects with macrochimerism than in those without (FIG. 7B).

Figure 8:
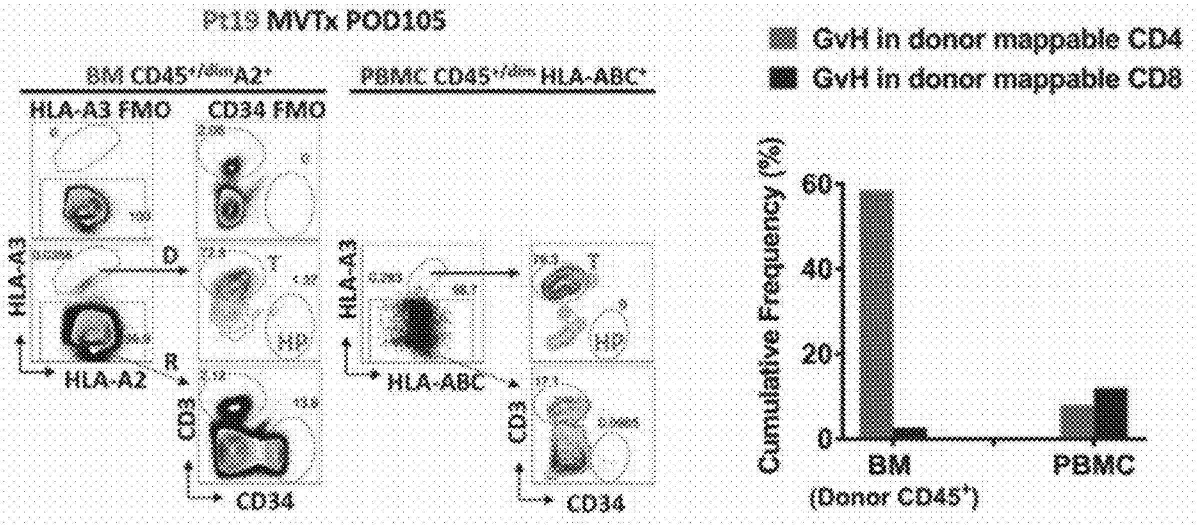
FIG. 8 illustrates FCM analysis of MvTx recipient bone marrow on day 105 post-transplant showing the presence of donor hematopoietic progenitors (HLA-A3+, CD34+) (left) and T cells in recipient marrow; and TCR sequencing of donor T cells in day 105 bone marrow reveals an accumulation of GvH clones (right).

Previous studies in murine models have shown that LGvHR can convert established mixed chimerism to full donor chimerism by attacking recipient hematopoietic cells without causing GvHD and that they can resist rejection induced by HvG-reactive T cells. As stated above, a similar phenomenon can explain the correlation between early T cell chimerism, multilineage chimerism and reduced rejection in ITx recipients. In this setting, the allograft itself can provide HSCs/HPs that contribute to the multilineage chimerism as a consequence of hematopoietic "space" created by the LGvHR. Indeed, the presence of HSCs and HPs in the normal human intestine was demonstrated (FIG. 2A). Evidence of these graft-derived HPs/HSCs contributing to the multilineage chimerism observed in these subjects was obtained as follows: long-term donor T cell chimerism in the blood was predominated by cells with a recent thymic emigrant (RTE) phenotype (FIG. 2B) that was rich in T cell receptor excision circles (TRECs) (FIG. 2C), suggesting that they developed de novo in the recipient thymus. Consistently, these T cells lacked repertoire overlapping with those of the donor prior to transplant. Furthermore, donor B cells in the recipient circulation included naïve cells (FIG. 2D) that were also likely to originate from progenitors in the allograft (FIG. 2A). Consistent with a role for LGvHR in creating "space" that permitted the engraftment of donor-derived HSCs/HPs in the recipient bone marrow, both GvH-reactive donor T cells and donor hematopoietic progenitors in bone marrow of these recipients were detected (FIG. 8 and FIG. 9). The data in human ITx recipients indicated that GvH T cells entering the circulation promoted induction of chimerism from engrafted progenitors carried in the allograft. The association with reduced allograft rejection (FIG. 2) was consistent with the notion that LGvHR promoted donor hematopoietic engraftment in the marrow by attacking recipient hematopoietic cells and possibly controlling HvG reactivity.

Figure 10A:
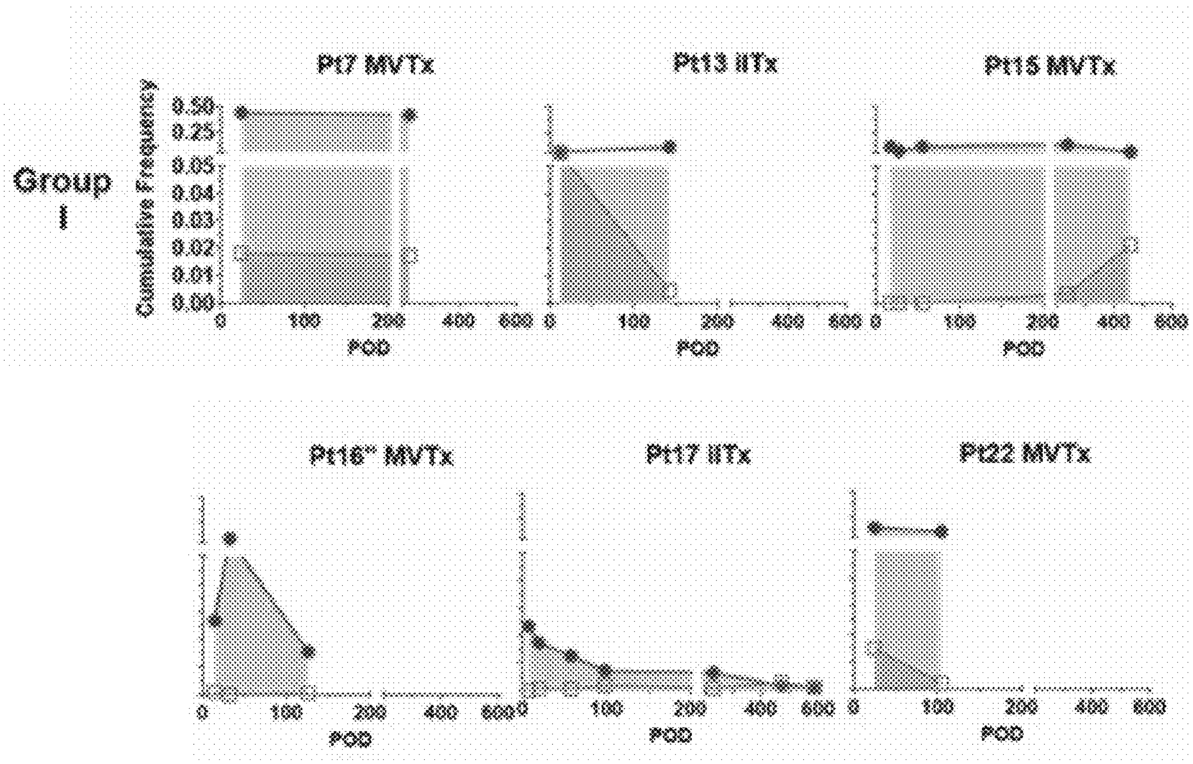
FIG. 10A-10E illustrates enrichment of GvH compared to HvG clones in graft mucosa and absence of Class I DSA circulation are associated with donor T cell macrochimerism (peak donor T cells >4%) in the blood. GvH and HvG clones were defined by sequencing $CFSE^{low}$ cells in pre-transplant MLRs.
Figure 10B:
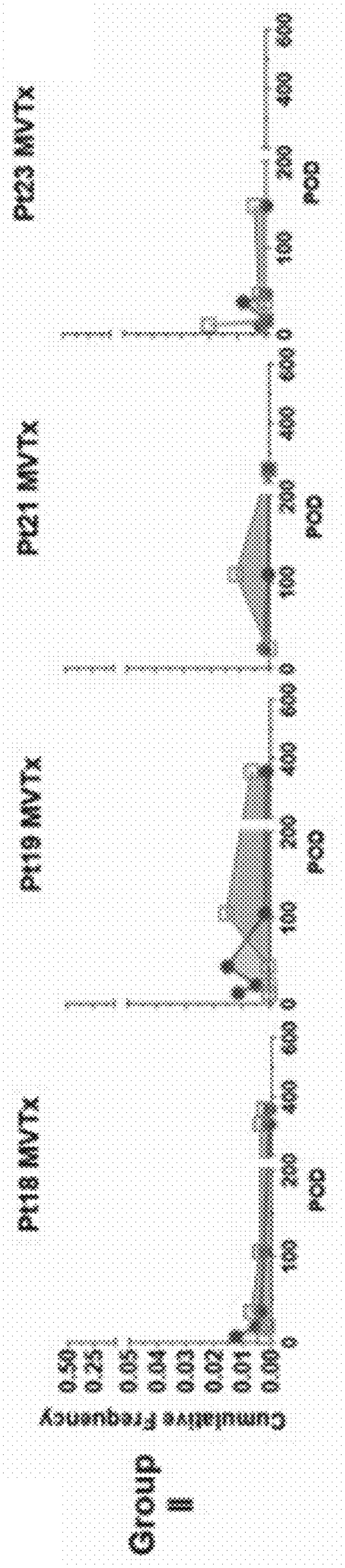
Figure 10C:
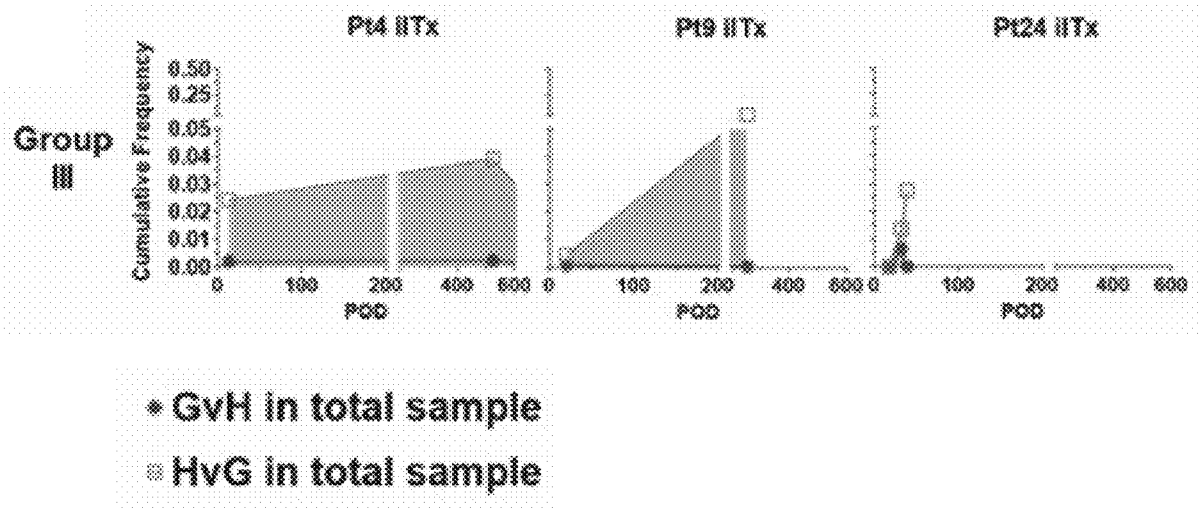
Figure 10D:
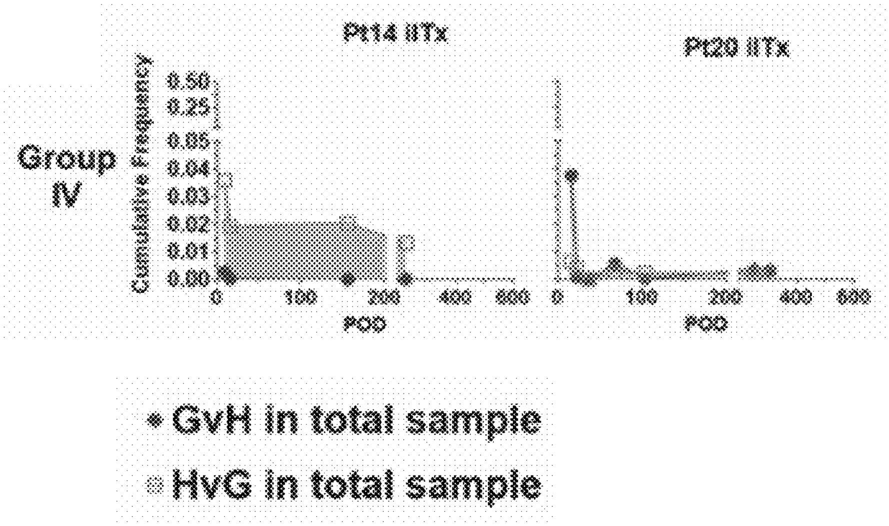
Figure 10E:
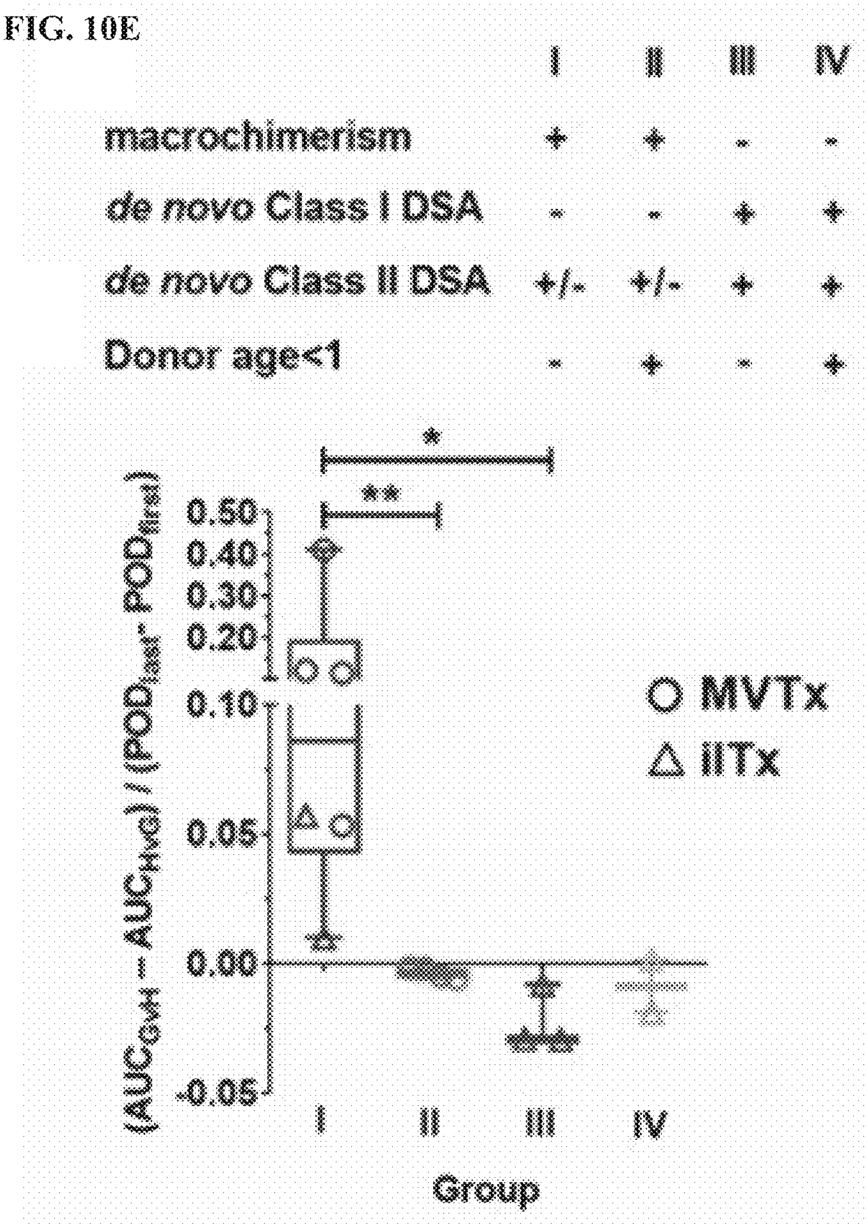
Figure 11:
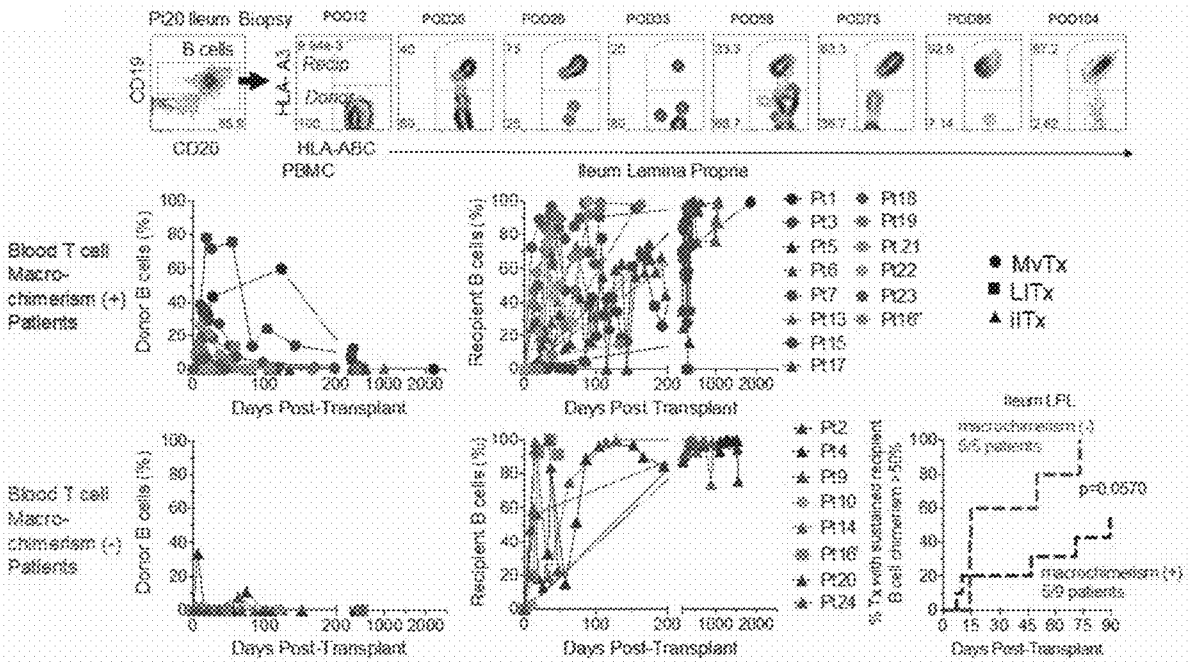
FIG. 11 illustrates B cell chimerism in peripheral blood (left) and ileum lamina propria (right) of ITx recipients with and without macrochimerism (defined as a peak of >4% donor T cells in the peripheral blood). Each symbol and line represent an individual subject. MVTx recipients are represented by circles, ilTx subjects by triangles and the single LITx recipient is represented by a square.

In the same group of subjects, a direct correlation between mixed (i.e. donor-specific antibody [DSA]+) rejection and accelerated replacement of CD4+ and CD8+ gut-resident T-cell populations by recipient T cells with a non-TRM, circulating T cell phenotype was observed, in which HvG T cell clones defined by the pre-transplant MLR/high throughput TCR sequencing approach predominated. These HvG clones persisted within the graft, acquired the TRM phenotype after the rejection resolves, and seeded the entire gut, posing a constant threat of rejection. Consistent with a role for local GvH alloreactivity in both driving peripheral blood macrochimerism early post-transplant and in controlling HvG responses locally in the graft, the ratio of GvH to HvG clones in the graft mucosa was greater in subjects with blood macrochimerism than in those without in grafts from donors >1 year old (FIG. 11, Groups I and III). Younger donors could have had an incomplete mucosal TRM compartment at the time of transplant as described. Consistently, recipient repopulation of the graft mucosa tended to be more rapid regardless of chimerism status and neither GvH nor HvG clones had shown marked expansion in the graft thus far (FIG. 10B, D, E, Groups II and IV). The same GvH-reactive TCRβ sequences within the graft mucosa and the bone marrow and the circulation at different times in individual subjects were detected, consistent with the interpretation that GvH-reactive T cells expand in the graft mucosa, where they arise as TRM that were activated by recipient APCs that rapidly enter the graft mucosa, then migrated to the peripheral circulation and ultimately to the bone marrow. These GvH-reactive clones can make space for donor HSC/HP engraftment in the bone marrow and counteract HvG reactivity locally within the graft, thereby protecting it from rejection, and within the recipient bone marrow, further helping to promote donor HSC/HP engraftment.

The significance of the observations described above is: murine study showing that GvH-reactive donor T cells in hematopoietic cell transplantation (HCT) make the graft resistant to rejection by HvG-reactive recipient lymphocytes. Likewise, results in the ITx subjects suggest that expanded GvH-reactive T cells can attenuate HvG reactivity, improving outcomes. The correlation of macrochimerism with early LGvHR in the circulating T cell pool detected by TCR sequencing, combined with evidence that donor hematopoietic stem cells or hematopoietic progenitor cells from the graft enter the recipient bone marrow and contribute to hematopoiesis, along with the detection of GvH T cells in the recipient bone marrow, suggests that LGvHR creates hematopoietic "space" in these subjects. These observations can provide a window of opportunity to achieve durable chimerism and tolerance via infusion of additional CD34+ cells from the donor without adding conditioning or risk of GvHD, as these donor hematopoietic stem cells or hematopoietic progenitor cells can engraft in the recipient marrow where the LGvHR is taking place. Therefore, a pilot clinical trial of donor-specific bone marrow (BM) CD34+ hematopoietic stem cell or hematopoietic progenitor cell infusion at a time when graft-derived LGvHR peak early after MvTx or vMvTx is proposed herein. In some instances, the durable mixed chimerism and donor-specific tolerance can be achieved with this approach. In rodent models, durable mixed chimerism has been associated with robust tolerance induction across the most challenging immunological barriers, allowing the most immunogenic grafts such as skin and intestinal allografts from the donor to be accepted permanently without immunosuppression. While transient chimerism has permitted renal allograft tolerance in monkeys and humans, long-term acceptance of more immunogenic grafts such as hearts and islets has not been achieved with transient chimerism. Therefore, success in achieving durable mixed chimerism without recipient conditioning by exploiting the LGvHR can be a watershed in the ITx field as it can permit tolerance induction, avoiding the high levels of immunosuppression administered to these subjects, and preventing the currently major problem of rejection. Subjects who achieve persistent mixed chimerism in this trial and who have been free of moderate-severe rejection events and de novo DSA development by 1 year post-transplant can undertake a program of immunosuppression minimization. While donor bone marrow infusion has been included in previous ITx recipient cohorts, these infusions were given at the time of transplantation, prior to development of LGvHR, and in some cases involved irradiation of the donor graft, which can eliminate LGvHR completely, since the GvH-reactive T cells arise from the graft itself. The approach of timing the CD34+ cell infusions to the time of maximal LGvHR is therefore novel.

The observations made in ITx recipients also have significance for the development of biomarkers that can allow personalization of immunosuppression that can reduce both high rejection rates and the consequences of overimmunosuppression. The strong correlation observed between early T cell macrochimerism and reduced rates of significant rejection and DSA development (FIG. 3) indicates that macrochimerism can serve as a biomarker for reduced rejection risk and thereby ultimately provide a basis for personalizing immunosuppressive therapy. Accordingly, Examples 2-4 aim to demonstrate infusion of donor BM CD34+ cells to MvTx (including vMvTx) recipients at the time of maximal LGvHR can increase the level and duration of donor multilineage chimerism in the blood without inducing GvHD and can permit late immunosuppression tapering, thereby reducing risks of opportunistic infections and malignancies. Additionally, the macrochimerism can continue to predict reduced rejection and de novo DSA development in both MvTx and vMvTx recipients, that donor- and recipient-specific tolerance (measured in vitro) can develop in CD34+ cell recipients and that the rate of recipient replacement of graft T cells can be a reliable predictor of subsequent rejection episodes in recipients of MvTx and vMvTx.

Example 2. Clinical Trial of Cadaveric Donor CD34+ Cell Infusion

A pilot clinical trial of cadaveric donor CD34+ cell infusion can be conducted on day 14 following MvTx, when LGvHR is maximal in most subjects (FIG. 2A), in three recipients. Prolonged peripheral blood chimerism can result from these infusions without an increase in GvHD and that subjects can develop donor-specific tolerance. Donor vertebral bodies can be harvested and processed by the methods and kits described herein. HPC Marrow can be processed and selection of CD34+ cells performed using the methods and kits described herein, which can then be cryopreserved. Three subjects can receive an infusion containing $1\times10^6$/kg CD34+ cells. Enrollment in this cohort can be staggered such that there can be a minimum of two months in between individual subject treatment with the CD34+ cell infusion to ensure safety and feasibility. No more than $10^4$ CD3+ T cells per kg recipient weight can be included in the infusion. In subjects with persistent T cell macrochimerism (>4%) and chimerism >1% in at least one other lineage at 1 year, immunosuppression can be tapered with a reduction in tacrolimus by 50% and a tapering of prednisone to eventual discontinuation. Endpoints can include ≥Grade II GvHD, rejection episodes, de novo DSA development and graft loss.

Summary of Procedures

MvTx is an en bloc transplant of the stomach, pancreas, liver and small intestine, with or without the large intestine. The recipient stomach, pancreas, spleen, liver and small intestine are removed. vMvTx is an en bloc transplant of liver, pancreas and small intestine, with or without the large intestine. The recipient liver and small intestine are removed. Induction treatment of rabbit anti-thymocyte globulin (thymoglobulin) is given at a dose of 1.5 mg/kg IV daily on days 0, 1, 2 and 3. Additional doses can be given to reduce circulating CD4+ T cell concentrations below 50/ul up to a maximum total dose of 9 mg/kg. Corticosteroids are given intravenously or orally from day 0-6 on a sliding scale, continued for 6-12 months and tapered if there is no evidence for rejection. Tacrolimus is begun intravenously or orally on day +1 and maintained at trough levels of 10-15 ng/ml for the first month and gradually reduced on an individualized basis to long-term maintenance levels of 3-7 ng/ml unless tapered as described below. mTOR inhibitors can be added in order to reduce tacrolimus usage in subjects with renal insufficiency. In recipients of donor CD34+ cell infusions who demonstrate persistent T cell macrochimerism (>4%) and chimerism >1% in at least one other lineage at 1 year, immunosuppression can be tapered with a reduction in tacrolimus by 50% and a tapering of prednisone to eventual discontinuation.

Donor vertebral bodies can be harvested and processed by organ recovery team using the methods kits such as Miltenyi CliniMacs system described herein for processing HPC Marrow and selecting for CD34+ cells. Cryopreserved CD34+ cells can be thawed at the bedside and infused immediately through an indwelling central venous line. Subjects can be premedicated with Diphenhydramine 1 mg/kg IV (maximum 50 mg) or other antihistamine for subjects unable to tolerate diphenhydramine.

Immunosuppression Minimization

All subjects can use the same immunosuppressive regimen. In subjects with persistent T cell macrochimerism (>4%) and chimerism >1% in at least one other lineage at 1 year who have been free of moderate-severe rejection events by 1 year post-transplant, tacrolimus can be tapered by 25% at 1 year, and a second decrease of another 25% can occur 30+/−15 days later if the subject does not have complications. Prednisone can be tapered to eventual discontinuation. During immunosuppression minimization and 3 months after the last reduction, subjects can undergo surveillance ileoscopy with biopsies every 2 weeks and assessment for de novo DSA development every 4 weeks. Standard of care endoscopic surveillance of rejection (every 3 months) and DSA development (every 6 months) can resume thereafter. Subjects can undergo for cause biopsies to evaluate any relevant clinical changes. Immunosuppression minimization can be halted if there is biopsy-proven mild, moderate or severe rejection or de novo DSA. While there is no control group in this pilot study, outcomes in the study group can be compared to those in historical controls and concurrent MvTx and vMvTx subjects who opt not to receive donor CD34+ cell infusion or whose donor family declines consent for research use of donor BM. Surveillance biopsies are part of the routine monitoring of ITx recipients.

Endoscopic Biopsies

One to five random biopsy specimens are taken with cold forceps 5 cm proximal to the stoma per session for surveillance. Ileoscopies occur on POD3-5 and twice weekly for the first month, weekly from 1-3 months post-transplant, biweekly from 3-6 months and monthly from 6-12 months or until ileostomy closure, whichever comes first and annually thereafter. Colonoscopy is performed annually after ileostomy closure or for indications of allograft dysfunction with negative or equivocal ileoscopy findings. Symptom-based biopsies (increased ileostomy output or feeding intolerance, gastrointestinal bleeding, change in color or appearance of the stoma) can be performed for suspicion of allograft dysfunction. Biopsies are collected in 10% buffered formalin (paraffin embedding, H&E staining). Histology and immunostaining are performed for C4d, viral panel (CMV, Adenovirus, and EBV). If there is a clinical concern for antibody-mediated rejection (AMR) a separate biopsy can be fixed in Zeus fixative and analyzed by immunofluorescence for C4d staining.

Endpoints

The primary safety/feasibility endpoint is absence of ≥Grade II GvHD. Clinically significant GvHD has essentially been absent from the cohort receiving the regimen so far, with only one case of isolated, self-limited skin GvHD in an iITx recipient, despite the development of macrochimerism (circulating T cells with peak >4% donor-derived) in 13 out of 20 recipients. None of the 11 MvTx recipients in this group developed GvHD, despite the presence of macrochimerism in most of them. Secondary feasibility endpoints are graft survival and retention at 1 month, 1 year and 3 years. The secondary efficacy endpoints are persistent T-cell macrochimerism (>4%) and chimerism >1% in at least one other lineage at 1 year post-transplant, absence of de novo DSA at 1 year post-transplant, and absence of rejection or de novo DSA after immunosuppression tapering.

Subject Monitoring for Chimerism

Multilineage chimerism can be monitored using the multicolor FCM method at regular intervals, including 7, 11, 14, 21, 28, 42, 50, and 60 days post-transplant, then every two months until 1 year post-transplant and every 3 months until 4 years post-transplant. Chimerism can also be monitored using standard CLIA-certified VNTR/STR microsatellite methods on sorted CD3+ T cells, B cells, and myeloid cells to validate the FCM results. The previous studies have shown excellent concordance of FCM and microsatellite methods of chimerism determination, though the FCM method is more quantitatively precise and can be used for the decision points described. As shown in FIG. 1, the peripheral blood chimerism in all of these 3 lineages (T cells, B cells, myeloid cells), as detected by FCM, typically declined below the levels sought by 50 days post-transplant. While a few MvTx recipients had shown chimerism in one or two lineages that exceeded these levels at 50 days, none had exceeded these levels in all 3 lineages. Thus, chimerism at these levels can suggest an effect of the infused CD34+ cells. Likewise, T cell macrochimerism can be observed at >4% persisting at 1 year post-transplant in MvTx recipients but this was not associated with chimerism >1% in any other lineage in any MvTx subjects so far (FIG. 1).

De novo DSA development can also be monitored. De novo DSA development has recently been recognized as a major risk factor for acute and chronic intestinal allograft rejection and reduced DSA development rates are associated with liver co-transplantation. Single antigen bead (SAB) assays permit improved sensitivity and specificity of HLA antibody detection. However, the SAB assay has several limitations, including binding interference (prozone), as well as the semi-quantitative nature of the mean fluorescent intensity (MFI) readout. Recently, the ability to fix complement and IgG subtypes has been recognized as clinically important markers predicting renal allograft loss and is associated with high antibody titers (>1:16) and characteristic graft histopathological findings, including local inflammation with monocyte and NK cell infiltration, contributing through cytokine release and ADCC to allograft pathology. Complement binding activity depends on the antibody IgG subclass composition, based on complement-fixing (IgG1 and/or IgG3) and non-complement-fixing IgGs (IgG2 and IgG4) isotypes. The inclusion of immunodominant DSA (iDSA) characteristics such as IgG3 and Clq binding better can predict clinical and sub-clinical AMR in a large cohort of renal transplant recipients. On this basis, the DSA analyses can include phenotype (complement fixation and subclass analysis) rather than strength alone (MFI). These analyses can be predictive of and correlate with clinical events and can provide new insight into the role of DSA in intestinal allograft rejection, since little is known about its impact on graft histology/pathology. SAB testing can be performed on all enrolled MvTx/vMvTx subjects in the BM protocol (n=9) and in contemporaneous non-bone marrow transplantation (BMT) MvTx/vMvTx subjects not enrolled in the CD34+ cell infusion trial over the 4 year study period (total expected n>9). Pre-transplant can be tested for baseline, then 1, 3, 6 and 12 months post-transplant. Positive samples for IgG DSA can be further evaluated for Clq binding and IgG subtypes. In some cases, the subjects with macrochimerism in peripheral blood cannot make de novo DSA and if DSA is present, its characteristics can be non-complement binding (largely IgG4). In some other cases, subjects who develop de novo DSA cannot have macrochimerism. Detection of complement-binding DSA in this group can better predict rejection and allograft loss than DSA MFI. Furthermore, the IgG3 subclass DSA status can increase the risk for the graft dysfunction and allograft injury phenotype characterized by intense microvascular inflammation and increased complement deposition in the graft, as found in other solid organ transplant studies. These observations can provide new insight into the possible role of antibody-mediated complement fixation in intestinal allograft rejection.

Methods

The presence of IgG DSA can be assessed using the SAB assay according to the manufacturer's protocol. DSA >1000 MFI (mean fluorescence intensity) in Luminex® single beads assay in any sample defines a subject as DSA positive. The specificity of class I and class II HLA-specific DSA and the strength (MFI) can also be determined. The presence of C1q-fixing DSA can be assessed using SAB array assay according to the manufacturer's protocol (C1q screen™, One Lambda Thermo Fisher, Inc). To determine IgG subclass, the phycoerythrin-conjugated anti-pan IgG reporter antibody in the SAB assay can be replaced with monoclonal antibodies specific for IgG1-4 subclasses (IgG1 clone HP6001, IgG2 clone 31-7-4, IgG3 clone HP6050, IgG4 clone HP 6025, Southern Biotech).

Inclusion Criteria

Adult and pediatric multivisceral transplant recipients and liver/intestine/pancreas transplant recipients can include those who received prior intestinal/multivisceral transplant. Indications for MvTx/vMvTx include: intestinal failure due to short bowel, malabsorption and dysmotility in subjects whose liver disease has progressed to end stage; re-transplant candidates who lost the first graft to rejection or subjects who have higher risk of toxicity from chronic long-term immunosuppression (i.e., subjects with chronic kidney disease); and other indications include slow-growing low malignant potential tumors infiltrating the mesenteric root, complete portomesenteric thrombosis and abdominal catastrophes after major abdominal trauma or surgical complications with frozen abdomen.

Planned follow-up at the study site for at least 48 months from the transplant. Subjects or legal adult representative parental/legal guardian capable of providing signing the informed consent document themselves(in general, assent can be sought for children aged 12 years or older). While this pilot study cannot have a case-control design, the same studies on contemporaneous MvTx and vMvTx recipients who decline to enroll in the study or whose deceased donor families decline to consent to bone marrow use for this research protocol can be enrolled and performed.

Exclusion Criteria

Subjects with known immunodeficiency syndrome, systemic active sepsis, multiorgan failure with hemodynamic instability, severe cerebral edema with radiologic findings of effaced sulci and/or herniation, poorly controlled hypertension (systolic blood pressure >170 on at least 2 occasions), diabetes mellitus (HbA1c>8) or uncontrollable seizure disorders can be excluded from the trial. Subjects with psychosocial history of non-adherence to medical regimens, substance addiction in the last six months, psychosocial instability and lack of reliable social support system, or significant active psychiatric disorder that prevents cooperation or adherence to medical therapy can be excluded from the trial. Subjects with pre-existing PRA MFI titers >5000 by Luminex can be excluded from the trial. Subjects who are pregnant or breast-feeding or intend to get pregnant during the study period can be excluded from the trial. Subjects cannot receive CD34+infusion if they have active severe infections, hemodynamic instability, moderate to severe rejection or clinical presentation consistent with GvHD, or have a history of previous hematopoietic progenitor cell (HPC) infusion or transplant of any kind can be excluded from the trial. Subjects with severe cardiovascular and/or respiratory instability, as defined by requirement of vasopressor support can be excluded from the trial. Female subjects of childbearing age and male subjects who are not using and/or are unwilling to use an effective method of birth control for the duration of the study can be excluded from the trial.

Recruitment, Subjects and Controls

Adult and pediatric subjects (age ≥182 years old and <65 years old) who are currently listed in UNOS for multivisceral (MVTx) transplant, including those who received a prior ITx or MVTx can be eligible for participation in this open label, pilot trial. Of those, 50% are MVTx. Conservatively estimating yearly volume to be 3 cases per year, 2 MVTx case/year can be available for enrollment in this pilot trial proposal. For this proposal, there are two types of subjects who can be enrolled in the control arm of the study: first, those that opt to only enroll in the control arm for Example 2 (i.e., subjects who do not wish to receive the investigational, CD34+ infusion) and, second, MVTx recipients for whom CD34+ cells from the organ donor are not successfully obtained and are thus not available for investigational treatment. From the aforementioned estimates, those subjects who consent to the control arm are expected to be 2/year.

The subjects can be contacted by the study coordinator for prescreening after registration on the UNOS waiting list. The study coordinator and treating physician can obtain informed consent. Transplant recipients who opt not to receive CD34+ cell infusion or whose donor family declines consent for research use of donor BM can be enrolled as concurrent controls. All subjects can receive the same treatment according to the protocol, scheduled monitoring and the same sample procurement and mechanistic studies can be performed.

Potential Pitfalls/Alternatives

While highly unlikely, it is possible that significant (Grade II or greater) GvHD can develop with the CD34+ cell infusion dose. Since GvHD is a known complication of ITx, if ≥Grade II or greater GvHD develops in two of the three subjects in the treatment cohort or if a Grade III or greater GvHD develops in one of the three subjects in the treatment cohort, further enrollment for CD34+infusion can be terminated. It is also possible that the CD34+ cell infusion cannot result in chimerism at levels that meet the criteria for immunosuppression (ISP) minimization. However, the concurrent analyses of tolerance in these and other (non-CD34+ recipient) subjects (Example 4) can allow determining whether or not CD34+infusion can lead to tolerance even without persistent chimerism.

Example 3. Determine the Relationship Between Graft, Bone Marrow and Blood Chimerism and Protection from Rejection Following MvTx or vMvTx In this example, multilineage blood chimerism levels, phenotypes and duration; rates and phenotypes of recipient graft T and B cell chimerism; and donor chimerism in recipient bone marrow in the MvTx or vMvTx recipients receiving CD34+ hematopoietic stem cell or hematopoietic progenitor cell infusions in Example 2 and in concurrent and historical MvTx or vMvTx recipients not receiving bone marrow transplantation (BMT) can be monitored. It can be determined whether or not the infusion of donor CD34+ cells at the time of maximal LGvHR leads to increased and/or prolonged multilineage donor chimerism in the recipient's blood and bone marrow and, in the absence of rejection, is associated with increased long-term persistence of donor lymphocytes in the allograft mucosa. These results can be correlated with clinical outcomes.

Serial blood specimens on all subjects for chimerism can be followed. Multilineage chimerism can be measured by FCM using HLA allele group-specific mAbs that distinguish donor and recipient HLA alleles to identify donor and recipient T cells, B cells, granulocytes and monocytes. Pre-transplant subject blood and donor blood, splenocytes or lymph node cells from specimens at the time of transplant can be screened with candidate class I HLA group-specific mAbs (1 Lambda; mAbs selected on the basis of donor and recipient HLA typing) to identify mAbs that best distinguish the donor from the recipient. Subject leukocytes collected on days 7, 14, 21, 28, 42, etc as described in Example 2 can be tested for lineage chimerism by multicolor FCM. Pan-class I mAb can be counterstained to increase confidence in data from HLA allele-selective mAbs, as described. T cell chimerism can be assessed with high sensitivity, well below 1% (in the 0.1% range), as T cells have relatively uniform levels of class I expression. Phenotypic markers to distinguish naïve and memory T and B cell subsets are routinely used in the 18-color panel on the Aurora spectral flow cytometer, allowing distinction of recent thymic emigrants and other T cell subsets from memory cells as well as de novo B lymphopoiesis. Infusion of donor CD34+ cells can result in greater levels of long-term T cell and non-T cell chimerism in the circulation than in control MvTx recipients, that donor cells can be enriched for RTEs and naïve B cells and that duration of chimerism can be prolonged.

Statistical Considerations

Null hypothesis that the subjects who achieve chimerism among those receiving CD34+ hematopoietic stem cells or hematopoietic progenitor cells can be tested to have the same average area under the curve (AUC) for chimerism over follow-up as those who receive a MvTx or vMvTx without CD34+ cell infusion. The logarithms of AUC between the BM recipients and non-recipients can be compared using a linear model with adjustment to transplant stratum (MvTx vs vMvTx). While the study described herein is not designed to compare transplant type, this analysis can allow assessing the treatment effect while accounting for potential heterogeneity due to transplant type.

On serial mucosal biopsy specimens, the replacement of donor T, B, and myeloid cell populations can be examined by the recipient and its relationship to peripheral blood chimerism, rejection and DSA development described above (FIG. 4). Since a significant inverse correlation between the presence of macrochimerism was observed in the peripheral blood and the rate of replacement of donor T cells by the recipient in the graft (FIG. 4A), the higher levels of peripheral blood chimerism can be expected with infusion of donor BM CD34+ cells in the trial described herein can be associated with slow replacement of donor T cells by the recipient in the intraepithelial lymphocyte (IEL) and lamina propria (LPL) compartments of the mucosa. Since the data in subjects without rejection show that replacement of donor mucosal T cells by the recipient is a very slow process46, the "physiological" turnover of these cells populations under homeostatic conditions can be very slow. Since such turnover eventually takes place, the donor T cells can contribute more to longer-term de novo mucosal T cell populations in the CD34+ cell recipients than in controls, resulting in consistently slower replacement of donor mucosal T cell populations by the recipient in CD34+ cell recipients.

Phenotypic analyses on CD4+ and CD8+ IELs and LPLs using multicolor FCM can be carried out to assess whether or not the recipient T cells in the graft mucosa have a phenotype more consistent with that of circulating cells (CD69−, CD28+, CD103−), as the presence or absence of rejection or if they acquire the TRM phenotype (CD69+, CD28−, and low CD103+, especially for CD8+ IELs).

Figure 12:
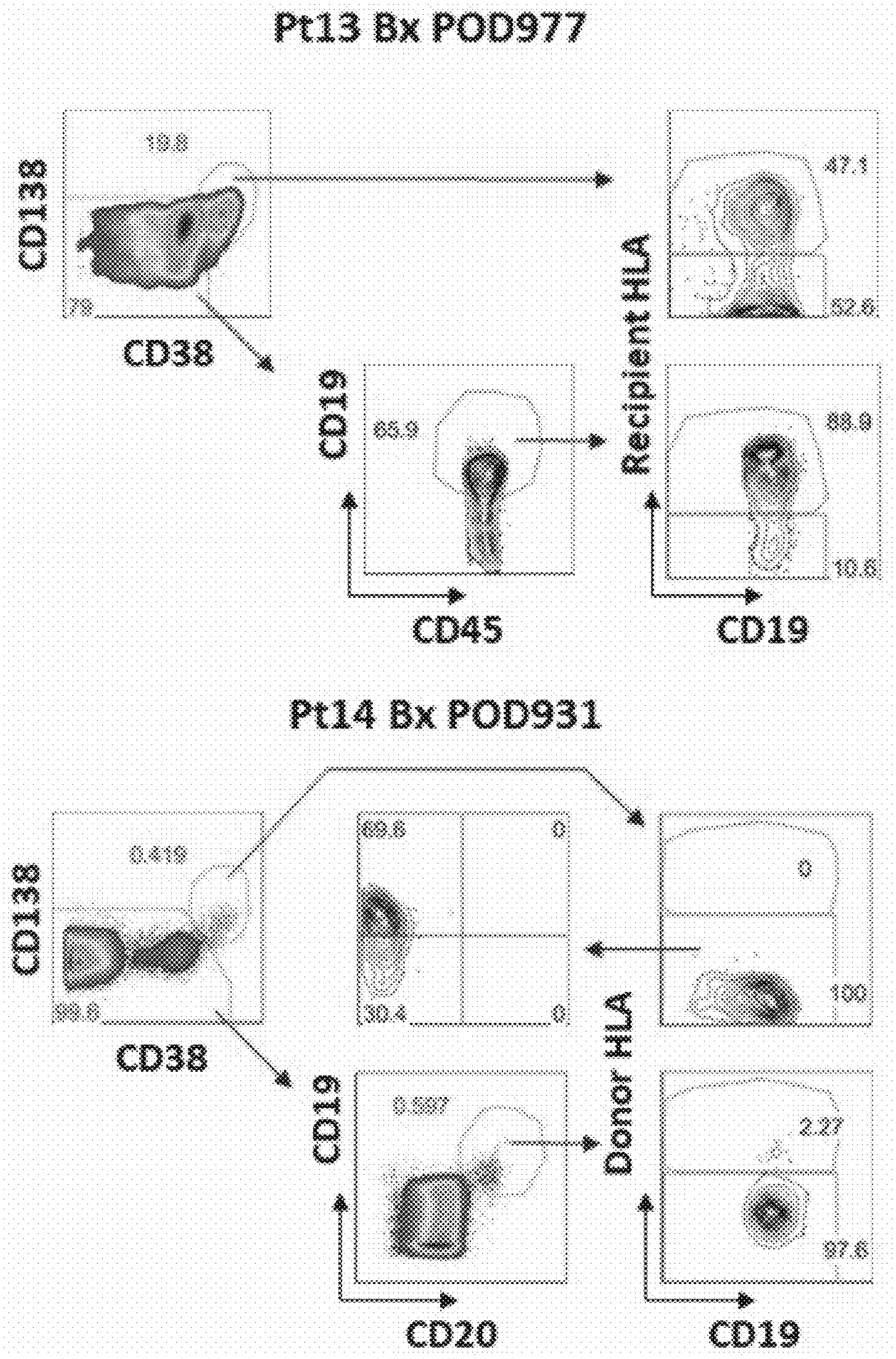
FIG. 12 illustrates donor and recipient origin of plasma cells in intestinal allografts. The same 2 biopsies presented in FIG. 9A-9C are presented here, showing the presence of plasma cells of donor and recipient B origin in subject 13 at day 977 post-transplant (top panels), whereas (bottom panels) plasma cells are all of recipient origin at day 931 in the biopsy that showed almost full recipient B cell replacement within the graft.
Figure 13:
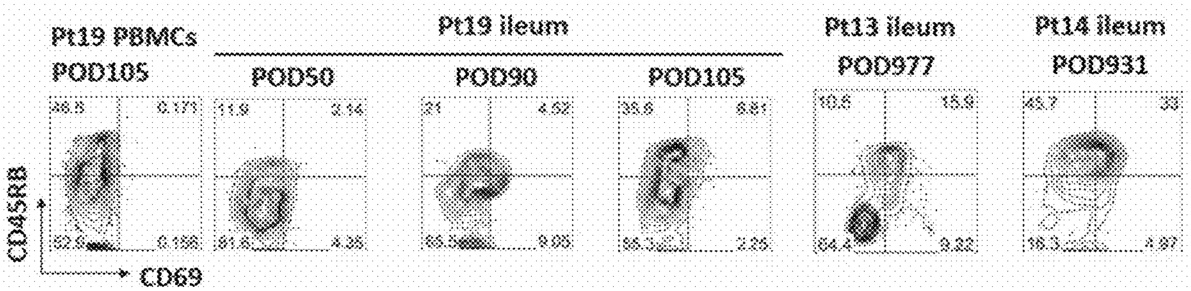
FIG. 13 illustrates evolution of recipient B resident memory (BRM) CD45RB+CD69+ phenotype among gated recipient HLA+ CD19+ CD20+ B cells in intestinal biopsy specimens over time.

Studies in progress in recipients with and without rejection suggest that graft B cell replacement by the recipient can also be more rapid in subjects lacking blood macrochimerism (and, by extension, with rejection) than in those with macrochimerism (FIG. 11), though the small group of subjects studied so far has not yet shown a statistically significant difference. The infusion of donor BM can be associated with relatively slow replacement of donor B cells in the graft by the recipient. Phenotypic analyses of donor and recipient B cells so far suggest that recipient B cells within the graft mucosa undergo class switching and even plasma cell or plasmablast differentiation (FIG. 12) in the presence of rejection and/or de novo DSA development. Such infusion of donor CD34+ cells can be associated with a lack of such differentiation among recipient B cells populating the graft. They can instead acquire the "B resident memory" phenotype which have observed among recipient B cells that populate donor graft mucosa over time (FIG. 13). If, as expected, donor CD34+ cell recipients are free of rejection, these studies can provide an opportunity to observe the "physiological" turnover and acquisition of the tissue resident phenotype of B cell populations within the graft mucosa. Since myeloid cell turnover in the graft has thus far been uniformly quite rapid in subjects with and without rejection episodes, observation of an impact of donor BM infusion on this readout is not expected Donor CD34+ cell infusion can lead to increased hematopoietic stem cell or hematopoietic progenitor cell chimerism in the recipient bone marrow compared to MVTx and vMvTx recipients and prospective MVTx and vMvTx recipients not receiving donor CD34+ cells. As shown in FIG. 9, all MvTx and vMvTx recipients analyzed at times ranging from about 125 to 900 days post-transplant had shown the presence of donor CD34+ cells in the recipient bone marrow. Two iITx recipients who were analyzed at about 125 and 1025 days post-transplant did not have detectable donor T cells or CD34+ cells in the bone marrow. These results can be compared to those in the proposed CD34+ cell infusion trial. The levels of bone marrow chimerism can be substantially higher in the CD34+ cell recipients than in non-infused MvTx/vMvTx controls. In addition, this study can also address the if GvH-reactive donor effector T cells (Teff) from the graft enter the circulation and migrate to recipient BM, where they make "space" for engraftment of hematopoietic progenitors from the graft and either maintain effector function or become bone marrow TRM.

Figure 14:
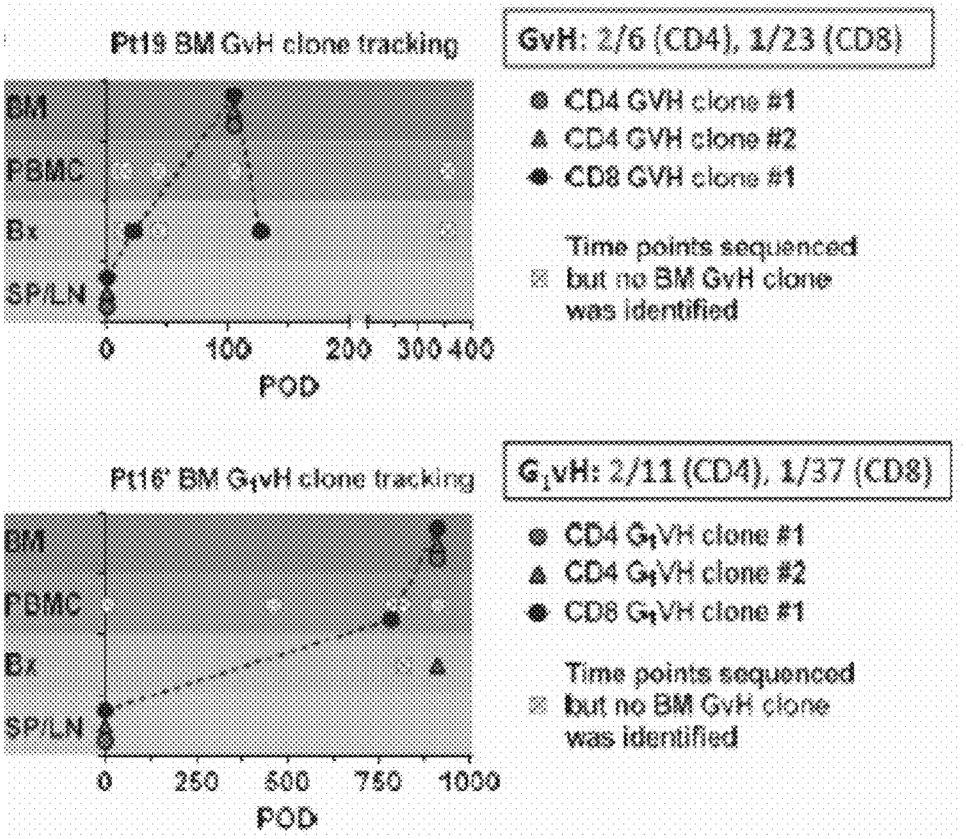
FIG. 14 illustrates tracking of individual TCR sequences detected among donor T cells in subject bone marrow (BM). For two different subjects who had BM aspirates analyzed at the indicated time point, the presence of 3 GvH clones identified among donor T cells in those bone marrow specimens is tracked over time and space. The clones were detected in intestinal allograft biopsy specimens and PBMC at the indicated timepoints and in the pretransplant GvH MLR performed with donor lymphoid tissues as the source of responder T cells.
Figure 15A:
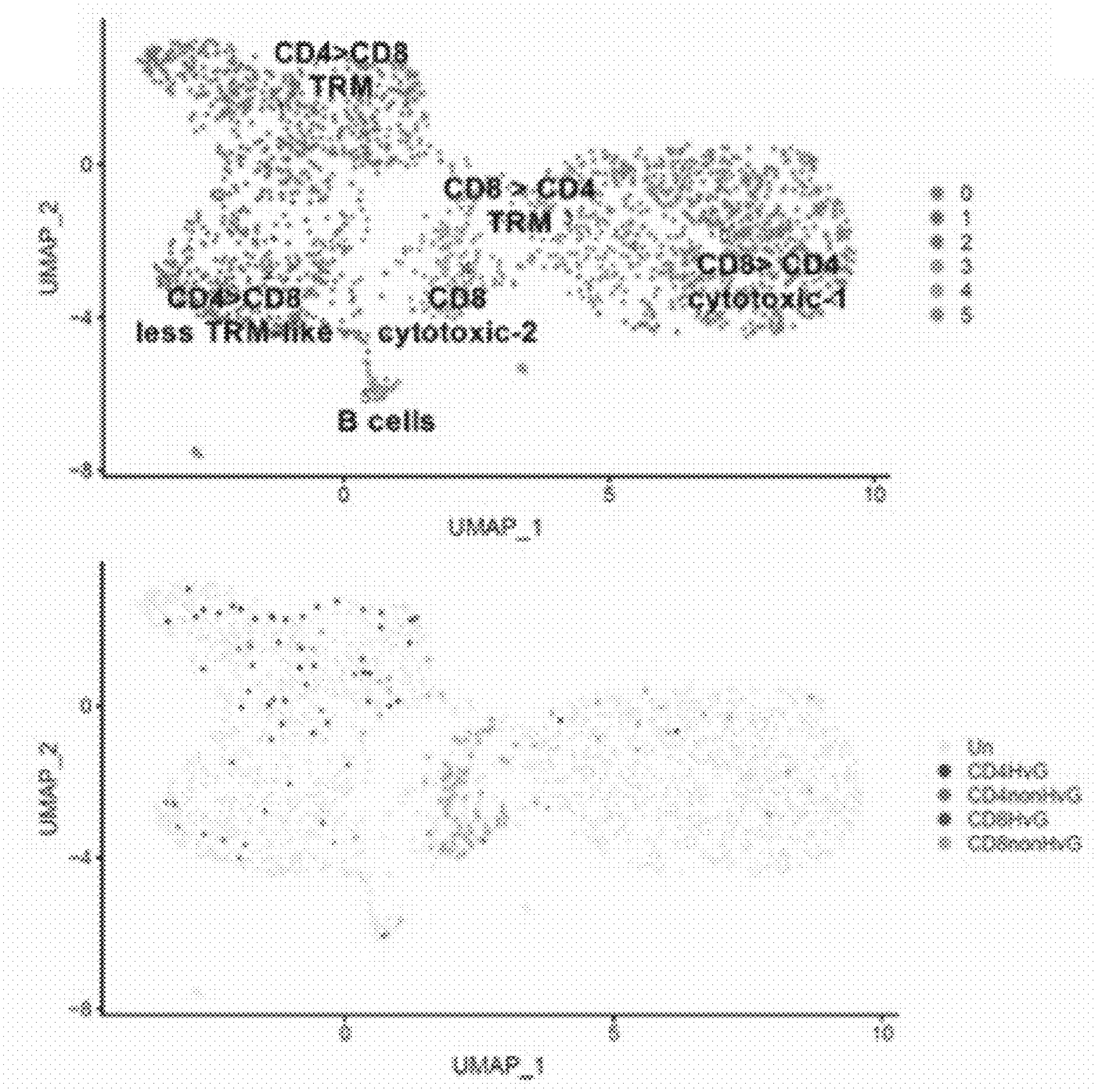
FIG. 15A-15D illustrates single cell immune profiling of recipient intestinal T cells from a long-term quiescent ileal biopsy from an MvTx recipient.
Figure 15B:
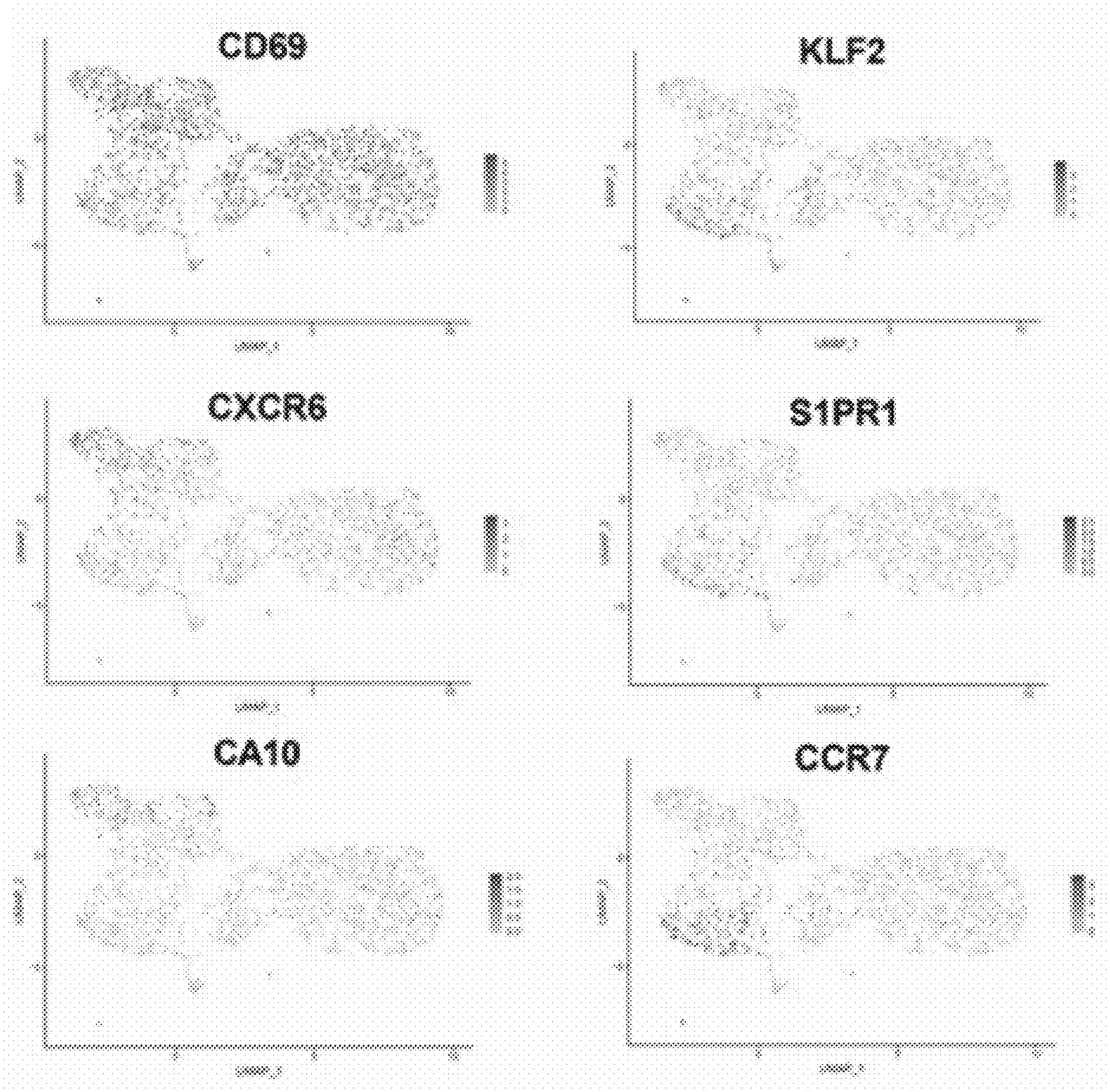
Figure 15C:
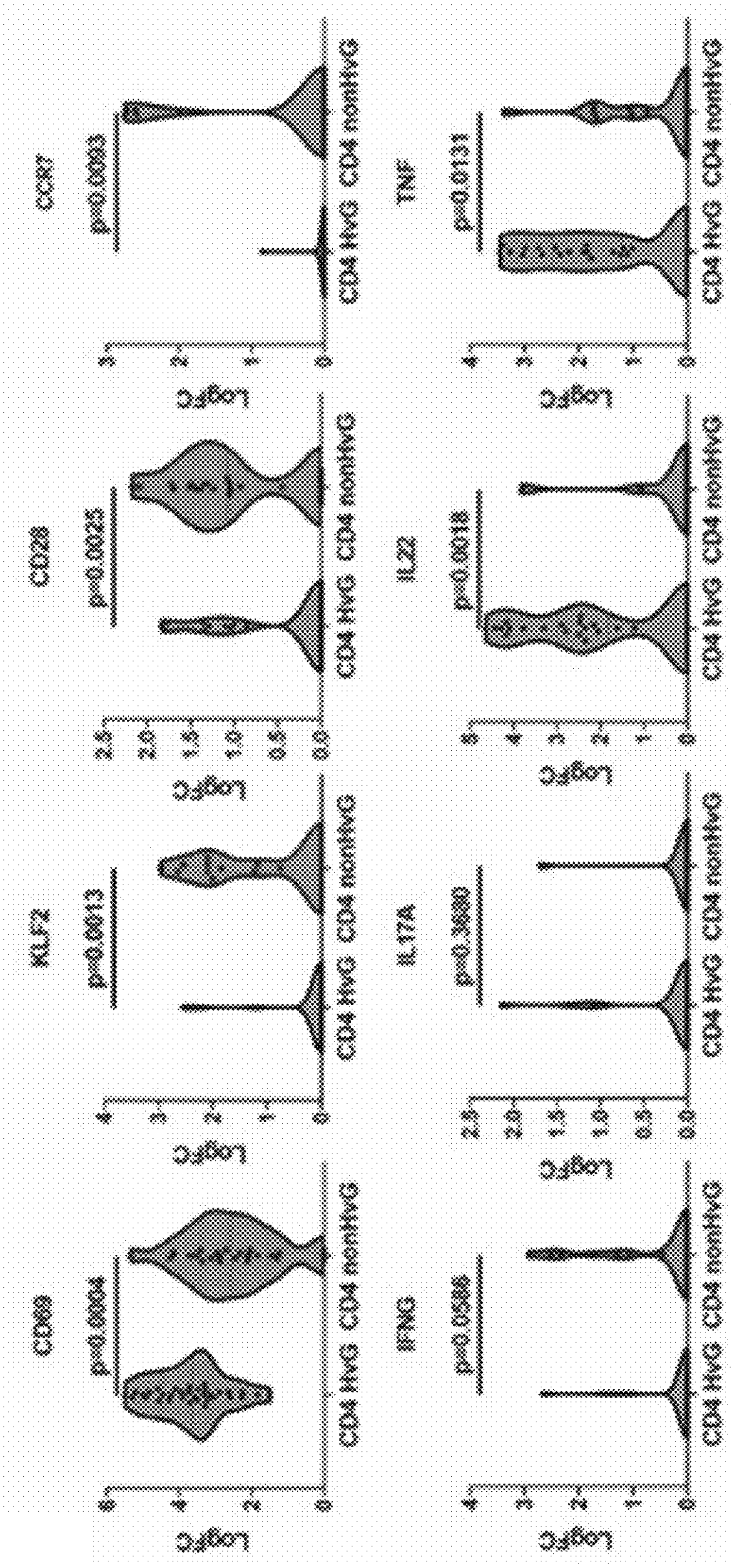
Figure 15D:
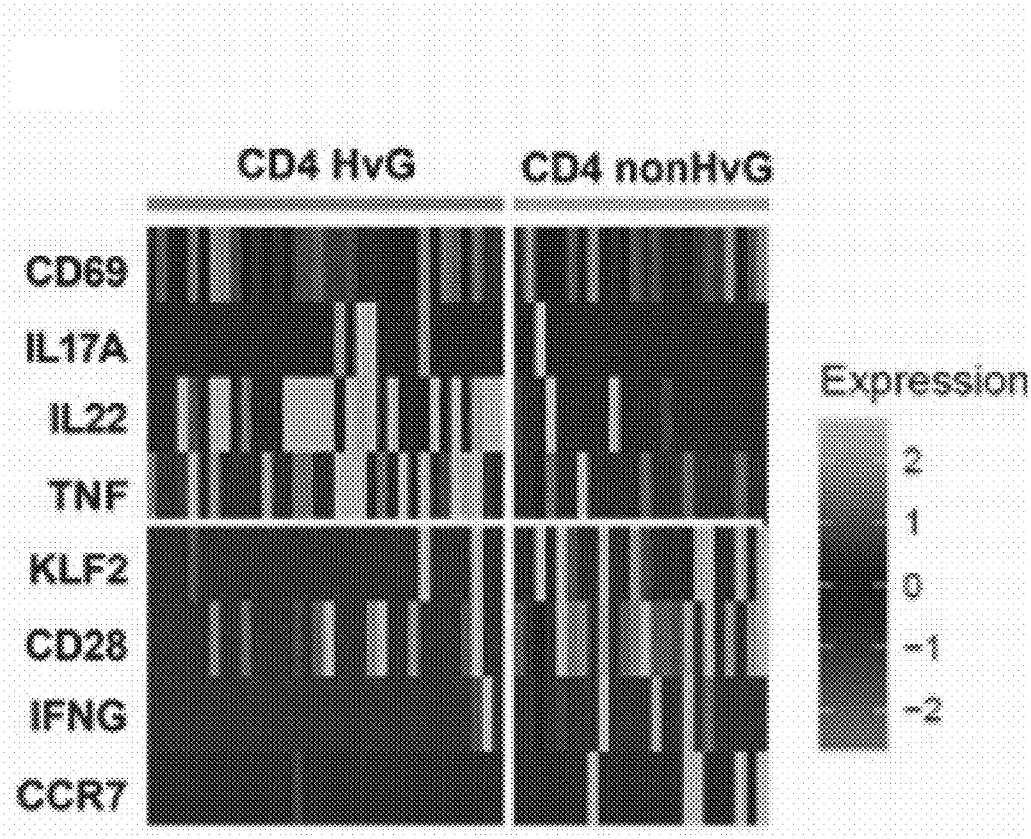

BM for donor and recipient T cells, phenotype and TCR repertoire can be analyzed. BM in mice and humans is thought to be a reservoir for long-lasting, antigen-independent, memory T cell maintenance. BM T cells can rapidly acquire effector function and eliminate pathogen-infected cells and cancer cells. They are maintained in a largely quiescent state, thought to undergo maintenance proliferation in response to BM stromal cytokines and have phenotypic features of TRM, including CD69 and lack of CD28 on CD8 T cells. There is uncertainty whether the BM is a true niche for long-term residency or whether there are separate niches for resident and non-resident memory T cells. It is unknown whether T cells from an organ allograft can enter the BM. In some cases, LGvHR can be mediated by GvH-reactive T cells migrating from the graft to the circulation and into the recipient BM. The demonstration of donor-derived T cells in the bone marrow of ITx recipients and the presence of GvH TCR sequences among them in all cases (FIG. 8 and FIG. 9) is consistent with such an LGvHR Further evidence supporting an intestinal allograft mucosa origin for these clones is shown in in FIG. 14, which illustrates the presence of the same GvH clones at different times in the recipient BM, PBMC and allograft biopsy specimens. BM aspirates at 84-150 days post-transplant for phenotypic studies, chimerism analyses and TCR sequencing analyses on donor and recipient T cells. BM aspirates can be obtained during sedation or general anesthesia for endoscopy, stoma closure or other surgeries with consent can be performed. 5-10 ml of iliac crest bone marrow can be aspirated for the sequencing analyses described in Example 4 and for the following multicolor FCM analyses:

Pan-HLA-A, B, C vs donor- and recipient-specific class I mAb with panels can be used for: lineages and HSC/progenitor cells (CD34, CD38, CD45RA, CD90, CD10, CD56, CD19, CD3 and CD14); T cell subsets (CD3, CD4, CD8, CD45RA, CD45RO, CCR7, CD28, CD69, CD31, FOXP3, CD25,CD127); and B cell subsets/plasma cells (CD20, CD19, CD38, CD27, IgM, IgD, IgA, IgG, CD21, CD45RB [MEM-55], CD69, CD138). Donor and recipient naïve, central memory, TEMRA and TRM T cell subsets, B cell precursors and naïve and memory B cells, B resident memory cells, plasmablasts and plasma cells in BM can thereby be measured.

The donor T cells can be detected in the BM of subjects with T cell macrochimerism and enriched for GvH-reactive T cells that can include effector T cells (Teff) that later become TRM, demonstrating dynamic interrelationships of BM and graft-derived memory T cells. However, de novo T cell generation from CD34+ cells in the multivisceral graft and/or the CD34+ cell infusion can contribute donor lymphocyte subsets that can be increased in recipients of CD34+ cell infusions compared to controls. TCR sequencing studies in this example can be combined with this analysis to determine the likelihood of de novo origin of donor T cells detected in the recipient marrow in each group. With HSC/progenitor chimerism studies, T cell analyses can provide insights into the mechanisms underlying long-term multilineage mixed chimerism and its association with freedom from moderate or severe rejection and DSA and into the mechanisms of loss of chimerism over time.

Example 4. Determine the Mechanisms of Graft Protection and Assess Tolerance in MvTx/vMvTx Recipients The interplay between GvH and HvG alloreactivity within the graft, the peripheral blood, and the recipient bone marrow in subjects in the trial in Example 2 can be monitored. The impact of BM CD34+ cell infusion on HvG tolerance and its mechanisms can be determined. These studies can employ the high throughput TCR sequencing-based approach to identify and track alloreactive TCRs along with polychromatic FCM and single cell RNA sequencing (RNA-seq) combined with paired TCR $\alpha$ and $\beta$ sequencing. With these tools, GvH-reactive T cells can be enriched in the circulation early post-transplant of MVTx and vMvTx and can show evidence of effector function by RNA profiling. Moreover, HvG clones entering the graft early post-transplant can demonstrate effector function by RNA-seq and later acquire the T resident memory (TRM) phenotype. Moreover, long-term donor T cells in the circulation can be demonstrated to be specifically tolerant to the recipient by a mechanism that is only partially Treg-dependent. The preliminary data suggest a combination of central deletion and Treg-mediated tolerance in the GvH direction and possible central deletion of recipient HvG T cells developing de novo post-transplant. The augmented and prolonged chimerism associated with CD34+ hematopoietic stem cell or hematopoietic progenitor cell infusion in MvTx and vMvTx recipients can be associated with more profound tolerance of HvG-reactive T cells due to the persistent presence of donor APCs in the recipient thymus and that this can NOT be mediated by a predominant Treg-dependent mechanism but instead by deletion of donor-reactive T cells developing de novo in the recipient thymus following the transplant. Using TCR sequencing approach, gradual deletion in the peripheral circulation of pre-existing donor-reactive TCRs in recipients of donor CD34+ cell infusions can be observed as observed in subjects who developed tolerance following combined kidney and BMT.

The interplay between GvH and HvG-reactive T cells in the recipient bone marrow can be assessed. By using the bone marrow specimens obtained in Example 2 can be utilized for high-throughput TCRO CDR3 sequencing on bulk sorted donor and recipient BM T cells, compare repertoires to pre-transplant and post-transplant donor and recipient T cells, including the possible contribution of donor naïve T cells developing post-transplant (FIG. 2). These TCR sequencing studies can be combined with phenotypic analyses in Example 3 to determine the likelihood of de novo origin of donor T cells detected in the recipient marrow in each group. Donor BM T cells in subjects with T cell chimerism but not receiving donor CD34+ cell infusion can be enriched for GvH clones rather than tolerant donor T cells generated de novo post-transplant (detected in blood), whereas de novo generated donor T cells can be prominent in BM of subjects who receive donor CD34+ cell infusions. Quantification of HvG clones in the BM can assess whether GvH clones and/or donor T cell or CD34+ cell veto activity can destroy HvG T cells or, if HvG reactivity is not attenuated, into the role of BM HvG alloreactivity in causing eventual loss of chimerism. A reciprocal relationship between numbers of BM GvH clones and HvG clones can be observed. These studies, combined with phenotypic analyses, can provide insight into the mechanism of BM chimerism and into the impact of donor BM infusion in MvTx and LITx recipients.

The bone marrow specimens obtained in Example 2 can be utilized for BM of subjects with blood T cell macrochimerism contains GvH-reactive clones, small aliquots of cells cryopreserved from the initial specimen can undergo single cell 5' RNA-sequencing combined with TCRaP sequencing. Single cell RNA-sequencing combined with TCR sequencing can be carried out on the same single cells using single cell 5' transcriptional analysis platform in combination with the single cell V(D)J enrichment kit that amplifies TCR $\alpha$ and $\beta$, allowing high capture rates for both full length TCR chains in combination with transcriptional profiles for each individual cell. This can allow assessment of the precise functional phenotype of thousands of single T cells (up to 10,000). The number of cells analyzed in this manner can be determined by the percentage of GvH clones detected in part i). If bulk sequencing demonstrates the presence of HvG clones among recipient T cells, similar single cell analyses can be carried out on sorted recipient T cell clones to determine the functional phenotype of HvG clones, determining the impact of donor chimerism on their function.

FIG. 15 illustrates this combined paired TCRα/TCRβ and 5' RNA-sequencing analysis on single cells from mucosal biopsies obtained from subjects. The analysis was performed during a period of graft quiescence. The TCRβ sequences detected in single cell analysis can be mapped to the HvG and non-HvG recipient T cell repertoires that had been identified pre-transplant. The data show that HvG T cells acquire the tissue resident memory (TRM) phenotype during periods of quiescence and that non-HvG recipient T cells pre-existing in the lymphoid tissues prior to transplantation acquire a distinct effector phenotype in the intestinal allograft mucosa (FIG. 15), suggesting that they migrate into the allograft to mediate particular immune activities, possibly protection against microbial pathogens. These results demonstrate the power of the single cell analysis combined with the pre-transplant determination of alloreactive repertoires to identify the functional phenotype of T cell populations in various tissues following the transplant. This approach of single cell RNA-seq (Smart-seq) can be employed on sorted single donor T cells from mucosal biopsies and were able to identify GvH-reactive T cells, analyze their RNA expression patterns individually and interrogate them for a TRM phenotype.

The separate 5' cDNA (50,000 reads per cell) and 5'V(D)J TCR (5,000 reads per cell) sequencing libraries can be integrated and analyzed. This approach can allow assessment of the precise functional phenotype of individual T cells that can include GvH-reactive (or HvG-reactive) cells that are recognizable by their TCRβ chain being among the set defined as GvH-(or HvG)-reactive in pre-transplant donor anti-recipient MLR. All 3 subjects receiving BM infusion as well as contemporaneous controls not receiving BM infusion (see Example 2) can be compared. 200-2000 FACS-sorted donor and/or recipient T cells can be analyzed. The number to be sequenced can be based on the level of chimerism and T cell counts, which can determine the number of donor and recipient T cells available.

Figure 2C:
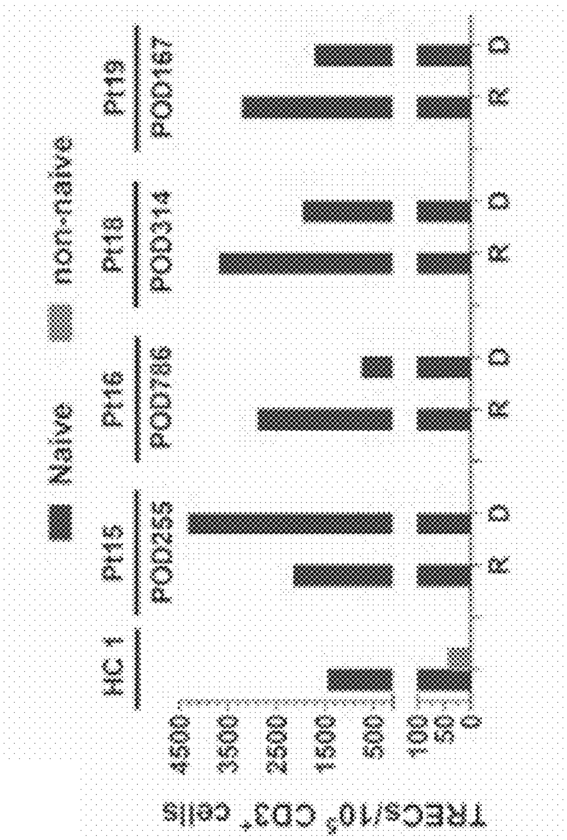
FIG. 2C illustrates high levels of T cell receptor excision circles (TRECs) in donor (D) T cells (similar to levels in recipient (R) T cells) in recipient circulation. HC denotes healthy control.
Figure 2B:
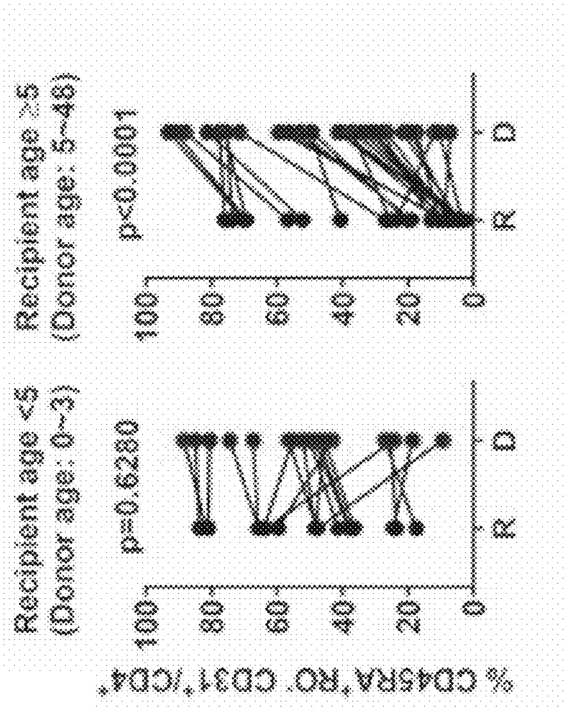
FIG. 2B illustrates abundances of recent thymic emigrants (RTEs) among long-term circulating donor T cells in ITx recipients (percent RTEs among recipient T cells (R) and donor T cells (D) at the same time point).
Figure 2D:
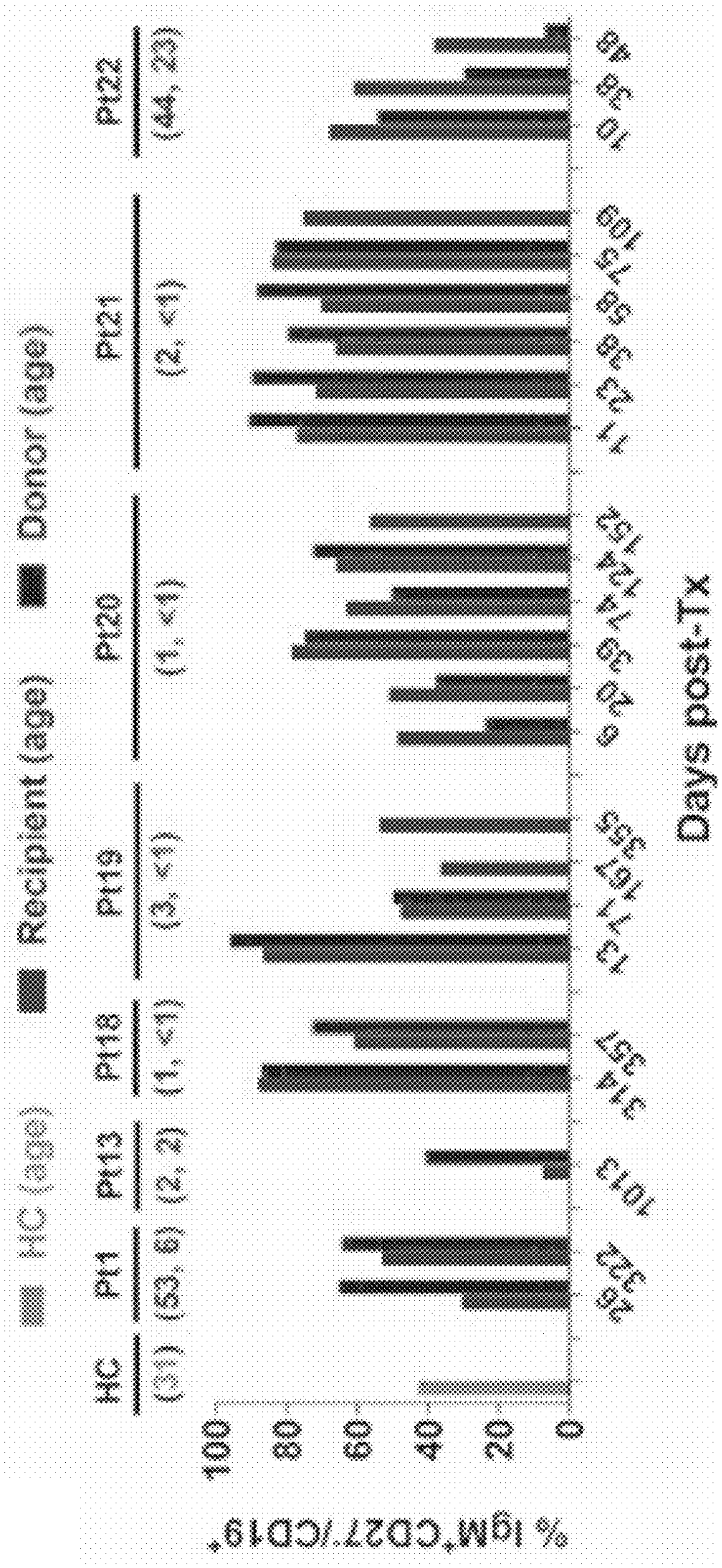
FIG. 2D illustrates presence of naïve donor B cells in recipient circulation.
Figure 16A:
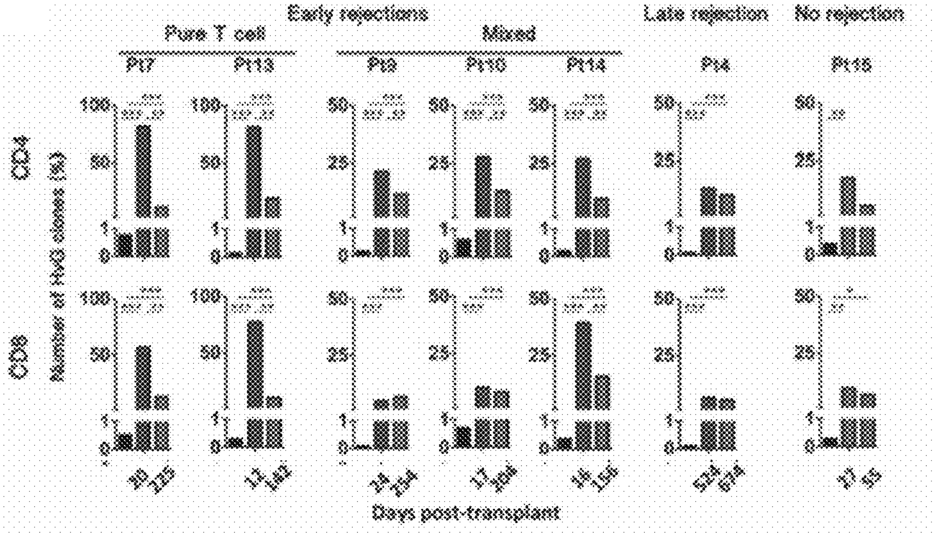
Figure 16B:
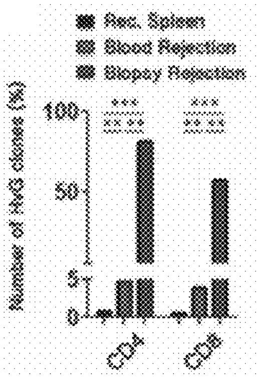
Figure 17:
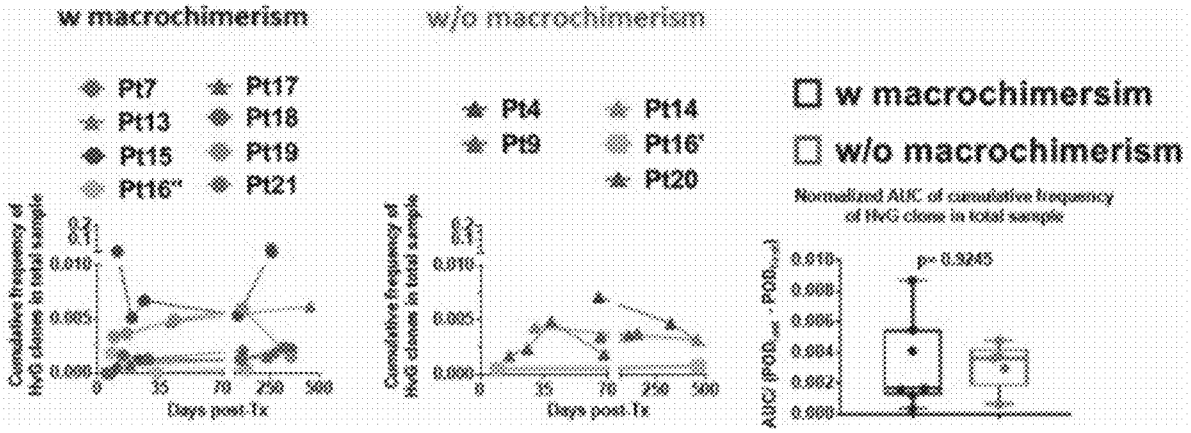
FIG. 17 illustrates cumulative frequencies of HvG clones over time in recipients of MV11(or ilTx grouped by the presence or absence of macrochimerism (peak T cell chimerism >4%). The right panel integrates the data for each subject over time (Area Under the Curve, AUC) and normalizes for the time period covered.

Methods for assessing the relationship between circulating GvH- and HvG-reactive donor T cells in MvTx and LITx recipients with and without CD34+ cell infusion to effector differentiation and expansion of mucosal TRM with GvH cross-reactivity migrates to the circulation and attenuation of HvG reactivity Bulk TCRβ CDR3 sequencing on sorted donor and recipient peripheral blood T cells can be performed at early and late timepoints to quantify GvH and HvG reactivity in the circulation. The induction regimen used does not completely deplete pre-existing recipient T cells, as clearly seen in the entry of pre-existing recipient T cells into the allograft and persistence of HvG T cells in the graft and periphery (FIG. 10 and FIG. 16). Moreover, persistent HvG sequences can be detected in the recipient circulation over time, even in subjects with macrochimerism (FIG. 17). While these cells can be diluted by newly developing T cells following ITx, particularly in younger subjects with robust thymic function and high percentages of RTE in the circulation (FIG. 2B and FIG. 2C). Other mechanisms such as gradual deletion (perhaps due to direct cytotoxicity of GvH clones or veto activity of donor T cells or CD34+ cells) might lead to the actual disappearance of pre-existing donor-reactive T cells in tolerant subjects, as observed in tolerant recipients of combined kidney and BMT who had had transient chimerism. *Ibis* high throughput TCR sequencing approach can determine whether or not there is gradual deletion in the peripheral circulation of preexisting donor-reactive TCRs in control recipients and recipients of donor CD34+ cell infusions. Using high throughput sequencing with the Adaptive Immunoseq platform of PBMCs collected at 6, 11, 16, and 21 months post-transplant, the fate of pre-existing HvG T cells in the circulation relative to pre-existing non-HvG T cells with those in historical and concurrent MvTx recipients can be compared.

Single cell TCR sequencing with transcriptional profiling can assess functional phenotypes of circulating GvH- and HvG-reactive T cells. Similar to the BM analyses proposed in Example 4, single cell RNA-sequencing combined with TCR sequencing on the same single cells can be utilized by single cell 5' transcriptional analysis platform in combination with the single cell V(D)J enrichment kit that amplifies TCR α and β, allowing high capture rates for both full length TCR chains in combination with transcriptional profiles for each individual cell. The separate 5' cDNA (50,000 reads per cell) and 5'V(D)J TCR (5,000 reads per cell) sequencing libraries can be integrated and analyzed using the Cell Ranger 2.1/Loupe pipeline. GvH-reactive effector T cells can be enriched in the circulation early post-transplant, perhaps especially in MVTx recipients. All 3 subjects receiving BM infusion as well as contemporaneous controls not receiving BM infusion (see Example 2) can be compared. 200-2000 FACS-sorted donor T cells in the circulation during the period of peak LGvHR (days 0-30) can be analyzed. The number to be sequenced can be based on the level of chimerism and T cell counts, which can determine the number of donor T cells available. In addition to TCR sequencing that can be interrogated against the GvH repertoire defined by high throughput sequencing of the pre-transplant MLR, each cell for evidence of activation (CD25, CD69), effector function (Tbet, IFNg, TNF, IL-2, IL-6, IL-17, etc) and cytotoxic function (perforin, granzymes) by RNA profiling can be interrogated. The expression of a TRM-associated RNA profile as described can be examined for the same GvH clones in the circulation and in intestinal biopsies (e.g. FIG. 14), suggesting that donor graft-derived TRM are a source of circulating GvH-reactive T cells after they are activated by recipient APCs found in the intestinal mucosa early post-transplant.

Methods for assessing the functional phenotype of mucosal GvH-reactive donor T cells in MvTx and LITx recipients for effector differentiation and expansion of mucosal TRM with GvH cross-reactivity to attenuate HvG clonal numbers and/or effector function Bulk TCRP CDR3 sequencing on serial biopsy specimens to compare the ratio of GvH to HvG clones can be performed as shown in FIG. 10. The infusion of donor CD34+ cells can be associated with increased ratios of GvH to HvG clones in longer-term biopsies in association with persistent blood chimerism and that these outcomes can correlate with less rejection and the ability to minimize immunosuppression. HvG clones entering the graft early post-transplant can demonstrate evidence for activation and effector function by RNA-seq, while those that persist long-term in subjects with persistent blood chimerism can acquire the TRM phenotype. These studies can also involve single cell RNA-seq combined with TCRαβ, except that recipient T cells sorted from the digested mucosal biopsies can be used for the single cell analysis. As shown in FIG. 16, recipient-mappable host T cells entering the graft mucosa during rejection episodes are greatly enriched for HvG clones identified by the pre-transplant MLR/high throughput sequencing method. While these HvG clones decline in the graft biopsies after resolution of rejection, they still persist at markedly greater frequencies than in the circulation (FIG. 16). However, the recipient mucosal T cells ultimately take on the TRM phenotype. Such observation can indicate that HvG T cells are included in the evolving recipient mucosal TRM population, as strongly suggested by the single cell analysis presented in FIG. 15 These HvG cells as part of the TRM population can contribute to the high risk of graft rejection in these subjects. To confirm that recipient HvG T cells enter the graft as effector cells and join the TRM pool and to determine the impact of donor BM infusion on the HvG response in the graft, surveillance biopsy specimens at the first timepoint following the demonstration of >5% recipient repopulation (biopsies are typically performed twice weekly during the first month and weekly thereafter) and at a late time (6 to 18 months post-transplant) in subjects who have been rejection-free for at least 3 months, and sort recipient T cells for single cell RNA-seq with TCR sequencing can be determined. Using this approach, HvG clones (as determined by pre-transplant MLR and high throughput TCR sequencing) among these T cells, as shown in FIG. 15, can be identified and demonstrated for upregulation of genes encoding effector molecules in these HvG clones during rejection but not during quiescence, when the same clones are expected to have acquired the TRM phenotype. 200-2000 FACS-sorted recipient T cells in this manner can be analyzed. The total number of cells to be analyzed can be determined by estimating the percentage of HvG-reactive T cells among donor T cells in the mucosa on the basis of both FCM and high-throughput TCR sequencing of earlier samples from the same subject.

Methods for determining the mechanism of specific hypo-responsiveness of long-term circulating donor T cells to the recipient GvH tolerance.

Figure 18A:
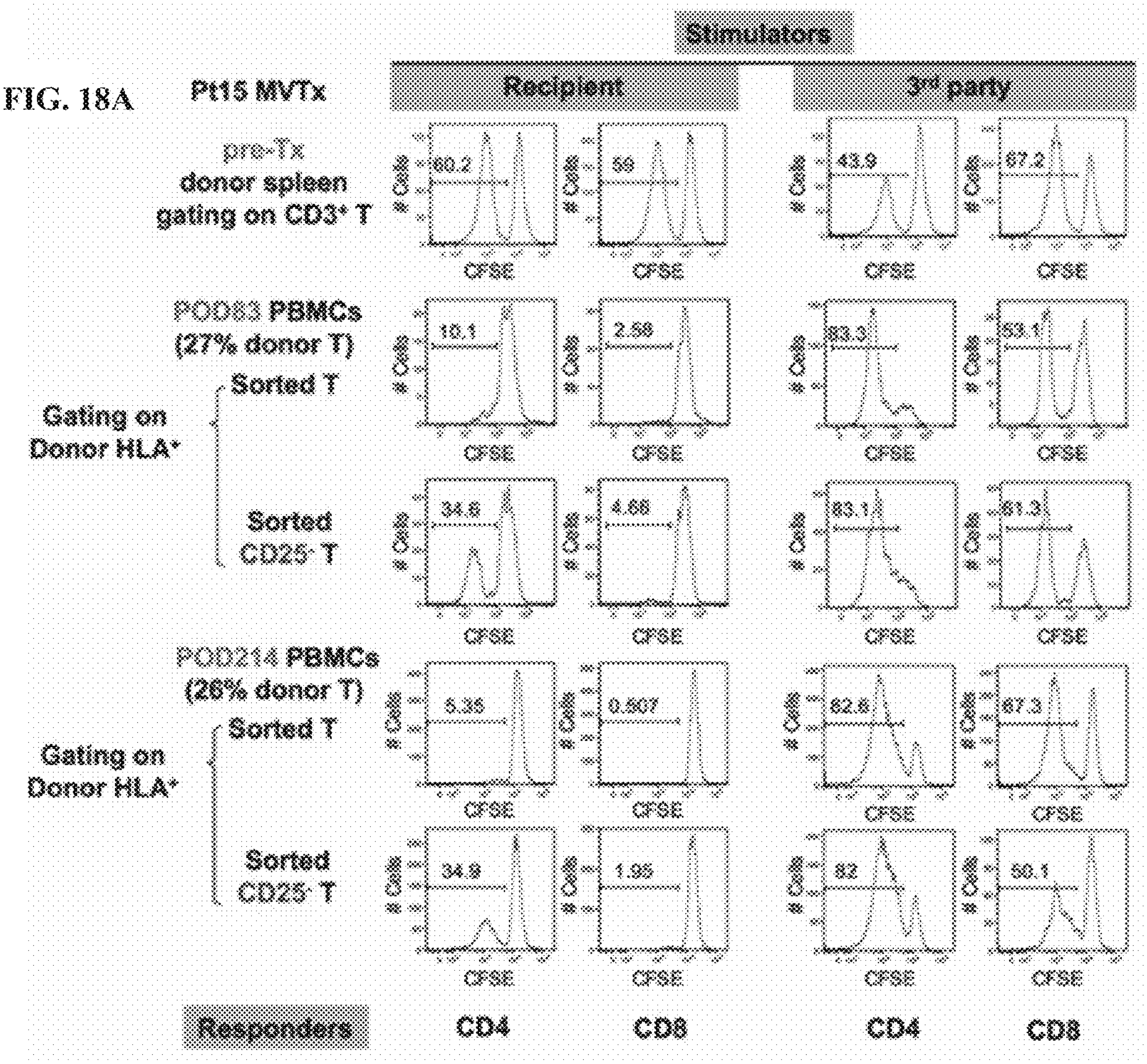
FIG. 18A-18B illustrates that long-lasting (POD>200) circulating and splenic donor T cells are largely tolerant to the recipient but still functional in third party responses.
Figure 18B:
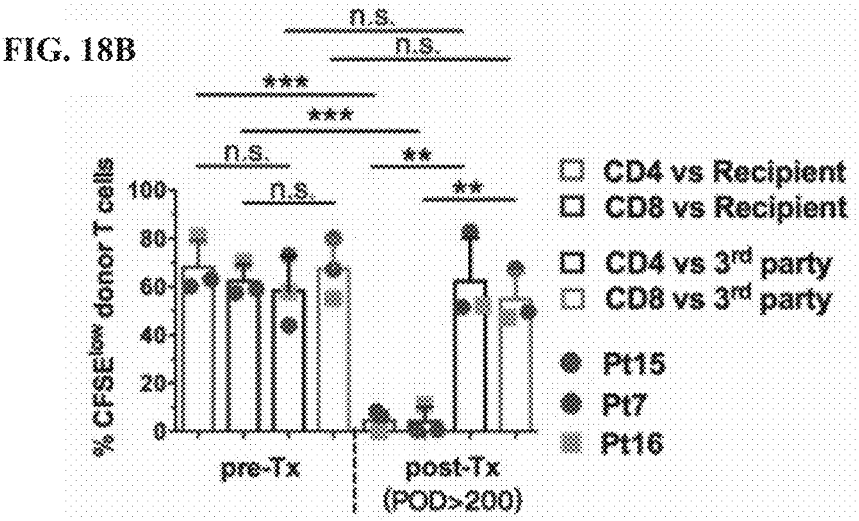

Based on data in FIG. 18, long-term donor T cells in the circulation can be specifically tolerant to the recipient by a mechanism that is only partially Treg-dependent. Based on their recent thymocyte emigrant (RTE) phenotype, their high T-cell receptor excision circle (TREC) content (FIG. 2B-D) and their lack of repertoire overlap with pre-transplant donor T cells, the results so far suggest that long-term donor T cells develop de novo in the recipient thymus. Thus, they are expected to develop in the presence of recipient APCs and be deleted intrathymically of host-reactive T cells. The complete tolerance of these donor T cells to the recipient, as shown in FIG. 18, is consistent with this interpretation. Moreover, FIG. 18 also shows that Treg depletion reveals an auto-MLR for recipient T cells and a similar degree of responsiveness for donor T cells, consistent with the interpretation that central deletion is incomplete and tolerance of the remaining T cells (donor and recipient) to the recipient is mediated by Tregs that are positively selected in the recipient thymus and specific for recipient antigens. Using PBMCs collected at 4, 8 and 12 months post-transplant, CFSE-MLRs against no stimulator, against donor, recipient and 3rd party stimulators and assess the responses of un-depleted and CD25 (Treg)-depleted donor T cells (gated on the basis of staining with donor HLA-specific mAb as in FIG. 18) to the recipient can be carried out.

Methods for assessing and determining the mechanism of recipient hypo-responsiveness to the donor in MvTx and vMvTx recipients.

Figure 19A:
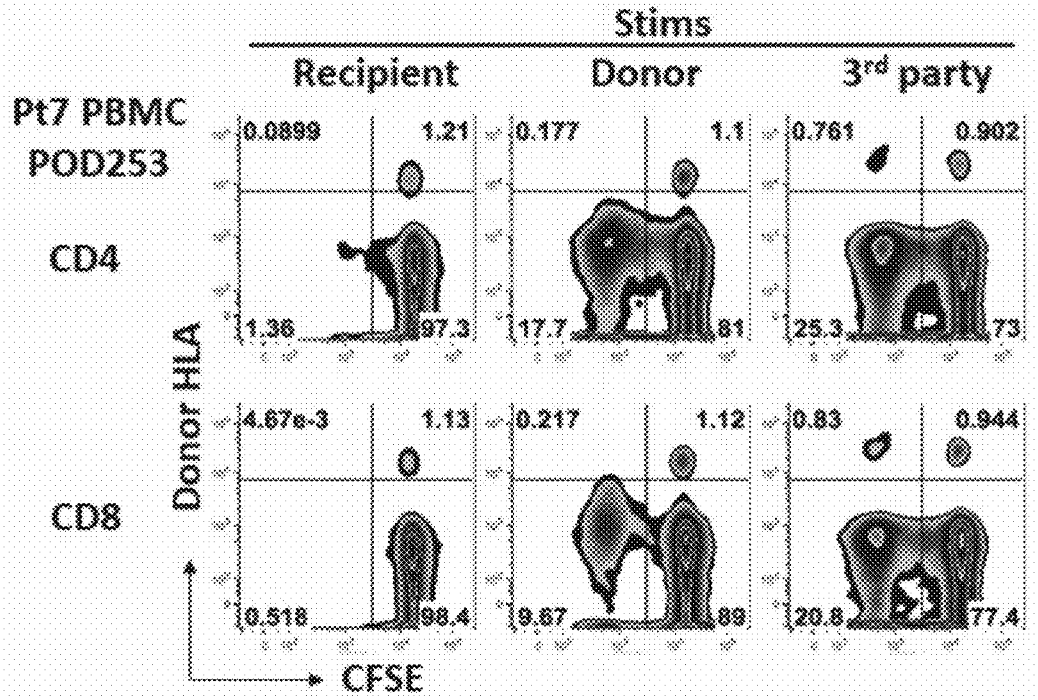
FIG. 19A-19B illustrates that long-term recipient T cells are only partially hyporesponsive to donor antigens in subjects with macrochimerism.
Figure 19B:
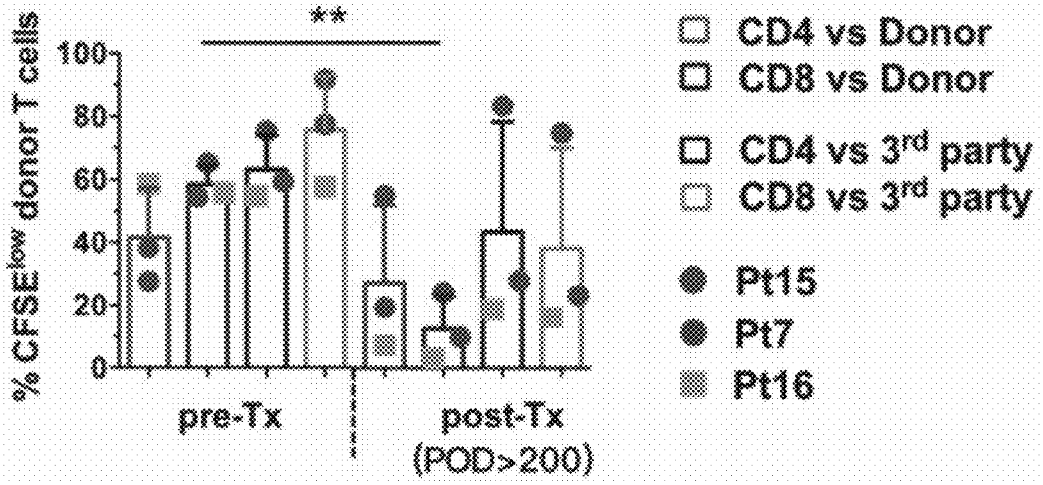

In contrast to GvH tolerance, long-term recipient T cells are only partially hyporesponsive to donor antigens in subjects with macrochimerism (FIG. 19), and this GvH hypo-responsiveness is independent of Tregs. These results are consistent with the possibility that there is a period of donor contribution to the deleting thymic APC population when chimerism is present. However, recipient T cells developing in the thymus prior to the transplant and/or subsequent to the loss of chimerism cannot be deleted of donor-reactive cells. Using gated recipient T cells in the CFSE-MLR assays described herein can address the possibility that augmented and durable chimerism associated with CD34+ hematopoietic stem cell or hematopoietic progenitor cell infusion in MvTx and vMvTx recipients can be associated with more profound tolerance of GvH-reactive T cells due to the persistent presence of donor APCs in the recipient thymus that delete thymocytes recognizing the donor. These results in the 3 subjects on the trial can be compared with those in historical and concurrent MvTx and vMvTx recipients. These results, in combination with studies involving bulk TCR sequencing approach can be interpreted to assess the fate of pre-existing donor-reactive T cells in the circulation over time. It is possible the gradual deletion in the peripheral circulation of pre-existing donor-reactive TCRs in recipients of donor CD34+ cell infusions can be observed, as observed in subjects who developed tolerance following combined kidney and BMT.

Example 5. CD34 Selection from Fresh or Thawed BM from Deceased Donors Using CliniMACS Plus Described herein is protocol for isolating cells expressing CD34 from fresh or thawed bone marrow (BM) from diseased donors.

Buffer and bags preparation

Label five 600 ml Transfer-Pack bags as follows, and record the weight of each bag:

1) Cell Prep Bag 1 (can be more than 1 bag)
2) Plasma Waste
3) Waste 1
4) Waste 2

Buffers:

A. Prepare in Biosafety cabinet (BSC)

B. Labeling Buffer (2 bags):

1) Obtain 2 bags of Plasma Lyte (1 L)
2) Obtain 2 30 cc syringes with 18 gauge needles affixed.
3) Using syringe and needle, inject 20 ml Benzonase (1000 U/ml) and 20 ml HSA (25%) to each 1 L Plasma Lyte bag.
4) Use a new syringe and needle for each injection.
5) Mix well by inverting at least 5 times.
6) Label each bag with "Labeling buffer".
7) Final concentrations are 20U/ml Benzonase and 0.5% HSA.

C. Selection Buffer:

1) Obtain a 1 L bag of Plasma Lyte.
2) Obtain a 30 cc syringe with an 18 gauge needle affixed.
3) Using syringe and needle, inject 20 ml HSA (25%) into a 1 L Plasma Lyte bag.
4) Mix well by inverting at least 5 times.
5) Label the bag with "Selection buffer".
6) Final concentration is 0.5% HAS Preparation for labeling of fresh (A) or frozen (B) bone marrow products A. Protocol for fresh bone marrow product:

1) After grinding and removing fat, centrifuge bone marrow cell suspension in blood collection bags at 300× g for 15 minutes
2) Perform following in a BSC.
3) Combine all bone marrow cell pellets into the Cell Prep Bag 1
4) Rinse all blood collection bags with 50 ml of Rinse media and transfer to Cell Prep Bag 1.
5) Weigh bag.
6) Determine total volume of cell suspension in the Cell Prep Bag 1 by subtracting original weight from that obtained in step 5 of this section. Use the following formula to convert weight to volume: lgram=1 ml.
7) Gently mix Cell Prep Bag 1 with a rotating motion.
8) Use a 1.0 ml syringe to withdraw 0.5 ml bone marrow through a sampling site coupler and transfer to a 1.5 ml Eppendorf tube for CD34+ cell and T cell enumeration using flow cytometry.
9) Fill the Cell Prep Bag 1 with approximately 400 ml Labeling buffer and centrifuge at 300× g for 15 minutes with a brake setting of 4 at room temperature.
10) Reduce volume in Cell Prep Bag 1 to desired volume based on total T cell and CD34+ cell counts as indicated in Table 1.

TABLE 1

Optimal labeling volume and tubing set determination for the selection of CD34+ cells

| | Total Leukocytes [D] | Total CD34+ [E] | Volume of Cell solution before labelling (ml) |
|---|---|---|---|
| Standard-scale (TS) | ≤60 × $10^9$ | ≤0.6 × $10^9$ | 93.5 |
| Large-scale (LS) | ≤60 × $10^9$ | >0.6 × $10^9$ | 187 |
| Large-scale (LS) | >60 × $10^9$-120 × $10^9$ | ≤0.6 × $10^9$ | 187 |
| Large-scale (LS) | >60 × $10^9$-120 × $10^9$ | >0.6 × $10^9$ | 187 |

B. Protocol for thawed bone marrow:

1) Thaw cells in 2 cryobags in a 37° C. water bath
2) Transfer all bags to a BSC
3) Aseptically clean the ports and spike of each bag.
4) Using a 5 cc syringe with affixed needle, immediately inject Benzonase (1000U/ml) into each cryobag to achieve a final concentration of 20U/mL (e.g., for 70 ml of bone marrow product, inject 1.4 mL Benzonase) and mix well.
5) Combine contents from the 2 thawed cryobags into Cell prep Bag 1 by withdrawing using a 100 mL syringe attached to the transfer port.
6) Rinse each bag with 50 ml of Labeling buffer and slowly transfer to same Cell Prep Bag 1.
7) Record weight of Cell Prep Bag 1.
8) Record total volume of cell suspension in the Cell Prep Bag 1 (should no more than 200 mL) by subtracting the original weight from the weight obtained in step 7 (1 gram=1 mL).
9) Slowly fill Cell Prep Bag 1 with an equal volume of Labeling buffer by adding 10% of the volume per minute while shaking on a shaker.
10) Quickly add another volume of Labeling buffer to Cell Prep Bag 1.
11) After mixing well, remove 0.5 ml sample for T cell and CD34+ cell enumeration by flow cytometry.
12) Optional step: If clumps are present, insert standard blood filter, filter the cells and transfer to the second Cell Prep Bag.
13) Centrifuge at 300× g for 15 minutes with a brake setting of 4 at room temperature.
14) Express supernatant, gently mix cell pellet and combine all cells into one bag.
15) Wash bags and adjust volume to target volume with Labeling buffer according to Table 1.

Cell labeling and selection

A. Add human IVIG to Cell Prep Bag at final concentration 1.5 mg/ml.
B. The calculated volume of IVIG added should be included in the final labeling weight, not to exceed 95 g or 190 g, depending on scale of preparation (Table 1).
C. Inject 100 ml of sterile air into the bag using a 100 ml syringe with affixed 0.2 micron filter
D. Place the Cell Prep Bag on an orbital rotator and gently shake for 5 minutes at room temperature.
E. After 5 minutes, using a 20 ml syringe, inject 1 vial (7.5 ml) of CD34+ Reagent for Standard-scale or 2 vials (15 ml) for Large-scale into the Cell Prep Bag through the sampling site coupler.
F. Incubate bag on the orbital rotator for 30 minutes at room temperature.
G. In BSC, remove air in Cell Prep Bag using a 100 ml syringe. Add 500±10 ml (g) of Labeling buffer to the Cell Prep Bag. Centrifuge at 300× g for 15 minutes, with a brake setting of 4 at room temperature.
H. Remove as much of the supernatant as possible (at least 500 ml for standard-scale and 450 ml for Large-scale) from the Cell Prep Bag using a plasma press. Be careful not to remove cells.
I. Record the amount of supernatant removed.
J. Add 500±10 ml (g) of Labeling buffer to the Cell Prep Bag.
K. Centrifuge at 300× g for 15 minutes, with a brake setting of 4 at room temperature.
L. Remove as much of the supernatant as possible (at least 500 ml for standard-scale and 450 ml for Large-scale) from the Cell Prep Bag using a plasma press.
M. Gently mix cell pellet and resuspend pellet with Labeling buffer 1 to target volume 140 ml for standard-scale preparation or 265 ml for large-scale.
N. Inside the BSC, transfer 0.5 ml bone marrow using a 1 mL syringe to a 1.5 ml Eppendorf tube to perform pre-CliniMACS QC including cell count, T cell and CD34+ cell enumeration.
O. The product is ready to process on the CliniMACS plus instrument according to the Manufacture's instruction with the exception that custom Selection buffer is used instead MACS buffer.
P. The volume of the selected cells at the end is expected to be ~40-50 ml for the standard selection tubing set and ~75-80 ml for large selection.
Q. Obtain samples for product QC.
R. Selected cells are ready for immediate infusion or cryopreservation.

Example 6. Donor-Derived GvH-Reactive T Cells and HSPCs Enter Recipient BM

A study has shown that functional donor-derived HSPCs in human intestinal allografts are present and that these contribute to long-term multilineage (T/B/NK/myeloid) blood chimerism, which is frequently observed in MVTx patients.

The data presented here shows that multilineage chimerism in blood after ITx involves a LGVHR from GvH-reactive donor T cells migrating from the recipient circulation to the BM, making space for engraftiment of HSPCs from the graft.

Figure 20A:
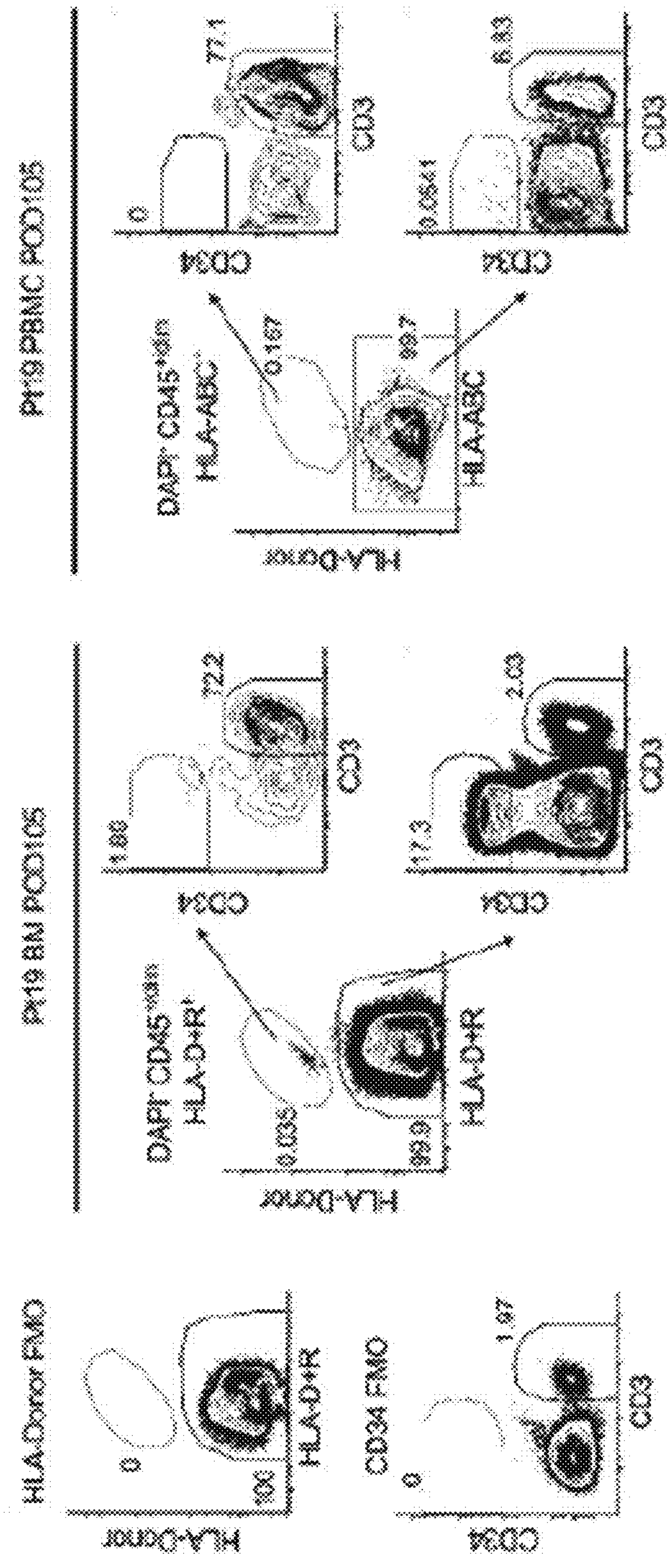
FIG. 20A-20D illustrates that lymphohematopoietic graft-vs-host responses (LGvHR) occurs in the bone marrow of a subject.
Figure 20B:
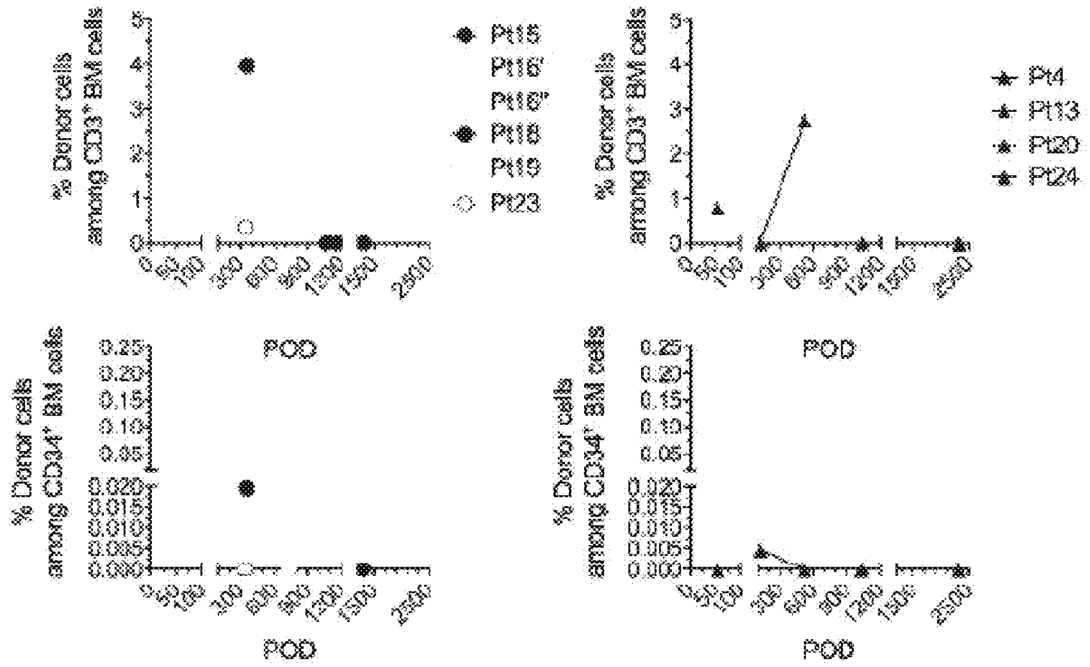
Figure 20C:
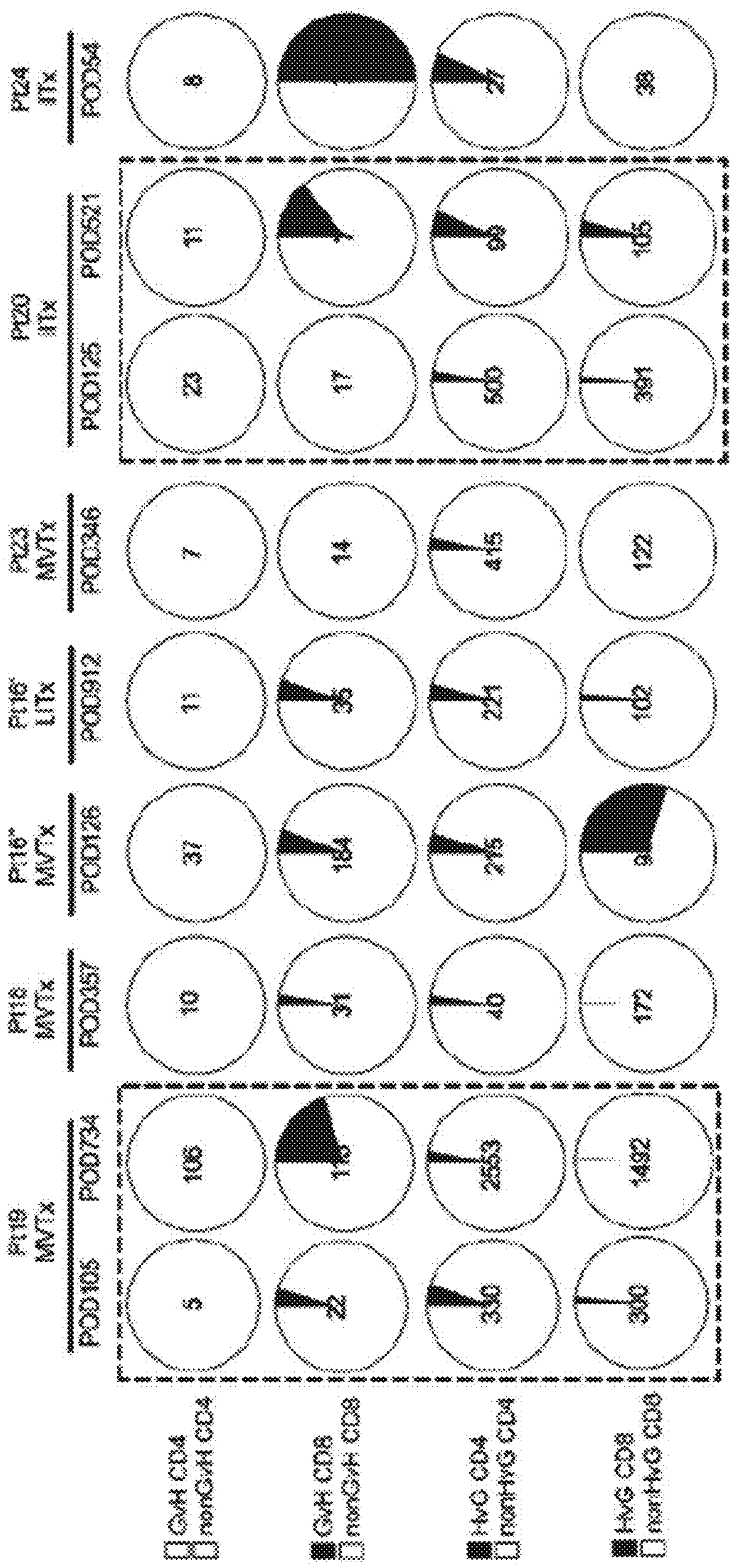
Figure 20D:
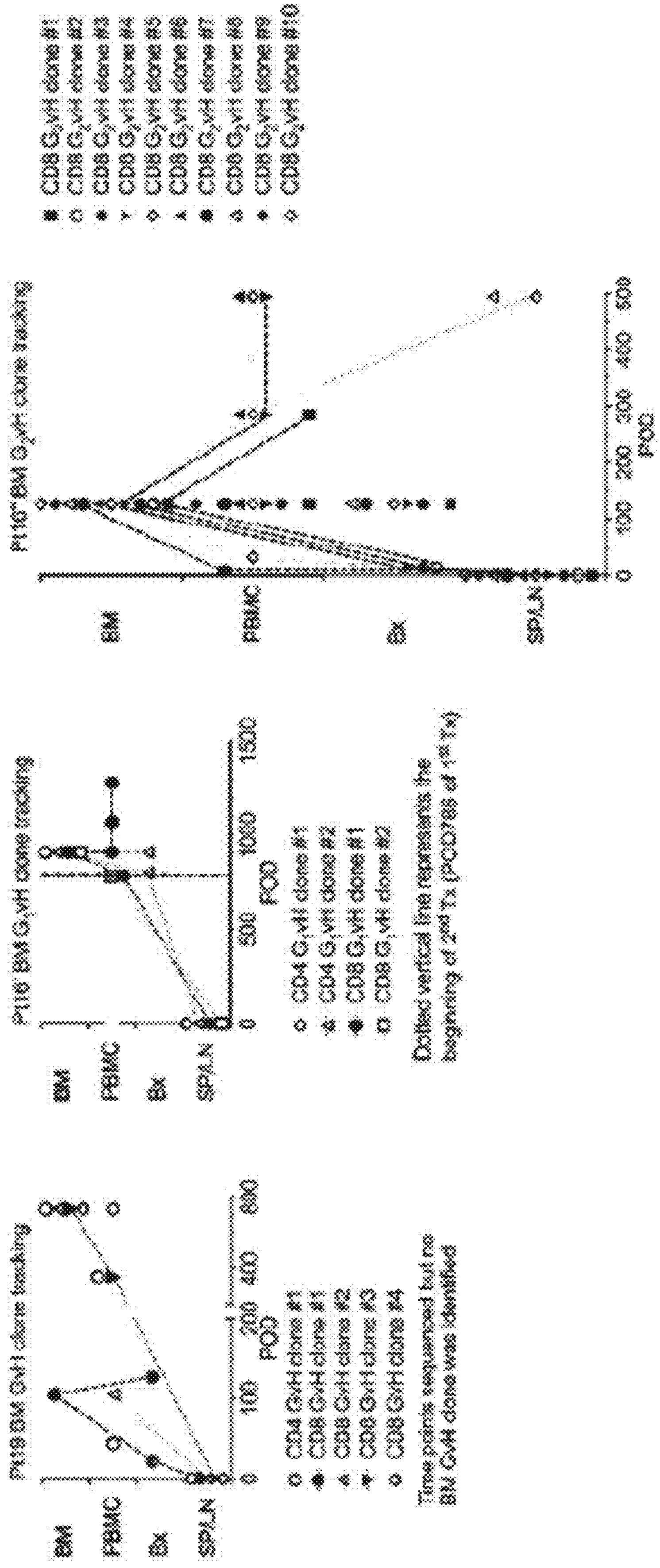

As shown in FIG. 203, donor-derived CD3+ T cells and CD45+/dimCD34+ HSPCs (FIG. 20A) were simultaneously detected in the BM of 4 of 6 composite graft transplants (Pt16', LITx; Pt16", Pt18, and Pt19, MVTx), and in 1 of 4 iITx recipients (Pt20). Bone marrow (BM) CD34 cell chimerism detected by flow cytometry was confirmed by PCR-based single nucleotide polymorphism (SNP) variant detection (Scisco Genetics) in 2 of2 patients (Pt16" and Pt19). TCR-β CDR3 DNA sequencing identified GvH clones among donor-mappable BM T cells in the 3 patients with donor T cells in recipient BM. In Pt19, whose BM was sampled twice, the later (POD734) sample demonstrated an increased frequency of GvH clones, which was associated with a decline in the frequency of HvG clones detected in the same samples. As shown in FIG. 20C, this MVTx recipient was rejection-free through the post-transplant (Tx) follow-up period. Although GvH clones were dominant among donor T cells in the BM of iITx recipient Pt24 on POD54 (FIG. 20C), there were no detectable donor-derived CD34+ HSPCs in this sample (FIG. 20B). In iITx recipient Pt20, GvH clones were only detectable in the BM at the late (POD521), but not the early (POD125), time point assayed, and the low CD34 chimerism detected at POD125 disappeared by the later time point (FIG. 20B and FIG. 20C). As shown in FIG. 20D, individual GvH clones identified in the BM were further tracked to check for their earlier presence in other tissues. In 3 of 6 transplants (Pt19, Pt16", Pt16'; FIG. 20D), at least 3 GvH clones that preexisted were identified in either the ileum biopsy or PBMCs before their detection in recipient BM. Proportional Venn diagram analysis using all TCR-β sequences detected in the ileum biopsy, PBMCs, and BM cells collected on the same day in 3 MVTx recipients (Pt19, Pt18, Pt16") demonstrate minimal clonal overlap between BM versus PBMCs (6.54%±7.27%), which is as low as that for ileum biopsy versus PBMCs (3.31%±3.17%) (paired t test, P=0.52), largely excluding potential blood contamination as an explanation for the detection of GvH clones in the BM.

Example 7. Cadaveric CD34+ Cells Promote Long-Term Multilineage (T/B/NK/myeloid) Blood Chimerism In Organ Transplant Recipients The studies outlined in Example 6 were replicated with CD34+ cells prepared from cadavers as described herein and in PCT/US2021/055081 filed on Oct. 14, 2021, which is herein incorporated by reference in its entirety. The methods of administration follow Example 2 as described herein.

Following cadaveric CD34+ cell administration to organ transplant recipients according to Example 2, donor-derived CD3+ T cells and CD45+/dimCD34+ cells are simultaneously detected in the bone marrow (BM) of 4 of 6 composite graft transplants, and in 1 of 4 iITx recipients. BM CD34 cell chimerism detected by flow cytometry is confirmed by PCR-based single nucleotide polymorphism (SNP) variant detection (Scisco Genetics) in 2 of 2 patients. TCR-0 CDR3 DNA sequencing identifies GvH clones among donor-mappable BM T cells in the 3 patients with donor T cells in recipient BM. In one subject, whose BM was sampled twice, the later sample demonstrates an increased frequency of GvH clones, which is associated with a decline in the frequency of HvG clones that are detected in the same samples. This subject is rejection-free through the post-transplant (Tx) follow-up period. In another subject, GvH clones are only detectable in the BM at the late (POD521), but not the early (POD125), time point assayed, and the low CD34 chimerism detected at POD125 disappears by the later time points. Individual GvH clones identified in the BM are further tracked to check for their earlier presence in other tissues. In 3 of 6 transplants, at least 3 GvH clones that preexisted are identified in either the ileum biopsy or PBMCs before their detection in recipient BM. Proportional Venn diagram analysis using all TCR-β sequences detected in the ileum biopsy, PBMCs, and BM cells are collected on the same day in 3 recipients demonstrate minimal clonal overlap between BM versus PBMCs, which is as low as that for ileum biopsy versus PBMCs, largely excluding potential blood contamination as an explanation for the detection of GvH clones in the BM.

While the foregoing disclosure has been described in some detail for purposes of clarity and understanding, it can be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A method of establishing a mixed chimerism, establishing a T-cell macrochimerism of at least about 4%, preventing a host-versus-graft response, and/or preventing a rejection of a donor organ in a subject wherein said subject has received an organ transplant, the method comprising administering to said subject a population of CD34+ cells, wherein the organ transplant comprises a multivisceral transplant comprising transplantation of two or more of stomach, pancreas, liver, small intestine, large intestine, and kidney.

2. The method of claim 1, wherein said population of CD34+ cells comprises at least about $1\times10^6$ CD34+ cells per kilogram of said subject.

3. The method of claim 1, wherein said administering to said subject the population of CD34+ cells occurs about 1 to about 30 days after said organ transplant.

4. The method of claim 1, wherein said organ transplant comprises two or more organs that comprise a population of hematopoietic stem cells or hematopoietic progenitor stem cells.

5. The method of claim 1, wherein said population of CD34+ cells comprises no more than about $1\times10^4$ CD3+ cells per kilogram of said subject.

6. The method of claim 1, wherein said population of CD34+ cells comprises CD34+ cells that are HLA-matched to said organ transplant.

7. The method of claim 1, wherein the method further comprises administering rabbit anti-thymocyte globulin to said subject.

8. The method of claim 1, wherein the method further comprises administering one or more corticosteroids to said subject on the day of, and/or one or more days after, said organ transplant.

9. The method of claim 1, wherein the method further comprises administering tacrolimus to said subject.

10. The method of claim 1, wherein administering to said subject the population of CD34+ cells does not result in a Grade II or greater graft-versus-host disease within a month, within a year, or within three years after said organ transplant.

11. The method of claim 1, wherein the method further comprises administering one or more mTOR inhibitors to said subject.

12. A method of generating donor derived T cells in an organ transplant recipient, the method comprising administering bone marrow stem cells comprising a population of CD34+ cells, wherein the organ transplant comprises a multivisceral transplant comprising transplantation of two or more of stomach, pancreas, liver, small intestine, large intestine, and kidney.

13. The method of claim 12, wherein said population of CD34+ cells is selected for such that said population of CD34+ cells comprises no more than about $1\times10^4$ CD3+ cells per kilogram of said subject.

14. The method of claim 12, wherein said population of CD34+ cells comprises CD34+ cells that are HLA-matched to said organ transplants.

15. The method of claim 12, wherein said population of CD34+ cells are obtained from the same person as said donor organ, or said population of CD34+ cells are not obtained from the same person as said donor organ.

* * * * *